(12) United States Patent
Draghia-Akli et al.

(10) Patent No.: US 7,517,863 B2
(45) Date of Patent: Apr. 14, 2009

(54) ENHANCED SECRETION/RETENTION OF GROWTH HORMONE RELEASING HORMONE (GHRH) FROM MUSCLE CELLS BY SPECIES-SPECIFIC SIGNAL PEPTIDE

(75) Inventors: Ruxandra Draghia-Akli, Houston, TX (US); Melissa Pope, The Woodlands, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 43 days.

(21) Appl. No.: 11/034,682

(22) Filed: Jan. 13, 2005

(65) Prior Publication Data

US 2005/0171046 A1 Aug. 4, 2005

Related U.S. Application Data

(60) Provisional application No. 60/537,582, filed on Jan. 20, 2004.

(51) Int. Cl.
 A01N 43/04 (2006.01)
 C07H 21/02 (2006.01)
(52) U.S. Cl. ...................................... 514/44; 536/23.1
(58) Field of Classification Search ................. 514/44; 536/23.1
 See application file for complete search history.

(56) References Cited

U.S. PATENT DOCUMENTS

| | | |
|---|---|---|
| 4,223,019 A | 9/1980 | Momany et al. |
| 4,223,020 A | 9/1980 | Momany et al. |
| 4,223,021 A | 9/1980 | Momany et al. |
| 4,224,316 A | 9/1980 | Momany et al. |
| 4,226,857 A | 10/1980 | Momany et al. |
| 4,228,156 A | 10/1980 | Momany et al. |
| 4,228,158 A | 10/1980 | Momany et al. |
| 4,410,512 A | 10/1983 | Bowers et al. |
| 4,833,166 A | 5/1989 | Grosvenor et al. |
| 4,839,344 A | 6/1989 | Bowers et al. |
| 5,023,322 A | 6/1991 | Kovacs et al. |
| 5,036,045 A | 7/1991 | Thorner |
| RE33,699 E | 9/1991 | Drengler |
| 5,061,690 A | 10/1991 | Kann et al. |
| 5,084,442 A | 1/1992 | Felix et al. |
| 5,134,210 A | 7/1992 | Edwards |
| 5,137,872 A | 8/1992 | Seely et al. |
| 5,292,721 A | 3/1994 | Boyd et al. |
| 5,439,440 A | 8/1995 | Hofmann |
| 5,486,505 A | 1/1996 | Bowers et al. |
| 5,696,089 A | 12/1997 | Felix et al. |
| 5,702,359 A | 12/1997 | Hofmann et al. |
| 5,756,264 A | 5/1998 | Schwartz et al. |
| 5,776,901 A | 7/1998 | Bowers et al. |
| 5,792,747 A | 8/1998 | Schally et al. |
| 5,846,936 A | 12/1998 | Felix et al. |
| 5,847,066 A | 12/1998 | Coy et al. |

| | | | |
|---|---|---|---|
| 2005/0182014 A1* | 8/2005 | Draghia-Akli et al. | 514/44 |

FOREIGN PATENT DOCUMENTS

| | | | |
|---|---|---|---|
| EP | 1260229 A2 * | 11/2002 | |
| WO | WO/95/19805 | 7/1995 | |
| WO | WO/96/12006 | 4/1996 | |
| WO | WO/96/12520 | 5/1996 | |
| WO | WO/97/07826 | 3/1997 | |
| WO | WO 2004067719 A2 * | 8/2004 | |

OTHER PUBLICATIONS

Acsadi, G., G. Dickson, D. R. Love, A. Jani, F. S. Walsh, A. Gurusinghe, Wolff, JA, and K. E. Davies. 1991. Human dystrophin expression in mdx mice after intramuscular injection of DNA constructs. Nature 352:815-818.

Aihara, H. and J. Miyazaki. 1998. Gene transfer into muscle by electroporation in vivo. Nat. Biotechnol. 16:867-870.

Almendro, N., T. Bellon, C. Rius, P. Lastres, C. Langa, A. Corbi, and C. Bernabeu. 1996. Cloning of the human platelet endothelial cell adhsion molecule-1 promoter and its tissue-specific expression. Structural and functional characterization. J. Immunol. 157:5411-5421.

Aratani, Y., R. Okazaki, and H. Koyama. 1992. End extension repair of introduced targeting vectors mediated by homologous recombination in mammalian cells. Nucleic Acids Res. 20:4795-4801.

Argente, J., J. Pozo, and J. A. Chowen. 1996. The growth hormone axis: control and effects. Hormone Research 45 Suppl 1:9-11.

Arvan, P. and D. Castle, 1998. Sorting and storage during secretory granule biogenesis: looking backward and looking forward. Biochem. J. 332:593-610.

Babiuk, L. A., R. Pontarollo, S. Babiuk, B. Loehr, and van Drunen Littel-van den Hurk. 2003. Induction of immune responses by DNA vaccines in large animals. Vaccine 21:649-658.

Baertschi, A. J., D. Monnier, U. Schmidt, E. S. Levitan, S. Fakan, andA. Roatti, 2001. Acid prohormone sequence determines size, shape, and docking of secretory vesicles in atrial myocytes. Circ. Res. 89:E23-E29.

Baum, B. J., M. E. Berkman, Y. Marmary, C. M. Goldsmith, L. Baccaglini, S. Wang, R. B. Wellner, A. T. Hoque, J. C. Atkinson, H. Yamagishi, H. Kagami, A. F. Parlow, and J. Chao. 1999. Polarized secretion of transgene products from salivary glands in vivo. Hum. Gene Ther. 20;10:2789-2797.

Bercu, B. B. and R. F. Walker. 1997. Growth Hormone Secretagogues in Children With Altered Growth. Acta Paediatrica 86:102-106.

(Continued)

*Primary Examiner*—Fereydoun G Sajjadi
(74) *Attorney, Agent, or Firm*—Pepper Hamilton, LLP

(57) ABSTRACT

One aspect of the current invention is a method designing and using species-specific or synthetic signal peptides and GHRH sequences for the purpose of preventing and/or treating chronic illness in a subject by utilizing methodology that administers a single dose of nucleic acid expression vector or nucleic acid expression construct encoding a GHRH or functional biological equivalent to a subject through a parenteral route of administration.

13 Claims, 17 Drawing Sheets

OTHER PUBLICATIONS

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Blethen, S. L. and A. C. Rundle. 1996. Slipped capital femoral epiphysis in children treated with growth hormone. A summary of the National Cooperative Growth Study experience. Horm. Res. 46:113-116.

Bohlen, P., F. Esch, P. Brazeau, N. Ling, and R. Guillemin. 1983. Isolation and characterization of the porcine hypothalamic growth hormone releasing factor. Biochem. Biophys. Res. Commun. 116:726-734.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Breslin, M. B., I. Lindberg, S. Benjannet, J. P. Mathis, C. Lazure, and N. G. Seidah. 1993. Differential processing of proenkephalin by prohormone convertases 1(3) and 2 and furin. J. Biol. Chem. 268:27084-27093.

Butler, A. A., G. R. Ambler, B. H. Breier, D. LeRoith, C. T. Roberts, Jr., and P. D. Gluckman. 1994. Growth hormone (GH) and insulin-like growth factor-I (IGF-I) treatment of the GH-deficient dwarf rat: differential effects on IGF-I transcription start site expression in hepatic and extrahepatic tissues and lack of effect on type I IGF receptor mRNA expression. Mol. Cell Endocrinol. 101:321-330.

Carbonelli, D. L., E. Corley, M. Seigelchifer, and J. Zorzopulos. 1999. A plasmid vector for isolation of strong promoters in *Escherichia coli*. FEMS Microbiol. Lett. 177:75-82.

Caroni, P. and C. Schneider, 1994. Signaling by insulin-like growth factors in paralyzed skeletal muscle: rapid induction of IGF1 expression in muscle fibers and prevention of interstitial cell proliferation by IGF-BP5 and IGF-BP4. J. Neurosci. 14:3378-3388.

Castle, A. M. and J. D. Castle. 1998. Enhanced glycosylation and sulfation of secretory proteoglycans is coupled to the expression of a basic secretory protein. Mol. Biol. Cell 9:575-583.

Castle, A. M., A. Y. Huang, and J. D. Castle. 1998. Immunoglobulin-derived polypeptides enter the regulated secretory pathway in AtT-20 cells. FEBS Lett. %20;439:341-345.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U. S. A 94:3596-3601.

Chevalier, R. L., S. Goyal, A. Kim, A. Y. Chang, D. Landau, and D. LeRoith. 2000. Renal tubulointerstitial injury from ureteral obstruction in the neonatal rat is attenuated by IGF-1. Kidney Int. 57:882-890.

Cocea, L. 1997. Duplication of a region in the multiple cloning site of a plasmid vector to enhance cloning-mediated addition of restriction sites to a DNA fragment. Biotechniques 23:814-816.

Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-1 levels in old men. Journal of Clinical Endocrinology & Metabolism 76:134-138.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.

Danko, I. and J. A. Wolff. 1994. Direct gene transfer into muscle. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Dialynas, E., H. Brown-Borg, and A. Bartke. 1999. Immune function in transgenic mice overexpressing growth hormone (GH) releasing hormone, GH or GH antagonist. Proc. Soc. Exp. Biol. Med. 221:178-183.

Dolnik, V., M. Novotny, and J. Chmelik. 1993. Electromigration behavior of poly-(L-glutamate) conformers in concentrated polyacrylamide gels. Biopolymers 33:1299-1306.

Dorsch-Hasler, K., G. M. Keil, F. Weber, M. Jasin, W. Schaffner, and U. H. Koszinowski. 1985. A long and complex enhancer activates transcription of the gene coding for the highly abundant immediate early mRNA in murine cytomegalovirus. Proc. Natl. Acad. Sci. U. S. A 82:8325-8329.

Draghia-Akli, R., K. K. Cummings, A. S. Khan, P. A. Brown, and R. H. Carpenter. 2003a. Effects of plasmid-mediated growth hormone releasing hormone supplementation in young healthy Beagle dogs. Journal of Animal Science 81:2301-2310.

Draghia-Akli, R., K. M. Ellis, L. A. Hill, P. B. Malone, and M. L. Fiorotto. 2003b. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., K. A. Hahn, G. K. King, K. Cummings, and R. H. Carpenter. 2002a. Effects Of Plasmid Mediated Growth Hormone Releasing Hormone In Severely Debilitated Dogs With Cancer. Molecular Therapy 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technology in Cancer Research & Treatment 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Dubreuil, P., D. Petitclerc, G. Pelletier, P. Gaudreau, C. Farmer, Mowles, TF, and P. Brazeau. 1990. Effect of dose and frequency of administration of a potent analog of human growth hormone-releasing factor on hormone secretion and growth in pigs. Journal of Animal Science 68:1254-1268.

Duck, S. C., H. P. Schwarz, G. Costin, R. Rapaport, S. Arslanian, A. Hayek, M. Connors, and J. Jaramillo. 1992. Subcutaneous growth hormone-releasing hormone therapy in growth hormone-deficient children: first year of therapy. Journal of Clinical Endocrinology & Metabolism 75:1115-1120.

El Meskini, R., L. Jin, R. Marx, A. Bruzzaniti, J. Lee, R. Emeson, and R. Mains. 2001. A signal sequence is sufficient for green fluorescent protein to be routed to regulated secretory granules. Endocrinology 142:864-873.

Erikstrup, C., L. M. Pedersen, L. Heickendorff, T. Ledet, and L. M. Rasmussen. 2001. Production of hyaluronan and chondroitin sulphate proteoglycans from human arterial smooth muscle—the effect of glucose, insulin, IGF-I or growth hormone. Eur. J Endocrinol. 145:193-198.

Esch, F. S., P. Bohlen, N. C. Ling, P. E. Brazeau, W. B. Wehrenberg, M. O. Thorner, M. J. Cronin, and R. Guillemin. 1982. Characterization of a 40 residue peptide from a human pancreatic tumor with growth hormone releasing activity. Biochemical & Biophysical Research Communications 109:152-158.

Etherton, T. D., J. P. Wiggins, C. S. Chung, C. M. Evock, J. F. Rebhun, and P. E. Walton. 1986. Stimulation of pig growth performance by porcine growth hormone and growth hormone-releasing factor. Journal of Animal Science 63:1389-1399.

Evans, W. S., M. L. Vance, D. L. Kaiser, R. P. Sellers, J. L. Borges, T. R. Downs, L. A. Frohman, J. Rivier, W. Vale, and M. O. Thorner, 1985. Effects of intravenous, subcutaneous, and intranasal administration of growth hormone (GH)-releasing hormone-40 on serum GH concentrations in normal men. Journal of Clinical Endocrinology & Metabolism 61:846-850.

Fernandez, V. G., L. Cacicedo, M. J. Lorenzo, M. T. los Frailes, J. I. Lara, and F. F. Sanchez. 1994. Biosynthesis of growth hormone-releasing factor by fetal rat cerebrocortical and hypothalamic cells. Peptides 15:825-828.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Foncea, R., M. Andersson, A. Ketterman, V. Blakesley, M. Sapag-Hagar, P. H. Sugden, D. LeRolth, and S. Lavandero. 1997. Insulin-like growth factor-I rapidly activates multiple signal transduction pathways in cultured rat cardiac myocytes. J. Biol. Chem. 272:19115-19124.

Frohman, L. A., T. R. Downs, E. P. Heimer, and A. M. Felix. 1989. Dipeptidylpeptidase IV and trypsin-like enzymatic degradation of human growth hormone-releasing hormone in plasma. J. Clin. Invest. 83:1533-1540.

Frohman, L. A., J. L. Thominet, C. B. Webb, M. L. Vance, H. Uderman, J. Rivier, W. Vale, and M. O. Thorner. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and . 1995. The insulin gene promoter. A simplified nomenclature. Diabetes 44:1002-1004.

Gesundheit, N. and J. K. Alexander. 1995. Endocrine Therapy with Recombinant Hormones and Growth Factors. In: B. D. Weintraub (Ed.) Molecular Endocrinology: Basic Concepts and Clinical Correlations. pp. 491-507. Raven Press,Ltd., New York.

Gopinath, R. and T. D. Etherton. 1989a. Effects of porcine growth hormone on glucose metabolism of pigs: I. Acute and chronic effects on plasma glucose and insulin status. J. Anim Sci. 67:682-688.

Gopinath, R. and T. D. Etherton. 1989b. Effects of porcine growth hormone on glucose metabolism of pigs: II. Glucose tolerance, peripheral tissue insulin sensitivity and glucose kinetics. J. Anim Sci. 67:689-697.

Gramolini, A. O., G. Belanger, and B. J. Jasmin. 2001. Distinct regions in the 3' untranslated region are responsible for targeting and stabilizing utrophin transcripts in skeletal muscle cells. J Cell Biol. 154:1173-1183.

Guillemin, R., P. Brazeau, P. Bohlen, F. Esch, N. Ling, and W. B. Wehrenberg. 1982. Growth hormone-releasing factor from a human pancreatic tumor that caused acromegaly. Science 218:585-587.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Hoess, R. H. and K. Abremski. 1985. Mechanism of strand cleavage and exchange in the Cre-lox site-specific recombination system. J. Mol. Biol. 181:351-362.

Horlick, R. A. and P. A. Benfield. 1989. The upstream muscle-specific enhancer of the rat muscle creatine kinase gene is composed of multiple elements. Mol. Cell Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jardieu, P., R. Clark, D. Mortensen, and K. Dorshkind. 1994. In vivo administration of insulin-like growth factor-I stimulates primary B lymphopoiesis and enhances lymphocyte recovery after bone marrow transplantation. J. Immunol. 152:4320-4327.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:72-70.

Kallio, J., U. Pesonen, U. Jaakkola, M. K. Karvonen, H. Helenius, and M. Koulu. 2003. Changes in diurnal sympathoadrenal balance and pituitary hormone secretion in subjects with Leu7Pro polymorphism in the prepro-neuropeptide Y. J. Clin. Endocrinol. Metab 88:3278-3283.

Kallio, J., U. Pesonen, M. K. Karvonen, M. Kojima, H. Hosoda, K. Kangawa, and M. Koulu, 2001. Enhanced exercise-induced GH secretion in subjects with Pro7 substitution in the prepro-NPY. J. Clin. Endocrinol. Metab 86:5348-5352.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Kelly, R. B. 1985. Pathways of protein secretion in eukaryotes. Science 230:25-32.

Khan, A. S., I. W. Anscombe, K. K. Cummings, M. A. Pope, L. C. Smith, and R. Draghia-Akli. 2003a. Effects of plasmid-mediated growth hormone releasing hormone supplementation on LL-2 adenocarcinoma in mice. Mol. Ther. 8:459-466.

Khan, A. S., I. W. Anscombe, K. K. Cummings, M. A. Pope, L. C. Smith, and R. Draghia-Aklia. 2003b. Regulated plasmid-mediated growth hormone releasing hormone stimulation decreases tumor growth in nude mice. Am. J. Physiol. Endocrinol. Metab. In preparation.

Khorram, O., M. Garthwaite, and T. Golos. 2001. The influence of aging and sex hormones on expression of growth hormone-releasing hormone in the human immune system. J Clin. Endocrinol. Metab 86:3157-3161.

Klamut, H. J., L. O. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10:193-205.

Koo, G. C., C. Huang, R. Camacho, C. Trainor, J. T. Blake, A. Sirotina-Meisher, K. D. Schleim, T. J. Wu, K. Cheng, R. Nargund, and G. McKissick. 2001. Immune enhancing effect of a growth hormone secretagogue. J Immunol. 166:4195-4201.

Kooistra, H. S., G. Voorhout, J. A. Mol, and A. Rijnberk. 2000. Combined pituitary hormone deficiency in german shepherd dogs with dwarfism. Domest. Anim Endocrinol. 19:177-190.

Kooistra, H. S., G. Voorhout, P. J. Selman, and A. Rijnberk. 1998. Progestin-induced growth hormone (GH) production in the treatment of dogs with congenital GH deficiency. Domest. Anim Endocrinol. 15:93-102.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lapierre, H., G. Pelletier, D. Petitclerc, P. Dubreuil, J. Morisset, P. Gaudreau, Y. Couture, and P. Brazeau. 1991. Effect of human growth hormone-releasing factor and(or) thyrotropin-releasing factor on growth, carcass composition, diet digestibility, nutrient balance, and plasma constituents in dairy calves. Journal of Animal Science 69:587-598.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Lee, M. A., K. H. Cheong, D. Shields, S. D. Park, and S. H. Hong. 2002. Intracellular trafficking and metabolic turnover of yeast prepro-alpha-factor-SRIF precursors in GH3 cells. Exp. Mol. Med. 34:285-293.

Lee, S. H., W. Wang, S. Yajima, P. A. Jose, and M. M. Mouradian. 1997. Tissue-specific promoter usage in the D1A dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Milas, C. Charnsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Lin, H., K. E. Yutzey, and S. F. Konieczny. 1991. Muscle-specific expression of the troponin I gene requires Interactions between helix-loop-helix muscle regulatory factors and ubiquitous transcription factors. Mol. Cell Biol. 11:267-280.

Liu, J. L. and D. LeRoith. 1999. Insulin-like growth factor I is essential for postnatal growth in response to growth hormone. Endocrinology 140:5178-5184.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lowe, W. L., Jr., M. Adamo, H. Werner, C. T. Roberts, Jr., and D. LeRoith. 1989. Regulation by fasting of rat insulin-like growth factor I and its receptor. Effects on gene expression and binding. J. Clin. Invest 84:619-626.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Macchi, P., I. Hemraj, B. Goetze, B. Grunewald, M. Mallardo, and M. A. Kiebler. 2003. A GFP-based System to Uncouple mRNA Transport from Translation in a Single Living Neuron. Mol. Biol. Cell 14:1570-1582.

Macejak, D. G. and P. Sarnow. 1991. Internal initiation of translation mediated by the 5' leader of a cellular mRNA. Nature 353:90-94.

Martoglio, B. 2003. Intramembrane proteolysis and post-targeting functions of signal peptides. Biochem. Soc. Trans. 31:1243-1247.

Martoglio, B. and B. Dobberstein. 1998. Signal sequences: more than just greasy peptides. Trends Cell Biol. 8:410-415.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Moore, H. P. and R. B. Kelly. 1985. Secretory protein targeting in a pituitary cell line: differential transport of foreign secretory proteins to distinct secretory pathways. J. Cell Biol. 101:1773-1781.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Murray, R. D. and S. M. Shalet. 2000. Growth hormone: current and future therapeutic applications. Expert. Opin. Pharmacother. 1:975-990.

Naim, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhrmann, H. Liang, M. Oakley, A. Taye, B. K. Sim, and S. L. Hoffman. 2001. Codon optimization of gene fragments encoding Plasmodium falciparum merzoite proteins enhances DNA vaccine protein expression and immunogenicity in mice. Infect. Immun. 69:7250-7253.

Neumann, E., M. Schaefer-Ridder, Y. Wang, and P. H. Hofschneider. 1982. Gene transfer into mouse lyoma cells by electroporation in high electric fields. EMBO J. 1:841-845.

Nillni, E. A., R. Steinmetz, and O. H. Pescovitz. 1999. Post-translational processing of progrowth hormone-releasing hormone. Endocrinology 140:5817-5827.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Parks, J. S., R. W. Pfaffle, M. R. Brown, H. Abdul-Latif, and L. R. Meacham. 1995. Growth Hormone Deficiency. In: B. D. Weintraub (Ed.) Molecular Endocrinology: Basic Concepts and Clinical Correlations. pp. 473-490. Raven Press,Ltd., New York.

Parrizas, M. and D. LeRoith. 1997. Insulin-like growth factor-1 inhibition of apoptosis is associated with increased expression of the bcl-xL gene product. Endocrinology 138:1355-1358.

Pavasant, P., T. Shizari, and C. B. Underhill. 1996. Hyaluronan synthesis by epiphysial chondrocytes is regulated by growth hormone, insulin-like growth factor-1, parathyroid hormone and transforming growth factor-beta 1. Matrix Biol. 15:423-432.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potter, H., L. Weir, and P. Leder. 1984. Enhancer-dependent expression of human kappa immunoglobulin genes introduced into mouse pre-B lymphocytes by electroporation, Proc. Natl. Acad. Sci. U. S. A 81:7161-7165.

Prentice, H., R. A. Kloner, T. Prigozy, T. Christensen, L. Newman, Y. Li, and L. Kedes. 1994. Tissue restricted gene expression assayed by direct DNA injection into cardiac and skeletal muscle. Journal of Molecular & Cellular Cardiology 26:1393-1401.

Rabinovsky, E. D. and R. Draghia-Akli. 2004. Insulin-like Growth Factor I Plasmid Therapy Promotes in Vivo Angiogenesis. Mol. Ther. 9(1) 46-55.

Rabinovsky, E. D., G. M. Smith, D. P. Browder, H. D. Shine, and J. L. McManaman. 1992. Peripheral nerve injury down-regulates CNTF expression in adult rat sciatic nerves. J. Neurosci. Res. 31:188-192.

Rijnberk, A., H. van Herpen, J. A. Mol, and G. R. Rutteman. 1993. Disturbed release of growth hormone in mature dogs: a comparison with congenital growth hormone deficiency. Vet. Rec. 133:542-545.

Robbins, K., S. McCabe, T. Scheiner, J. Strasser, R. Clark, and P. Jardieu. 1994. Immunological effects of insulin-like growth factor-I--enhancement of immunoglobulin synthesis. Clin. Exp. Immunol. 95:337-342.

Satozawa, N., K. Takezawa, T. Miwa, S. Takahashi, M. Hayakawa, and H. Ooka. 2000. Differences in the effects of 20 K- and 22 K-hGH on water retention in rats. Growth Horm. IGF. Res. 10:187-192.

Schaner, P., R. B. Todd, N. G. Seidah, and E. A. Nillni. 1997. Processing of prothyrotropin-releasing hormone by the family of prohormone convertases. J. Biol. Chem. 272:19958-19968.

Skroch, P., C. Buchman, and M. Karin. 1993. Regulation of human and yeast metallothionein gene transcription by heavy metal ions. Prog. Clin. Biol. Res. 380:113-28.:113-128.

Smeekens, S. P., A. G. Montag, G. Thomas, C. Albiges-Rizo, R. Carroll, M. Benig, L. A. Phillips, S. Martin, S. Ohagi, P. Gardner, and . 1992. Proinsulin processing by the subtilisin-related proprotein convertases furin, PC2, and PC3. Proc. Natl. Acad. Sci. U. S. A 89:8822-8826.

Smith, L. C. and J. L. Nordstrom. 2000. Advances in plasmid gene delivery and expression in skeletal muscle. Curr. Opin. Mol. Ther. 2:150-154.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Tag, C. G., S. Mengsteab, C. Hellerbrand, F. Lammert, A. M. Gressner, and R. Weiskirchen. 2003. Analysis of the transforming growth factor-beta1 (TGF-beta1) codon 25 gene polymorphism by LightCycler-analysis in patients with chronic hepatitis C infection. Cytokine 24:173-181.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. Journal of Clinical Endocrinology & Metabolism 59:846-849.

Thorner, M. O., M. L. Hartman, M. L. Vance, S. S. Pezzoli, and E. J. Ampleford. 1995. Neuroendocrine regulation of growth hormone secretion. Neuroscience & Biobehavioral Reviews 19:465-468.

Thorner, M. O., M. L. Vance, W. S. Evans, A. D. Rogol, J. Rivier, W. Vale, Blizzard, and RM. 1986. Clinical studies with GHRH in man. Hormone Research 24:91-98.

Tollefsen, S., M. Vordermeier, I. Olsen, A. K. Storset, L. J. Reitan, D. Clifford, D. B. Lowrie, H. G. Wiker, K. Huygen, G. Hewinson, I. Mathiesen, and T. E. Tjelle. 2003. DNA injection in combination with electroporation: a novel method for vaccination of farmed ruminants. Scand. J Immunol. 57:229-238.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2(XI) collagen promoter. J. Biol. Chem. 273:22861-22864.

Tsunekawa, B., M. Wada, M. Ikeda, H. Uchida, N. Naito, and M. Honjo. 1999. The 20-kilodalton (kDa) human growth hormone (hGH) differs from the 22-kDa hGH in the effect on the human prolactin receptor. Endocrinology 140:3909-3918.

Tsurumi, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion [see comments]. Circulation 94:3281-3290.

T-ur-Kaspa, R., L. Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

van Rooij, E. M., B. L. Haagmans, H. L. Glansbeek, Y. E. de Visser, M. G. de Bruin, W. Boersma, and A. T. Bianchi. 2000. A DNA vaccine coding for glycoprotein B of pseudorabies virus induces cell-mediated immunity in pigs and reduces virus excretion early after infection. Vet. Immunol. Immunopathol. 74:121-136.

Vance, M. L. 1990. Growth-hormone-releasing hormone. Clinical Chemistry 36:415-420.

Vance, M. L., D. L. Kaiser, W. S. Evans, R. Furlanetto, W. Vale, J. Rivier, and M. O. Thorner. 1985. Pulsatile growth hormone secretion in normal man during a continuous 24-hour infusion of human growth hormone releasing factor (1-40). Evidence for intermittent somatostatin secretion. J. Clin. Invest. 75:1584-1590.

Veldhuis, J. D., A. Iranmanesh, and A. Weltman. 1997. Elements in the pathophysiology of diminished growth hormone (GH) secretion in aging humans. Endocrine 7:41-48.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stevenaert, and A. Beckers. 1997. Two years of replacement therapy in adults with growth hormone deficiency. Clin. Endocrinol. (Oxf) 47:485-494.

Vilquin, J. T., P. F. Kennel, M. Paturneau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Vittone, J., M. R. Blackman, J. Busby-Whitehead, C. Tsiao, K. J. Stewart, J. Tobin, T. Stevens, M. F. Bellantoni, M. A. Rogers, G. Baumann, J. Roth, S. M. Harman, and R. G. S. Spencer. 1997. Effects of single nightly injections of growth hormone-releasing hormone (GHRH 1-29) in healthy elderly men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-kilodalton (kDa) human growth hormone (hGH) differs from the 22-kDa hGH in the complex formation with cell surface hGH receptor and hGH-binding protein circulating in human plasma. Mol. Endocrinol. 12:146-156.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Wong, P. M., Q. Yuan, H. Chen, B. M. Sultzer, and S. W. Chung. 2001. A single point mutation at the 3'-untranslated region of Ran mRNA leads to profound changes in lipopolysaccharide endotoxin-mediated responses. J Biol. Chem. 276:33129-33138.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med: 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

Zhou, A. and R. E. Mains. 1994. Endoproteolytic processing of proopiomelanocortin and prohormone convertases 1 and 2 in neuroendocrine cells overexpressing prohormone convertases 1 or 2. J. Biol. Chem. 269:17440-17447.

PCT International Search Report and Written Opinion Dated Aug. 5, 2005, for PCT/US2005/000892.

* cited by examiner

Translation of GHRH species (LONG):

```
     bovine GHRH  (1) MVLWVFFLVTLTLSSGSHGSLPS-QPLRIPRYADAIFTNSYRKVLGQLSARKLLQDIMNRQQGERNQEQGA
      ovine GHRH  (1) MVLWVFFLVTLTLSSGSHGSLPS-QPLRIPRYADAIFTNSYRKILGQLSARKLLQDIMNRQQGERNQEQGA
        cat GHRH  (1) MVLWVFFLVILTLDSGSHCSPPS-LPLRMPRYADAIFTNSYRKVLGQLSARKLLQDIMSRQQGERNQEQGA
    chicken GHRH  (1) -MALWVFFVLLTLTSGSHCSLPPSPPFRVRRHADGIFSKAYRKLLGQLSARNYLHSLMAKRVGSGLGDEAEPLS
horse GHRH (partial) (1) MVLWVFFFVILTLSNSSHCSPPPPLTLRMRRYADAIFTNNYRKVLGQLSARKILQDIMSR------------
         HV-GHRH  (1) MVLWVFFFVILTLSNSSHCSPPPPLTLRMRRHVDAIFTNSYRKVLAQLSARKLLQDILNRQQGERNQEQGA---
         TI-GHRH  (1) MVLWVFFFVILTLSNSSHCSPPPPLTLRMRRYIDAIFTNSYRKVLAQLSARKLLQDILNRQQGERNQEQGA---
    wt-porcine GHRH (1) MVLWVFFFVILTLSNSSHCSPPPPLTLRMRRYADAIFTNSYRKVLGQLSARKLLQDIMSRQQGERNQEQGA---
        dog GHRH  (1) MVLWVFFLVILTLSSGSHSSPPS-LPIRIPRYADAIFTNSYRKVLGQLSARKLLQDIMSRQQGERNREQGA---
      human GHRH  (1) MPLWVFFFVILTLSNSSHCSPPPPLTLRMRRYADAIFTNSYRKVLGQLSARKLLQDIMSRQQGESNQERGA---
       Consensus  (1) MVLWVFF  VILTLSSGSHCSPP    LPLRM  RYADAIFTNSYRKVLGQLSARKLLQDIMSRQQGERNQEQGA
```

ENHANCED SECRETION/RETENTION OF GROWTH HORMONE RELEASING HORMONE (GHRH) FROM MUSCLE CELLS BY SPECIES-SPECIFIC SIGNAL PEPTIDE

RELATED APPLICATIONS

This application claims priority to U.S. Provisional Patent Application, Ser. No. 60/537,582, entitled "ENHANCED SECRETION/RETENTION OF GROWTH HORMONE RELEASING HORMONE (GHRH) FROM MUSCLE CELLS BY SPECIES-SPECIFIC SIGNAL PEPTIDE," filed on Jan. 20, 2004, having Ruxandra Draghia-Akli listed as the inventor, the entire content of which is hereby incorporated by reference.

BACKGROUND

This invention pertains to a method of producing and using species-specific or synthetic signal peptides and GHRH sequences for the purpose of preventing and/or treating chronic illness in a subject by utilizing methodology that administers a single dose of nucleic acid expression vector or nucleic acid expression construct encoding a GHRH or functional biological equivalent to a subject through a parenteral route of administration. More specifically, a method of expressing and secreting an encoded growth-hormone-releasing-hormone ("GHRH") peptide from a cell of a subject includes: delivering into the cell of the subject an isolated nucleic acid expression construct that encodes a signal peptide coupled to the encoded GHRH peptide. In a preferred embodiment, the encoded signal peptide is at least 90% identical to (SEQID No.: 52) and the encoded GHRH peptide is at least 90% identical to (SEQID No.: 14).

Signal Peptides: Many neuropeptides and neurotransmitters are first synthesized as large pro-protein precursors. After their synthesis in the rough endoplasmic reticulum ("RER"), these pro-hormones or pro-neurotransmitters are post-translationally modified to give rise to mature peptides that have unique biological actions. Limited endoproteolytic cleavage occurs at paired basic residues, either lysine-arginine or arginine-arginine, with cleavage at monobasic sites occurring less frequently (Schaner et al., 1997)

Secretion is constitutive if proteins are secreted at the same rates as they are synthesized (Kelly, 1985). In regulated secretion newly synthesized proteins destined for secretion are stored at high concentration in secretory vesicles until the cell receives an appropriate stimulus. When both constitutive and regulated protein secretion can take place in the same cell a mechanism must exist for sorting the correct secretory protein into the correct secretory vesicle. The secretory vesicle must then be delivered to the appropriate region of plasma membrane (Moore and Kelly, 1985). Numerous, more recent studies have suggested that protein secretion pathways are more complicated. Thus, constitutive secretory markers are not excluded from the regulated secretory pathway and that efficient sorting for regulated secretion occurs above a background of proteins which enter the granules without sorting (Castle et al., 1998). There is also good evidence that secretion for the regulated pathway may be passive, i.e. not involving an active sorting signal/receptor process. Rather, regulated pathway appears somewhat unrestricted, with retention in granules as a result of protein-protein interactions during the condensation of secretory vesicles (Arvan and Castle, 1998; Castle and Castle, 1998).

For many pro-hormones, serial processing occurs as they are targeted to the regulated secretory pathway. In the neuroendocrine system, it is believed that fully processed bioactive peptides are stored in secretory granules that are released only after ligand-specific stimulation of a membrane-bound receptor (Lee et al., 2002).

How vesicles are born in the trans-Golgi network and reach their docking sites at the plasma membrane is still largely unknown and is under current investigation. For example, in a study on live, primary cultured atrial cardiomyocytes, secretory vesicles are visualized by expressing fusion proteins of proatrial natriuretic peptide (proANP) and green fluorescent protein. The number of docked vesicles is significantly correlated with the number of mobile vesicles. The deletion of the acidic N-terminal or point mutations change size and shape-but not velocity-of the vesicles, and, strikingly, abolish their docking at the plasma membrane (Baertschi et al., 2001). The shapes thus change from spheres to larger, irregular floppy bags or vesicle trains. Deletion of the C-terminal, where the ANP and its disulfide bond reside, does not change size, shape, docking, or velocity of the mobile vesicles. The N-terminal acid calcium-binding sequence of pro-ANP is known to cause protein aggregation at the high calcium concentration prevailing in the trans-Golgi network. Therefore, these results indicate that amino acid residues favoring cargo aggregation are critically important in shaping the secretory vesicles and determining their fate-docking or not docking-at the plasma membrane.

Studies also assessed in vivo if transgene-encoded secretory proteins follow distinct, polarized sorting pathways as has been shown to occur "classically" in cell biological studies in vitro. For instance, recombinant adenoviruses were used to deliver different transgenes to a rat submandibular cell line in vitro or to rat submandibular glands in vivo. Subsequently, the secretory distribution of the encoded proteins was determined (Baum et al., 1999). Luciferase, which has no signal peptide, served as a cell-associated, negative control and was used to correct for any nonspecific secretory protein release from cells. The three remaining transgene products tested, human tissue kallikrein (hK1), human growth hormone (hGH), and human alpha1-antitrypsin (halpha1AT), were predominantly secreted (>96%) in vitro. Most importantly, in vivo, after a parasympathomimetic secretory stimulus, both hK1 and hGH were secreted primarily in an exocrine manner into saliva. Conversely, halpha1AT was predominantly secreted into the bloodstream, i.e., in an endocrine manner. The aggregate results are consistent with the recognition of signals encoded within the transgenes that result in specific patterns of polarized protein secretion from rat submandibular gland cells in vivo.

Signal sequences are the addresses of proteins destined for secretion. In eukaryotic cells, they mediate targeting to the endoplasmic reticulum membrane and insertion into the translocon. Thereafter, signal sequences are cleaved from the pre-protein and liberated into the endoplasmic reticulum membrane. It has been recently reported that some liberated signal peptides are further processed by the intramembrane-cleaving aspartic protease signal peptide peptidase. Cleavage in the membrane-spanning portion of the signal peptide promotes the release of signal peptide fragments from the lipid bilayer. Typical processes that include intramembrane proteolysis is the regulatory or signalling function of cleavage products. Likewise, signal peptide fragments liberated upon intramembrane cleavage may promote such post-targeting functions in the cell (Martoglio, 2003). All signal sequences contain a hydrophobic core region, but, despite this, they show great variation in both overall length and amino acid sequence. Recently, it has become clear that this variation allows signal sequences to specify different modes of targeting and membrane insertion and even to perform functions after being cleaved from the parent protein. It became apparent that signal sequences are not simply greasy peptides but sophisticated, multipurpose peptides containing a wealth of functional information (Martoglio and Dobberstein, 1998).

In many cases the signal sequence is sufficient to target the newly synthesized protein to the regulated secretory pathway, or to the constitutive pathway (El Meskini et al., 2001). Also, minute changes in the signal peptide can be associated with important physiological changes. For instance, a leucine 7 to proline (Leu7Pro) polymorphism in the signal peptide of neuropeptide Y (NPY), an important neurotransmitter in the central and peripheral nervous system, is associated with increased blood lipid levels, accelerated atherosclerosis, and diabetic retinopathy (Kallio et al., 2001; Kallio et al., 2003). Studies determined that subjects with the Leu7Pro have a significantly lower plasma NPY and norepinephrine concentrations, lower insulin concentrations, higher glucose concentrations, lower insulin-glucose ratio, and lower prolactin levels in plasma.

We documented that the choice of 3'UTR has a profound impact on the localization of the transgene product and its subsequent effects. This observation confirms other previously described models. For example, the addition of a full-length 3'-UTR of the Ca(2+)/calmodulin-dependent protein kinase II alpha after the stop codon of a transgene reading frame targets the reporter MRNA to dendrites of transfected fully polarized hippocampal neurons. This observation confirms that this sequence contains translational activation signals (Macchi et al., 2003). The utrophin 3'UTR is critical for targeting mRNAs to cytoskeleton-bound polysomes and for controlling transcript stability (Gramolini et al., 2001), and a single point mutation in the 3'UTR of Ran is responsible for the nuclear localization or a preferred initial cytoplasmic distribution of the molecule, leading to profound changes in lipopolysaccharide endotoxin-mediated responses (Wong et al., 2001). We showed that the skeletal alpha actin 3'UTR sequesters IGF-I to the muscle, resulting in high local expression levels of hIGF-I, with effects on both angiogenesis and muscle regeneration. By contrast, the GH 3'UTR mediates the releases of IGF-I to the circulation, with effects only on angiogenesis (Rabinovsky and Draghia-Akli, 2004). Therefore, the choice of the signal peptide, as the choice of the 3'UTR, is critical for localization of gene products, and its potential subsequent effects on tissues or organs.

There is a significant body of work describing the enzymes involved in the post-translational processing of many neuropeptides, including pro-opiomelanocortin (Zhou and Mains, 1994), pro-thyroid releasing hormone (Schaner et al., 1997), pro-insulin (Smeekens et al., 1992) and pro-enkephalin (Breslin et al., 1993). Some studies looked at the biosynthesis and post-translational processing of pro-growth hormone releasing hormone (pro-GHRH) (Nillni et al., 1999). After cloning the corresponding complementary DNAs, it was determined that the GHRH sequence is derived from the pre-pro-GHRH (amino acids 1-104) precursor after removal of the leader signal peptide, followed by two proteolytic cleavages, one at the N- and the other at the C-terminal regions of the pre-pro-GHRH. This reaction generates a biologically active GHRH (corresponding to amino acids 31-73 of the pre-pro-hormone) after removal of the basic residues (Nillni et al., 1999). Some studies support the concept that GHRH is released via a regulated secretory pathway. However, peptide could be found in the media even without stimulation, confirming the observation that peptide secretion from cells is a complex mechanism (Fernandez et al., 1994).

Nevertheless, until the present invention, there was no indication that the same hormone, in our case the GHRH, could be differently processed in different animal species, and that species-specific changes in the signal peptide are playing a role in the rate of peptide secretion from cells.

Growth Hormone Releasing Hormone ("GHRH") and Growth Hormone ("GH") Axis: To better understand utilizing GHRH plasmid mediated gene supplementation as a treatment of different conditions, and designing better plasmid vectors adapted for a particular condition or another, the mechanisms and current understanding of the GHRH/GH axis will be addressed. Although not wanting to be bound by theory, the central role of growth hormone ("GH") is controlling somatic growth in humans and other vertebrates. The physiologically relevant pathways regulating GH secretion from the pituitary are fairly well known. The GH production pathway is composed of a series of interdependent genes whose products are required for normal growth. The GH pathway genes include: (1) ligands, such as GH and insulin-like growth factor-I (IGF-D); (2) transcription factors such as prophet of pit 1, or prop 1, and pit 1: (3) agonists and antagonists, such as growth hormone releasing hormone (GHRH) and somatostatin (SS), respectively; and (4) receptors, such as GHRH receptor (GHRH-R) and the GH receptor (GH-R). These genes are expressed in different organs and tissues, including the hypothalamus, pituitary, liver, and bone. Effective and regulated expression of the GH pathway is essential for optimal linear growth, as well as homeostasis of carbohydrate, protein, and fat metabolism. GH synthesis and secretion from the anterior pituitary is stimulated by GHRH and inhibited by somatostatin, both hypothalamic hormones. GH increases production of IGF-I, primarily in the liver, and other target organs. IGF-I and GH, in turn, feedback on the hypothalamus and pituitary to inhibit GHRH and GH release. GH elicits both direct and indirect actions on peripheral tissues, the indirect effects being mediated mainly by IGF-I.

Several studies in different animal models and human have shown that GHRH has an immune stimulatory effect, both through stimulation of the GH axis and directly as an immune-modulator (Dialynas et al., 1999; Khorram et al., 2001). GH has been known to enhance immune responses, whether directly or through the IGF-I, induced by GH. Recently, a GH secretagogue (GHS), was found to induce the production of GH by the pituitary gland, but also determined a statistically significant increase in thymic cellularity and differentiation in old mice. When inoculated with a transplantable lymphoma cell line, EL4, the treated old mice showed statistically significant resistance to the initiation of tumors and the subsequent metastases. Generation of CTL to EL4 cells was also enhanced in the treated mice, suggesting that GHS has a considerable immune enhancing effect (Koo et al., 2001). Our studies showed mice with implanted tumors given a plasmid-mediated GHRH supplementation had reduced tumor growth, reduced number of metastasis, improved kidney function and no muscle atrophy, most probably due to a significant stimulation of the immune function (Khan et al., 2003a; Khan et al., 2003b). The immune function is also modulated by IGF-I, and there is evidence that macrophages are a rich source of IGF-I. The treatment of mice with recombinant IGF-I confirmed these observations as it increased the number of pre-B and mature B cells in bone marrow (Jardieu et al., 1994). The mature B cell remained sensitive to IGF-I as immunoglobulin production was also stimulated by IGF-I in vitro and in vivo (Robbins et al., 1994).

In aging mammals, the GHRH-GH-IGF-I axis undergoes considerable decrement with reduced GH secretion and IGF-I production, associated with a loss of skeletal muscle mass (sarcopenia), osteoporosis, arthritis, increased fat deposition and decreased lean body mass (Caroni and Schneider, 1994; Veldhuis et al., 1997). It has been demonstrated that the development of these changes can be offset by recombinant GH therapy. It has also been shown in culture, in vitro that the production of hyaluronan and condroitin sulphate proteoglycans is regulated by GH, IGF-I, and that these molecules may be of significant importance in the therapy of joint pathology (Erikstrup et al., 2001; Pavasant et al., 1996).

The production of recombinant proteins in the last 2 decades provided a useful tool for the treatment of many diverse conditions. For example, GH-deficiencies in short stature children, anabolic agent in burn, sepsis, and AIDS patients. However, resistance to GH action has been reported in malnutrition and infection. Clinically, GH replacement therapy is used widely in both children and the elderly. Current GH therapy has several shortcomings, however, including frequent subcutaneous or intravenous injections, insulin resistance and impaired glucose tolerance (Rabinovsky et al., 1992); children are also vulnerable to premature epiphyseal closure and slippage of the capital femoral epiphysis (Liu and LeRoith, 1999). A "slow-release" form of GH (from Genentech) has been developed that only requires injections every 14 days. However, this GH product appears to perturb the normal physiological pulsatile GH profile, and is also associated with frequent side effects.

In contrast, essentially no side effects have been reported for recombinant GHRH therapies. Extracranially secreted GHRH, as mature peptide or truncated molecules (as seen with pancreatic islet cell tumors and variously located carcinoids) are often biologically active and can even produce acromegaly (Esch et al., 1982; Thomer et al., 1984). Administration of recombinant GHRH to GH-deficient children or adult humans augments IGF-I levels, increases GH secretion proportionally to the GHRH dose, yet still invokes a response to bolus doses of recombinant GHRH (Bercu and Walker, 1997). Thus, GHRH administration represents a more physiological alternative of increasing subnormal GH and IGF-I levels (Corpas et al., 1993).

GH is released in a distinctive pulsatile pattern that has profound importance for its biological activity (Argente et al., 1996). Secretion of GH is stimulated by the GHRH, and inhibited by somatostatin, and both hypothalamic hormones (Thomer et al., 1995). GH pulses are a result of GHRH secretion that is associated with a diminution or withdrawal of somatostatin secretion. In addition, the pulse generator mechanism is timed by GH-negative feedback. Effective and regulated expression of the GH and IGF-I pathway is essential for optimal linear growth, homeostasis of carbohydrate, protein, and fat metabolism, and for providing a positive nitrogen balance (Murray and Shalet, 2000). Numerous studies in humans, sheep or pigs showed that continuous infusion with recombinant GHRH protein restores the normal GH pattern without desensitizing GHRH receptors or depleting GH supplies as this system is capable of feed-back regulation, which is abolished in the GH therapies (Dubreuil et al., 1990; Vance, 1990; Vance et al., 1985). Although recombinant GHRH protein therapy entrains and stimulates normal cyclical GH secretion with virtually no side effects, the short half-life of GHRH in vivo requires frequent (one to three times a day) intravenous, subcutaneous or intranasal (requiring 300-fold higher dose) administration. Thus, as a chronic treatment, GHRH administration is not practical.

Wild-type GHRH has a relatively short half-life in the circulatory system, both in humans (Frohman et al., 1984) and in farm animals. After 60 minutes of incubation in plasma 95% of the GHRH(1-44)NH2 is degraded, while incubation of the shorter (1-40)OH form of the hormone, under similar conditions, shows only a 77% degradation of the peptide after 60 minutes of incubation (Frohman et al., 1989). Incorporation of cDNA coding for a particular protease-resistant GHRH analog in a therapeutic nucleic acid vector results in a molecule with a longer half-life in serum, increased potency, and provides greater GH release in plasmid-injected animals (Draghia-Akli et al., 1999), herein incorporated by reference. Mutagenesis via amino acid replacement of protease sensitive amino acids prolongs the serum half-life of the GHRH molecule. Furthermore, the enhancement of biological activity of GHRH is achieved by using super-active analogs that may increase its binding affinity to specific receptors (Draghia-Akli et al., 1999).

Growth Hormone ("GH") and Growth Hormone Releasing Hormone ("GHRH") in Farm animals: The administration of recombinant growth hormone (GH) or recombinant GH has been used in subjects for many years, for use in domestic livestock. For example, administration of GHRH and GH stimulate milk production, with an increase in feed to milk conversion. This therapy enhances growth primarily by increasing lean body mass (Lapierre et al., 1991; van Rooij et al., 2000) with overall improvement in feed efficiency. Hot and chilled carcass weights are increased and carcass lipid (percent of soft-tissue mass) is decrease by administration of GHRH and GH (Etherton et al., 1986).

Although not wanting to be bound by theory, the linear growth velocity and body composition of humans, farm animals, and companion animals appear to respond to GH or GHRH replacement therapies under a broad spectrum of conditions. Similarly, anemia associated with different diseases and conditions can be treated by physiologically stimulating the GHRH axis (Draghia-Akli et al., 2002a; Draghia-Akli et al., 2003a). However, the etiology of these conditions can vary significantly. For example, in 50% of human GH deficiencies the GHRH-GH-IGF-I axis is functionally intact, but does not elicit the appropriate biological responses in its target tissues. Similar phenotypes are produced by genetic defects at different points along the GH axis (Parks et al., 1995), as well as in non-GH-deficient short stature. In humans, these non-GH-deficiency causes of short stature, such as Turner syndrome (Butler et al., 1994), hypochondroplasia (Foncea et al., 1997), Crohn's disease (Parrizas and LeRoith, 1997), intrauterine growth retardation (Hoess and Abremski, 1985) or chronic renal insufficiency (Lowe, Jr. et al., 1989) can be efficiently treated with GHRH or GH therapy (Gesundheit and Alexander, 1995). In companion animals, such as dogs or cats, there is little or no available therapy, and recombinant protein therapies have proved to be inefficient (Kooistra et al., 1998; Kooistra et al., 2000; Rijnberk et al., 1993).

Transgene Delivery and in vivo Expression: Although not wanting to be bound by theory, the delivery of specific transgenes to somatic tissue to correct inborn or acquired deficiencies and imbalances is possible. Such transgene-based drug delivery offers a number of advantages over the administration of recombinant proteins. These advantages include: the conservation of native protein structure; improved biological activity; avoidance of systemic toxicities; and avoidance of infectious and toxic impurities. Because the protein is synthesized and secreted continuously into the circulation, plasmid mediated therapy allows for prolonged production of the protein in a therapeutic range. Also, the use of the appropriate signal peptide to induce the release of the largest quantity possible per producing cell is of substantial importance. As shown, the localization of the newly synthesized gene product is essential for its biological activities. In contrast, the primary limitation of using recombinant protein is the limited availability of protein after each administration.

In a plasmid-based expression system, a non-viral transgene vector may comprise of a synthetic transgene delivery system in addition to the nucleic acid encoding the therapeutic genetic product. In this way, the risks associated with the use of most viral vectors can be avoided, including the expression of viral proteins that can induce immune responses against target tissues and the possibility of DNA mutations or activations of oncogenes. The non-viral expression vector products generally have low toxicity due to the use of "species-specific" components for gene delivery, which minimizes the risks of immunogenicity generally associated with viral vectors. Additionally, no integration of plasmid sequences into host chromosomes has been reported in vivo to date, so that this type of nucleic acid vector therapy should neither activate oncogenes nor inactivate tumor suppressor genes. As episomal systems residing outside the chromosomes, plasmids have defined pharmacokinetics and elimination profiles, leading to a finite duration of gene expression in target tissues.

Direct plasmid DNA gene transfer is currently the basis of many emerging nucleic acid therapy strategies and does not require viral components or lipid particles (Aihara and Miyazaki, 1998; Muramatsu et al., 2001). Skeletal muscle is target tissue, because muscle fiber has a long life span and can be transduced by circular DNA plasmids that are expressed in immunocompetent hosts (Davis et al., 1993; Tripathy et al., 1996). Plasmid DNA constructs are attractive candidates for direct therapy into the subjects skeletal muscle because the constructs are well-defined entities that are biochemically stable and have been used successfully for many years (Acsadi et al., 1991; Wolff et al., 1990). The relatively low expression levels of an encoded product that are achieved after direct plasmid DNA injection are sometimes sufficient to indicate bio-activity of secreted peptides (Danko and Wolff, 1994; Tsurumi et al., 1996). Previous reports demonstrated that human GHRH cDNA could be delivered to muscle by an injectable myogenic expression vector in mice where it transiently stimulated GH secretion to a modest extent over a period of two weeks (Draghia-Akli et al., 1997).

There are several different approaches that can be utilized for the treatment of chronic conditions as arthritis, cancer or kidney failure; effective treatment may require the presence of therapeutic agents for extended periods of time. In the case of proteins, this is problematic. Gene therapeutic approaches may offer a solution to this problem. Experimental studies have confirmed the feasibility, efficacy and safety of gene therapy for the treatment of animal models of chronic diseases.

Efforts have been made to enhance the delivery of plasmid DNA to cells by physical means including electroporation, sonoporation, and pressure. Although not wanting to be bound by theory, the administration of a nucleic acid construct by electroporation involves the application of a pulsed electric field to create transient pores in the cellular membrane without causing permanent damage to the cell, which allows exogenous molecules to enter the cell (Smith and Nordstrom, 2000). By adjusting the electrical pulse generated by an electroporetic system, nucleic acid molecules can travel through passageways or pores in the cell that are created during the procedure. U.S. Pat. No. 5,704,908 titled "Electroporation and iontophoresis catheter with porous balloon," issued on Jan. 6, 1998 with Hofmann et al., listed as inventors describes an electroporation apparatus for delivering molecules to cells at a selected location within a cavity in the body of a patient. Similar pulse voltage injection devices are also described in: U.S. Pat. No. 5,702,359 titled "Needle electrodes for mediated delivery of drugs and genes," issued on Dec. 30, 1997, with Hofiann, et al., listed as inventors; U.S. Pat. No. 5,439,440 titled "Electroporation system with voltage control feedback for clinical applications," issued on Aug. 8, 1995 with Hofinann listed as inventor; PCT application WO/96/12520 titled "Electroporetic Gene and Drug Therapy by Induced Electric Fields," published on May 5, 1996 with Hofinann et al., listed as inventors; PCT application WO/96/12006 titled "Flow Through Electroporation Apparatus and Method," published on Apr. 25, 1996 with Hofmann et al., listed as inventors; PCT application WO/95/19805 titled "Electroporation and Iontophoresis Apparatus and Method For insertion of Drugs and genes inot Cells," published on Jul. 27, 1995 with Hofmann listed as inventor; and PCT application WO/97/07826 titled "In Vivo Electroporation of Cells," published on Mar. 6, 1997, with Nicolau et al., listed as inventors, the entire content of each of the above listed references is hereby incorporated by reference.

Recently, significant progress to enhance plasmid delivery in vivo and subsequently to achieve physiological levels of a secreted protein was obtained using the electroporation technique. Electroporation has been used very successfully to transfect tumor cells after injection of plasmid (Lucas et al., 2002; Matsubara et al., 2001)) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Previous studies using GHRH showed that plasmid therapy with electroporation is scalable and represents a promising approach to induce production and regulated secretion of proteins in large animals and humans (Draghia-Akli et al., 1999; Draghia-Akli et al., 2002c). Electroporation also has been extensively used in rodents and other small animals (Bettan et al., 2000; Yin and Tang, 2001). Intramuscular injection of plasmid followed by electroporation has been used successfully in ruminants for vaccination purposes (Babiuk et al., 2003; Tollefsen et al., 2003). It has been observed that the electrode configuration affects the electric field distribution, and subsequent results (Gehl et al., 1999; Miklavcic et al., 1998). Although not wanting to be bound by theory, needle electrodes give consistently better results than external caliper electrodes in a large animal model.

The ability of electroporation to enhance plasmid uptake into the skeletal muscle has been well documented. Similarly, plasmids formulated with poly-L-glutamate ("PLG") or polyvinylpyrrolidone ("PVP") were observed to have an increase in plasmid transfection, which consequently increased the expression of a desired transgene. For example, plasmids formulated with PLG or PVP were observed to increase gene expression to up to 10 fold in the skeletal muscle of mice, rats, and dogs (Fewell et al., 2001; Mumper et al., 1998). Although not wanting to be bound by theory, the anionic polymer sodium PLG enhances plasmid uptake at low plasmid concentrations and reduces any possible tissue damage caused by the procedure. PLG is a stable compound and it is resistant to relatively high temperatures (Dolhik et al., 1993). PLG has been used to increase stability of anti-cancer drugs (Li et al., 2000) and as "glue" to close wounds or to prevent bleeding from tissues during wound and tissue repair (Otani et al., 1996; Otani et al., 1998). PLG has been used to increase stability in vaccine preparations (Matsuo et al., 1994) without increasing their immunogenicity. PLG also has been used as an anti-toxin after antigen inhalation or exposure to ozone (Fryer and Jacoby, 1993).

Although not wanting to be bound by theory, PLG increases the transfection of the plasmid during the electroporation process, not only by stabilizing the plasmid DNA and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, a process that substantially increases the transfection efficiency. Furthermore, PLG will prevent the muscle damage associated with in vivo plasmid delivery (Draghia-Akli et al., 2002b) and will increase plasmid stability in vitro prior to injection. There are studies directed to electroporation of eukaryotic cells with linear DNA (McNally et al., 1988; Neumann et al., 1982) (Toneguzzo et al., 1988) (Aratani et al., 1992; Nairn et al., 1993; Xie and Tsong, 1993; Yorifuji and Mikawa, 1990), but these examples illustrate transfection into cell suspensions, cell cultures, and the like, and such transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

Although not wanting to be bound by theory, a GHRH cDNA can be delivered to muscle of mice and humans by an injectable myogenic expression vector where it can transiently stimulate GH secretion over a period of two weeks (Draghia-Akli et al., 1997). This injectable vector system was optimized by incorporating a powerful synthetic muscle promoter (Li et al., 1999) coupled with a novel protease-resistant GHRH molecule with a substantially longer half-life and greater GH secretory activity (pSP-HV-GHRH) (Draghia-Akli et al., 1999). Highly efficient electroporation technology was optimized to deliver the nucleic acid construct to the skeletal muscle of an animal (Draghia-Akli et al., 2002b). Using this combination of vector design and electric pulses plasmid delivery method, the inventors were able to show increased growth and favorably modified body composition in pigs (Draghia-Akli et al., 1999; Draghia-Akli et al., 2003b) and rodents (Draghia-Akli et al., 2002c). The modified GHRH nucleic acid constructs increased red blood cell production in companion animals with cancer and cancer treatment-associated anemia (Draghia-Akli et al., 2002a). In pigs, available data suggested that the modified porcine HV-GHRH analog (SEQID No.: 1) was more potent in promoting growth and positive body composition changes than the wild-type porcine GHRH (Draghia-Akli et al., 1999).

Administering novel GHRH analog proteins (U.S. Pat Nos. 5,847,066; 5846,936; 5,792,747; 5,776,901; 5,696,089; 5,486,505; 5,137,872; 5,084,442; 5,036,045; 5,023,322; 4,839,344; 4,410,512, RE33,699) or synthetic or naturally occurring peptide fragments of GHRH (U.S. Pat. Nos. 4,833, 166; 4,228,158; 4,228,156; 4,226,857; 4,224,316; 4,223,021; 4,223,020; 4,223,019) for the purpose of increasing release of growth hormone have been reported. A GHRH analog containing the following mutations have been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. Pat. No. 6,551,996 titled "Super-active porcine growth hormone releasing hormone analog," issued on Apr. 22, 2003 with Schwartz, et al., listed as inventors ("the '996 Patent"), which teaches application of a GHRH analog containing mutations that improve the ability to elicit the release of growth hormone. In addition, the '996 Patent application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference.

U.S. Pat. No. 5,874,534 ("the '534 patent") and U.S. Pat. No. 5,935,934 ("the '934 patent") describe mutated steroid receptors, methods for their use and a molecular switch for nucleic acid vector therapy, the entire content of each is hereby incorporated by reference. A molecular switch for regulating expression in nucleic acid vector therapy and methods of employing the molecular switch in humans, animals, transgenic animals and plants (e.g. GeneSwitch®) are described in the '534 patent and the '934 patent. The molecular switch is described as a method for regulating expression of a heterologous nucleic acid cassette for nucleic acid vector therapy and is comprised of a modified steroid receptor that includes a natural steroid receptor DNA binding domain attached to a modified ligand binding domain. The modified binding domain usually binds only non-natural ligands, antihormones or non-native ligands. One skilled in the art readily recognizes natural ligands do not readily bind the modified ligand-binding domain and consequently have very little, if any, influence on the regulation or expression of the gene contained in the nucleic acid cassette.

In summary, the design of species-specific plasmid vectors encoding for GHRH or other proteins or peptides, for the therapy or prevention of chronic diseases in animals, were previously uneconomical and restricted in scope. The related art has shown that it is possible to improve these different conditions in a limited capacity utilizing recombinant protein technology, but these treatments have some significant drawbacks. It has also been taught that nucleic acid expression constructs that encode recombinant proteins are viable solutions to the problems of frequent injections and high cost of traditional recombinant therapy. There is a need in the art to expanded treatments for subjects with a disease by utilizing nucleic acid expression constructs that are delivered into a subject and express stable therapeutic proteins in vivo.

SUMMARY

One aspect of the current invention is a method to produce species-specific plasmid vectors by using different molecular tools, in particular, incorporating species-specific or strong synthetic signal peptides to be used for the treatment or prevention of chronic diseases. The method generally comprises delivering into the tissue of a farm animal a nucleic acid expression construct that encodes a growth-hormone-releasing-hormone ("GHRH") or functional biological equivalent thereof. Specific embodiments of this invention encompass various modes of delivering, expressing, and secreting an encoded GHRH from the tissue of the humans or farm animals using a nucleic acid expression construct (e.g. an electroporation method, a viral vector, in conjunction with a carrier, by parenteral route, or a combination thereof). In one preferred embodiment, the nucleic acid expression construct is delivered via an electroporation method comprising: a) penetrating the tissue in the animal or human with a plurality of needle electrodes, wherein the plurality of needle electrodes are arranged in a spaced relationship; b) introducing the optimized nucleic acid expression construct into the tissue between the plurality of needle electrodes; and c) applying an electrical pulse to the plurality of needle electrodes. Another preferred embodiment includes the optimized nucleic acid expression construct being delivered in a single dose, and the single dose comprising a total of about a 0.01-10 mg of the optimized nucleic acid expression construct. Generally, the optimized nucleic acid expression construct is delivered into a tissue of the animals or humans comprising diploid cells (e.g. muscle cells). In yet another specific embodiment the nucleic acid expression construct used for expressing and secreting GHRH is embodied in plasmid having at least 90% identity to pAV0244 (SEQID No.: 63) or at least 90% identity to pAV0244 (SEQID No.: 64). Other specific embodiments utilize other nucleic acid expression constructs having at least 90% identity to: an optimized bovine GHRH plasmid, pAV0236 (SEQID No.: 28); a TI-GHRH plasmid, pAV0239 (SEQID No.: 30); wt-porcine GHRH plasmid, pAV0225 (SEQID No.: 26); ovine GHRH plasmid, pAV0240 (SEQID No.: 31); chicken GHRH plasmid, pAV0241 (SEQID No.: 32); dog GHRH plasmid, pAV0235 (SEQID No.: 27); cat GHRH plasmid, pAV0238 (SEQID No.: 29); horse GHRH plasmid, pAV0249 (SEQID No.: 33); improved wild-type porcine GHRH plasmid, pAV0242 (SEQID No.: 61); human GHRH plasmid, pAV0243 (SEQID No.: 62); synthetic RPRP-GHRH plasmid, pAV0244 (SEQID No.: 63); or synthetic RPPP-GHRH plasmid, pAV0245 (SEQID No.: 64). In a fourth specific embodiment, the nucleic acid expression construct further comprises, a transfection-facilitating polypeptide (e.g. a charged polypeptide, or poly-L-glutamate). After delivering the optimized nucleic acid expression construct into the tissues of the animals or humans, expression of the encoded GHRH or functional biological equivalent thereof is initiated. Cellular trafficking and secretion is determined by the signal peptide used in the plasmid design. In a fifth specific embodiment, species—specific and synthetic signal peptides are described, and showed to impact dramatically the production and secretion of the transgene product, in our case GHRH. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQ ID No.: 14). The animal comprises a human, a food animal, a work animal (e.g. a pig, cow, sheep, goat or chicken), or a pet (e.g. horse, dog, cat).

BRIEF DESCRIPTION OF THE DRAWINGS

FIG. 11 shows the translation and consensus sequence of different species GHRH. SEQ ID NO:65 is bovine GHRH. SEQ ID NO:66 is ovine GHRH. SEQ ID NO:67 is cat GHRH. SEQ ID NO:68 is chicken GHRH. SEQ ID NO:69 is horse GHRH (partial). SEQ ID NO:70 is HV-GHRH. SEQ ID NO:71 is TI GHRH. SEQ ID NO:72 is wt-porcine GHRH. SEQ ID NO:73 is dog GHRH. SEQ ID NO:74 is human GHRH. SEQ ID NO:75 is consensus sequence 1 of GHRH. SEQ ID NO:76 is consensus sequence 2 of GHRH. SEQ ID NO:77 is consensus sequence 3 of GHRH. SEQ ID NO:78 is consensus sequence 4 of GHRH.

DETAILED DESCRIPTION OF THE PREFERRED EMBODIMENTS

Figure 1:
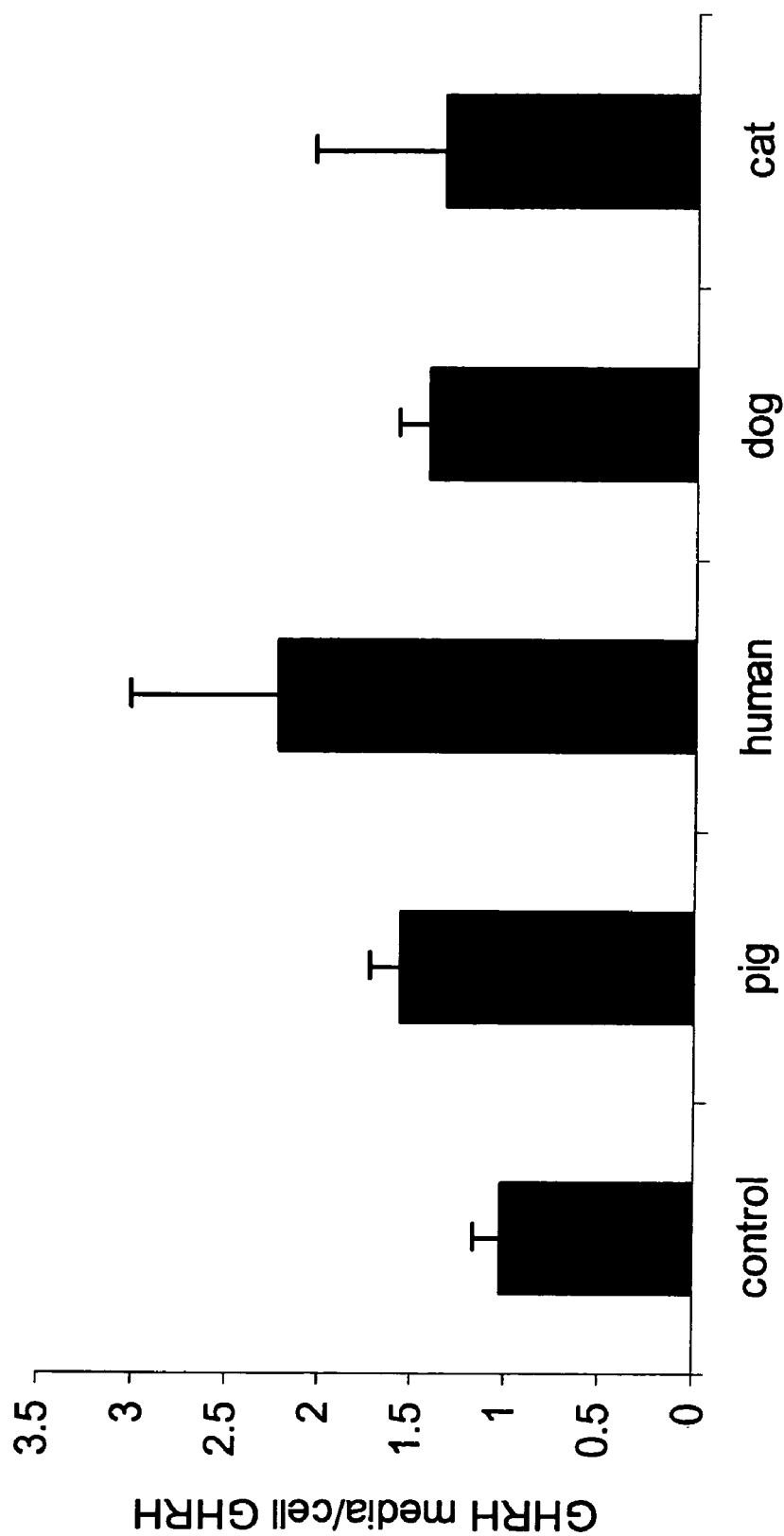
FIG. 1 shows the relative proportion of GHRH secreted from muscle cells and present into the culture media, and intracellular GHRH, as measured by specific radio-immunoassay.
Figure 2:
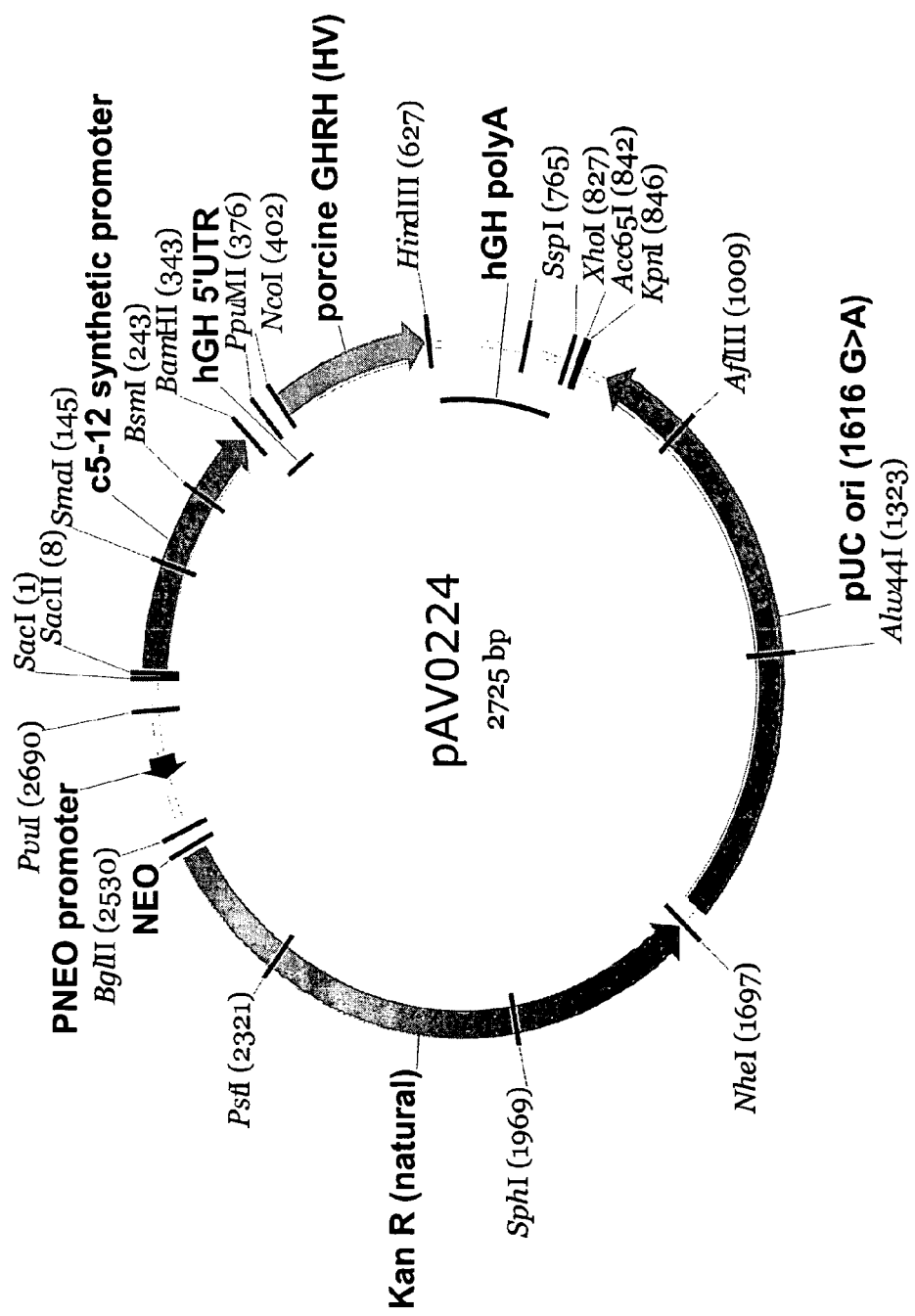
FIG. 2 shows a restriction map of pAV0224 expression plasmid.

It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "analog" as used herein includes any mutant of GHRH, or synthetic or naturally occurring peptide fragments of GHRH, such as HV-GHRH (SEQID No.: 1), pig-GHRH (SEQID No.: 2), bovine-GHRH (SEQID No.: 3), dog-GHRH (SEQID No.: 4), cat-GHRH (SEQID No.: 5), TI-GHRH (SEQID No.: 6), ovine-GHRH (SEQID No.: 7), chicken-GHRH (SEQID No.: 8), horse-GHRH (SEQID No.: 9), TV-GHRH (SEQID No.: 11), 15/27/28-GHRH (SEQID No.: 12), (1-44) NH$_2$ (SEQID No.: 13), (1-40)OH (SEQID No.: 10) forms, or any shorter form to no less than (1-29) amino acids.

The term "arthritis" as used herein is defined as a debilitating, chronic, systemic disease of unknown etiology that causes destruction of joint cartilage and bone. In humans, it generally occurs between the fourth and sixth decades of life, but juvenile forms are also common. It is characterized by joint stiffness, pain, and swelling, and is accompanied by a loss of body cell mass or cachexia that predominates in skeletal muscle, but also occurs in the viscera and immune system.

The term "bodily fat proportion" as used herein is defined as the body fat mass divided by the total body weight.

The term "body condition score" (BCS) as used herein is defined as a method to evaluate the overall nutrition and management of horses or any other farm animal.

The term "cassette" as used herein is defined as one or more transgene expression vectors.

The term "cell-transfecting pulse" as used herein is defined as a transmission of a force which results in transfection of a vector, such as a linear DNA fragment, into a cell. In some embodiments, the force is from electricity, as in electroporation, or the force is from vascular pressure.

The term "coding region" as used herein refers to any portion of the DNA sequence that is transcribed into messenger RNA (MRNA) and then translated into a sequence of amino acids characteristic of a specific polypeptide.

The term "Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 15%, more typically less than 5%, and even more typically less than 1%) in an encoded sequence are "conservatively modified variations" where the alterations result in the substitution of an amino acid with a chemically similar amino acid. Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "delivery" or "delivering" as used herein is defined as a means of introducing a material into a tissue, a subject, a cell or any recipient, by means of chemical or biological process, injection, mixing, electroporation, sonoporation, or combination thereof, either under or without pressure.

The term "DNA fragment" or "nucleic acid expression construct" as used herein refers to a substantially double stranded DNA molecule. Although the fragment may be generated by any standard molecular biology means known in the art, in some embodiments the DNA fragment or expression construct is generated by restriction digestion of a parent DNA molecule. The terms "expression vector," "expression cassette," or "expression plasmid" can also be used interchangeably. Although the parent molecule may be any standard molecular biology DNA reagent, in some embodiments the parent DNA molecule is a plasmid.

The term "chronically ill" or "chronic disease" as used herein is defined as patients with conditions as chronic obstructive pulmonary disease, chronic heart failure, stroke, dementia, rehabilitation after hip fracture, chronic renal failure, rheumatoid arthritis, and multiple disorders in the elderly, with doctor visits and/or hospitalization once a month for at least two years.

The term "donor-subject" as used herein refers to any species of the animal kingdom wherein cells have been removed and maintained in a viable state for any period of time outside the subject.

The term "donor-cells" as used herein refers to any cells that have been removed and maintained in a viable state for any period of time outside the donor-subject.

The term "electroporation" as used herein refers to a method that utilized electric pulses to deliver a nucleic acid sequence into cells.

The terms "electrical pulse" and "electroporation" as used herein refer to the administration of an electrical current to a tissue or cell for the purpose of taking up a nucleic acid molecule into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded GHRH" as used herein is a biologically active polypeptide of growth hormone releasing hormone.

The term "functional biological equivalent" of GHRH as used herein is a polypeptide that has a distinct amino acid sequence from a wild type GHRH polypeptide while simultaneously having similar or improved biological activity when compared to the GHRH polypeptide. The functional biological equivalent may be naturally occurring or it may be modified by an individual. A skilled artisan recognizes that the similar or improved biological activity as used herein refers to facilitating and/or releasing growth hormone or other pituitary hormones. A skilled artisan recognizes that in some embodiments the encoded functional biological equivalent of GHRH is a polypeptide that has been engineered to contain a distinct amino acid sequence while simultaneously having similar or improved biological activity when compared to the GHRH polypeptide. Methods known in the art to engineer such a sequence include site-directed mutagenesis or polymerase chain reaction (PCR).

The term "GeneSwitch®" (a registered trademark of Valentis, Inc.; Burlingame, Calif.) as used herein refers to the technology of a mifepristone-inducible heterologous nucleic acid sequences encoding regulator proteins, GHRH, biological equivalent or combination thereof. A skilled artisan recognizes that antiprogesterone agent alternatives to mifepristone are available, including onapristone, ZK112993, ZK98734, and 5α pregnane-3,2-dione.

The term "growth hormone" (GH) as used herein is defined as a hormone that relates to growth and acts as a chemical messenger to exert its action on a target cell. In a specific embodiment, the growth hormone is released by the action of growth hormone releasing hormone.

The term "growth hormone releasing hormone" (GHRH) as used herein is defined as a hormone that facilitates or stimulates release of growth hormone, and in a lesser extent other pituitary hormones, such as prolactin.

The term "heterologous nucleic acid sequence" as used herein is defined as a DNA sequence comprising differing regulatory and expression elements.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11-17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

The term "immunotherapy" as used herein refers to any treatment that promotes or enhances the body's immune system to build protective antibodies that will reduce the symptoms of a medical condition and/or lessen the need for medications.

The term "modified cells" as used herein is defined as the cells from a subject that have an additional nucleic acid sequence introduced into the cell.

The term "modified-donor-cells" as used herein refers to any donor-cells that have had a GHRH-encoding nucleic acid sequence delivered.

The term "molecular switch" as used herein refers to a molecule that is delivered into a subject that can regulate transcription of a gene.

The term "nucleic acid expression construct" as used herein refers to any type of genetic construct comprising a nucleic acid coding for a RNA capable of being transcribed. The term "expression vector" can also be used interchangeably herein. In specific embodiments, the nucleic acid expression construct comprises: a promoter; a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter.

The term "operatively linked" as used herein refers to elements or structures in nucleic acid sequences that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The terms "percentage of sequence identity" as used herein compares two optimally aligned sequences over a comparison window, wherein the portion of the sequence in the comparison window may comprise additions or deletions (i.e. "gaps") as compared to a reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence. Although not wanting to be bound by theory, computer software packages such as GAP, BESTFIT, BLASTA, FASTA and TFASTA can also be utilized to determine sequence identity.

The term "poly-L-glutamate ("PLG")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette that contains heterologous nucleic acid sequence encoding GHRH or a biological equivalent thereof into the cells of the subject and allowing expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid-mediated gene supplementation" as used herein refers a method to allow a subject to have prolonged exposure to a therapeutic range of a therapeutic protein by utilizing a nucleic acid-expression construct in vivo.

The term "pulse voltage device," or "pulse voltage injection device" as used herein relates to an apparatus that is capable of causing or causes uptake of nucleic acid molecules into the cells of an organism by emitting a localized pulse of electricity to the cells. The cell membrane then destabilizes, forming passageways or pores. Conventional devices of this type are calibrated to allow one to select or adjust the desired voltage amplitude and the duration of the pulsed voltage. The primary importance of a pulse voltage device is the capability of the device to facilitate delivery of compositions of the invention, particularly linear DNA fragments, into the cells of the organism.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1999; Darquet et al., 1997; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and an origin of replication.

The term "residual linear plasmid backbone" as used herein comprises any fragment of the plasmid backbone that is left at the end of the process making the nucleic acid expression plasmid linear.

The term "recipient-subject" as used herein refers to any species of the animal kingdom wherein modified-donor-cells can be introduced from a donor-subject.

The term "regulator protein" as used herein refers to any protein that can be used to control the expression of a gene, and that is increasing the rate of transcription in response to an inducing agent.

The term "secretagogue" as used herein refers to an agent that stimulates secretion. For example, a growth hormone secretagogue is any molecule that stimulates the release of growth hormone from the pituitary when delivered into an animal. Growth hormone releasing hormone is a growth hormone secretagogue.

The term "signal peptide" as used herein refers to the addresses of proteins destined for secretion. Most secreted proteins are first synthesized as large pro-protein precursors. After their synthesis in the rough endoplasmic reticulum (RER), these pro-proteins are post-translationally modified to give rise to mature peptides that have unique biological actions. In eukaryotic cells, signal peptides mediate targeting to the RER membrane and insertion into the translocon. Thereafter, signal sequences are cleaved from the pro-protein or pre-pro-protein and liberated into the RER membrane. The signal peptides have a role in the newly synthesized protein secretion, and may elicit other endocrine/paracrine effects.

The terms "subject" or "animal" as used herein refers to any species of the animal kingdom. In preferred embodiments, it refers more specifically to humans and domesticated animals used for: pets (e.g. cats, dogs, etc.); work (e.g. horses, etc.); food (e.g. cows, chicken, fish, lambs, pigs, etc); and all others known in the art.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of linear DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a transgene, a poly(A) sequence, or a 3' or 5' UTR.

The term "transfects" as used herein refers to introduction of a nucleic acid into a eukaryotic cell. In some embodiments, the cell is not a plant tissue or a yeast cell.

The term "vector" as used herein refers to any vehicle that delivers a nucleic acid into a cell or organism. Examples include plasmid vectors, viral vectors, liposomes, or cationic lipids. The term also refers to a construction comprised of genetic material designed to direct transformation of a targeted cell by delivering a nucleic acid sequence into that cell. A vector may contain multiple genetic elements positionally and sequentially oriented with other necessary elements such that an included nucleic acid cassette can be transcribed and when necessary translated in the transfected cells. These elements are operatively linked. The term "expression vector" refers to a DNA plasmid that contains all of the information necessary to produce a recombinant protein in a heterologous cell.

The term "viral backbone" as used herein refers to a nucleic acid sequence that does not contain a promoter, a gene, and a 3' poly(A) signal or an untranslated region, but contain elements including, but not limited at site-specific genomic integration Rep and inverted terminal repeats ("ITRs") or the binding site for the tRNA primer for reverse transcription, or a nucleic acid sequence component that induces a viral immunogenicity response when inserted in vivo, allows integration, affects specificity and activity of tissue specific promoters, causes transcriptional silencing or poses safety risks to the subject.

The term "vascular pressure pulse" refers to a pulse of pressure from a large volume of liquid to facilitate uptake of a vector into a cell. A skilled artisan recognizes that the amount and duration of the vascular pressure pulse is dependent on the tissue, size, and overall health of the recipient animal, and furthermore knows how to determine such parameters empirically.

Design of efficient and powerful nucleic acid expression constructs for targeted gene delivery, in particular for secreted proteins or hormones, is an important challenge. One aspect of the current invention is a method of designing new nucleic acid expression constructs that encode secreted proteins, including signal peptide sequences adequate for the target application. The method generally comprises the design of a nucleic acid expression construct that encodes a growth-hormone-releasing-hormone ("GHRH") or functional biological equivalent thereof, including species-specific signal peptides, or modified synthetic signal sequences, adequate for each therapeutic application. Specific embodiments of this invention encompass various modes of delivering into a tissue of the subject a nucleic acid expression construct that encodes a growth-hormone-releasing-hormone ("GHRH") or functional biological equivalent thereof (e.g. an electroporation method, a viral vector, in conjunction with a carrier, by parenteral route, or a combination thereof). In a first preferred embodiment, the nucleic acid expression construct is delivered via an electroporation method comprising: a) penetrating the tissue in the subject with a plurality of needle electrodes, wherein the plurality of needle electrodes are arranged in a spaced relationship; b) introducing the nucleic acid expression construct into the tissue between the plurality of needle electrodes; and c) applying an electrical pulse to the plurality of needle electrodes. A second preferred embodiment includes the nucleic acid expression construct being delivered in a single dose, and the single dose comprising a total of about a 0.01-10 mg of nucleic acid expression construct. Generally the nucleic acid expression construct is delivered into a tissue of the subject comprising diploid cells (e.g. muscle cells). In a third specific embodiment the nucleic acid expression construct used for transfection comprises a HV-GHRH plasmid (SEQ ID No.: 25). Other specific embodiments utilize other nucleic acid expression constructs (e.g. an optimized bovine GHRH plasmid, pAV0236 (SEQ ID No.: 28); a TI-GHRH plasmid, pAV0239 (SEQ ID No.: 30); wt-porcine GHRH plasmid, pAV0225 (SEQ ID No.: 26); ovine GHRH plasmid, pAV0240 (SEQ ID No.: 31); chicken GHRH plasmid, pAV0241 (SEQ ID No.: 32); dog GHRH plasmid, pAV0235 (SEQ ID No.: 27); cat GHRH plasmid, pAV0238 (SEQ ID No.: 29); horse GHRH plasmid, pAV0249 (SEQ ID No.: 33); improved wild-type porcine GHRH plasmid, pAV0242 (SEQ ID No.: 61); human GHRH plasmid, pAV0243 (SEQ ID No.: 62); synthetic RPRP-GHRH plasmid, pAV0244 (SEQ ID No.: 63); or synthetic RPPP-GHRH plasmid, pAV0245 (SEQ ID No.: 64). In a fourth specific embodiment, the nucleic acid expression construct further comprises, a transfection-facilitating polypeptide (e.g. a charged polypeptide, or poly-L-glutamate). In a fifth specific embodiment, species-specific and synthetic signal peptides are described, and showed to impact dramatically the production and secretion of the transgene product, in our case GHRH. After delivering the optimized nucleic acid expression construct into the tissues of the animals or humans, expression of the encoded GHRH or functional biological equivalent thereof is initiated. Cellular trafficking and secretion is determined by the signal peptide used in the plasmid design. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQ ID No.: 14). The animal comprises a human, a food animal, a work animal (e.g. a pig, cow, sheep, goat or chicken), or a pet (e.g. dog, cat, horse).

A second aspect of the current invention includes a method of treating chronic disease in a chronically ill patient by optimized plasmid supplementation; the method comprises: designing an optimized plasmid, including species-specific signal petides; delivering into a tissue of the subject a nucleic acid expression construct that encodes a growth-hormone-releasing-hormone (GHRH) or functional biological equivalent thereof; wherein the GHRH is an aid used to improve the overall state of the chronically affected subject. The method generally comprises delivering into a tissue of the subject a nucleic acid expression construct that encodes a growth-hormone-releasing-hormone (GHRH) or functional biological equivalent thereof. Specific embodiments of the second aspect of this invention encompass various modes of delivering into the tissue of the subject the nucleic acid expression construct (e.g. an electroporation method, a viral vector, in conjunction with a carrier, by parenteral route, or a combination thereof). In a fifth preferred embodiment, the nucleic acid expression construct is delivered via an electroporation method comprising: a) penetrating the tissue in the human or farm animal with a plurality of needle electrodes, wherein the plurality of needle electrodes are arranged in a spaced relationship; b) introducing the nucleic acid expression construct into the tissue between the plurality of needle electrodes; and c) applying an electrical pulse to the plurality of needle electrodes. A sixth preferred embodiment includes the nucleic acid expression construct being delivered in a single dose, and the single dose comprising a total of about a 0.01-10 mg of nucleic acid expression construct. Generally the nucleic acid expression construct is delivered into a tissue of the subject comprising diploid cells (e.g. muscle cells). In a seventh specific embodiment the nucleic acid expression construct used for transfection comprises a HV-GHRH plasmid (SEQ ID No.: 25). Other specific embodiments utilize other nucleic acid expression constructs that are at least 90% identical to: an optimized bovine GHRH plasmid, pAV0236 (SEQ ID No.: 28); a TI-GHRH plasmid, pAV0239 (SEQ ID No.: 30); wt-porcine GHRH plasmid, pAV0225 (SEQ ID No.: 26); ovine GHRH plasmid, pAV0240 (SEQ ID No.: 31); chicken GHRH plasmid, pAV0241 (SEQ ID No.: 32); dog GHRH plasmid, pAV0235 (SEQ ID No.: 27); cat GHRH plasmid, pAV0238 (SEQ ID No.: 29); horse GHRH plasmid, pAV0249 (SEQ ID No.: 33); improved wild-type porcine GHRH plasmid, pAV0242 (SEQ ID No.: 61); human GHRH plasmid, pAV0243 (SEQ ID No.: 62); synthetic RPRP-GHRH plasmid, pAV0244 (SEQ ID No.: 63); or synthetic RPPP-GHRH plasmid, pAV0245 (SEQ ID No.: 64). In a eighth specific embodiment, the nucleic acid expression construct further comprises, a transfection-facilitating polypeptide (e.g. a charged polypeptide, or poly-L-glutamate). In a nine specific embodiment, species—specific and synthetic signal peptides are described, and showed to impact dramatically the production and secretion of the transgene product, in our case GHRH. After delivering the nucleic acid expression construct into the cells of the subject, expression and secretion of the encoded GHRH or functional biological equivalent thereof is initiated. Cellular trafficking and secretion is determined by the signal peptide used in the plasmid design. The encoded GHRH comprises a biologically active polypeptide; and the encoded functional biological equivalent of GHRH is a polypeptide that has been engineered to contain a distinct amino acid sequence while simultaneously having similar or improved biologically activity when compared to the GHRH polypeptide. One embodiment of a specific encoded GHRH or functional biological equivalent thereof is of formula (SEQ ID No.: 14). The animal comprises a human, food animal, or a work animal (e.g. a pig, cow, sheep, goat or chicken), or a pet (e.g. dog, cat, horse).

The current invention also pertains to methods useful for increasing quality of life and welfare in chronically ill subjects. The general method of this invention comprises treating a subject with an optimized plasmid mediated gene supplementation, containing a species-specific or optimized signal peptide. The method comprises delivering a nucleic acid expression construct that encodes a growth-hormone-releasing-hormone ("GHRH") or functional biological equivalent thereof into a tissue, such as a muscle, of the subject. The subsequent in vivo expression of the GHRH or biological equivalent in the subject is sufficient to treat the chronic illness. It is also possible to enhance this method by placing a plurality of electrodes in a selected tissue, then delivering nucleic acid expression construct to the selected tissue in an area that interposes the plurality of electrodes, and applying a cell-transfecting pulse (e.g. electrical) to the selected tissue in an area of the selected tissue where the nucleic acid expression construct was delivered. However, the cell-transfecting pulse need not be an electrical pulse, a different method, such as vascular pressure pulse can also be utilized. Electroporation, direct injection, gene gun, or gold particle bombardment are also used in specific embodiments to deliver the nucleic acid expression construct encoding the GHRH or biological equivalent into the subject. The subject in this invention comprises an animal (e.g. a human, a pig, a horse, a cow, a mouse, a rat, a monkey, a sheep, a goat, a dog, or a cat).

Recombinant GH replacement therapy is widely used in agriculture and clinically, with beneficial effects, but generally, the doses are supraphysiological. Such elevated doses of recombinant GH are associated with deleterious side-effects, for example, up to 30% of the recombinant GH treated subjects develop at a higher frequency insulin resistance (Gopinath and Etherton, 1989a; Gopinath and Etherton, 1989b; Verhelst et al., 1997) or accelerated bone epiphysis growth and closure in pediatric patients (Blethen and Rundle, 1996). In addition, molecular heterogeneity of circulating GH may have important implications in growth and homeostasis (Satozawa et al., 2000; Tsunekawa et al., 1999; Wada et al., 1998). Unwanted side effects result from the fact that treatment with recombinant exogenous GH protein raises basal levels of GH and abolishes the natural episodic pulses of GH. In contradistinction, no side effects have been reported for recombinant GHRH therapies. The normal levels of GHRH in the pituitary portal circulation range from about 150-to-800 pg/ml, while systemic circulating values of the hormone are up to about 100-500 pg/ml. Some patients with acromegaly caused by extracranial tumors have level that is nearly 100 times as high (e.g. 50 ng/ml of immunoreactive GHRH) (Thorner et al., 1984). Long-term studies using recombinant GHRH therapies (1-5 years) in children and elderly humans have shown an absence of the classical GH side-effects, such as changes in fasting glucose concentration or, in pediatric patients, the accelerated bone epiphysal growth and closure or slipping of the capital femoral epiphysis (Chevalier et al., 2000) (Duck et al., 1992; Vittone et al., 1997).

Numerous studies in humans, sheep or pigs showed that continuous infusion with recombinant GHRH protein restores the normal GH pattern without desensitizing GHRH receptors or depleting GH supplies (Dubreuil et al., 1990). As this system is capable of a degree of feed-back which is abolished in the GH therapies, GHRH recombinant protein therapy may be more physiological than GH therapy. However, due to the short half-life of GHRH in vivo, frequent (one to three times per day) intravenous, subcutaneous or intranasal (requiring 300-fold higher dose) administrations are necessary (Evans et al., 1985; Thorner et al., 1986). Thus, as a chronic therapy, recombinant GHRH protein administration is not practical. A gene transfer approach, however could overcome this limitations to GHRH use. Moreover, a wide range of doses can be therapeutic. The choice of GHRH and the choice of an appropriate signal peptide for a gene therapeutic application is favored by the fact that the gene, cDNA and native and several mutated molecules have been characterized for the pig, cattle and other species (Bohlen et al., 1983; Guillemin et al., 1982); we have isolated the cDNA of cat, dog and horse specific GHRH, and their species-specific signal peptides. The measurement of therapeutic efficacy is straightforward and unequivocal.

Among the non-viral techniques for gene transfer in vivo, the direct injection of plasmid DNA into muscle is simple, inexpensive, and safe. The inefficient DNA uptake into muscle fibers after simple direct injection hag led to relatively low expression levels (Prentice et al., 1994; Wells et al., 1997) In addition, the duration of the transgene expression has been short (Wolff et al., 1990). The most successful previous clinical applications have been confined to vaccines (Danko and Wolff, 1994; Tsurumi et al., 1996). Recently, significant progress to enhance plasmid delivery in vivo and subsequently to achieve physiological levels of a secreted protein was obtained using the electroporation technique. Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Our previous studies using growth hormone releasing hormone (GHRH) showed that plasmid therapy with electroporation is scalable and represents a promising approach to induce production and regulated secretion of proteins in large animals and humans (Draghia-Akli et al., 1999; Draghia-Akli et al., 2002c). Electroporation also has been extensively used in rodents and other small animals (Bettan et al., 2000; Yin and Tang, 2001). It has been observed that the electrode configuration affects the electric field distribution, and subsequent results (Gehl et al., 1999; Miklavcic et al., 1998). Preliminary experiments indicated that for a large animal model, needle electrodes give consistently better reproducible results than external caliper electrodes.

The ability of electroporation to enhance plasmid uptake into the skeletal muscle has been well documented, as described above. In addition, plasmid formulated with PLG or polyvinylpyrrolidone ("PVP") has been observed to increase gene transfection and consequently gene expression to up to 10-fold in the skeletal muscle of mice, rats and dogs (Fewell et al., 2001; Mumper et al., 1998). Although not wanting to be bound by theory, PLG will increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, process that substantially increases the transfection efficiency.

The plasmid supplementation approach to treat chronic illness in subjects using appropriate plasmids for each application, including appropriate signal peptides described herein offers advantages over the limitations of directly injecting recombinant GH or GHRH protein. Expression and secretion from the producing cells of novel biological equivalents of GHRH that are serum protease resistant can be directed by an expression plasmid controlled by a synthetic muscle-specific promoter, and containing signal peptides that favor secretion or retention of proteins within the cell. Expression of such GHRH or biological equivalent thereof elicited high GH and IGF-I levels in subjects that have had the encoding sequences delivered into the cells of the subject by intramuscular injection and in vivo electroporation. Although in vivo electroporation is the preferred method of introducing the heterologous nucleic acid encoding system into the cells of the subject, other methods exist and should be known by a person skilled in the art (e.g. electroporation, lipofectamine, calcium phosphate, ex vivo transformation, direct injection, DEAE dextran, sonication loading, receptor mediated transfection, microprojectile bombardment, etc.). For example, it may also be possible to introduce the nucleic acid sequence that encodes the GHRH or functional biological equivalent thereof directly into the cells of the subject by first removing the cells from the body of the subject or donor, maintaining the cells in culture, then introducing the nucleic acid encoding system by a variety of methods (e.g. electroporation, lipofectamine, calcium phosphate, ex vivo transformation, direct injection, DEAE dextran, sonication loading, receptor mediated transfection, microprojectile bombardment, etc.), and finally reintroducing the modified cells into the original subject or other host subject (the ex vivo method). The GHRH sequence can be cloned into an adenovirus vector or an adeno-associated vector and delivered by simple intramuscular injection, or intravenously or intra-arterially. Plasmid DNA carrying the GHRH sequence can be complexed with cationic lipids or liposomes and delivered intramuscularly, intravenously or subcutaneous.

Administration as used herein refers to the route of introduction of a plasmid, vector or carrier of DNA into the body. Administration can be directly to a target tissue or by targeted delivery to the target tissue after systemic administration. In particular, the present invention can be used for treating disease by administration of the plasmid or vector to the body in order to establishing controlled expression of any specific nucleic acid sequence within tissues at certain levels that are useful for plasmid mediated supplementation. The preferred means for administration of vector and use of formulations for delivery are described above.

Muscle cells have the unique ability to take up DNA from the extracellular space after simple injection of DNA particles as a solution, suspension, or colloid into the muscle. Expression of DNA by this method can be sustained for several months. DNA uptake in muscle cells is further enhance utilizing in vivo electroporation.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determine the bioavailability of the vector within the body. Other elements of the formulation function as ligands that interact with specific receptors on the surface or interior of the cell. Other elements of the formulation function to enhance entry into the cell, release from the endosome, and entry into the nucleus.

Delivery can also be through use of DNA transporters. DNA transporters refer to molecules which bind to DNA vectors and are capable of being taken up by epidermal cells. DNA transporters contain a molecular complex capable of non-covalently binding to DNA and efficiently transporting the DNA through the cell membrane. It is preferable that the transporter also transports the DNA through the nuclear membrane. See, e.g., the following applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993.

Another method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine; one element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multi-lamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over extended periods of time.

Myoblasts eventually differentiate and fuse to existing muscle tissue. Myoblasts can easily be obtained by taking muscle tissue from an individual who needs plasmid-mediated supplementation and the genetically engineered cells can also be easily put back with out causing damage to the patient's muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting with an appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the El region of the virus genome with the vector elements described in this invention including promoter, 5'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

Although not wanting to be bound by theory, it is believed that in order to provide an acceptable safety margin for the use of such heterologous nucleic acid sequences in humans, a regulated gene expression system is mandated to possess low levels of basal expression of GHRH, and still retain a high ability to induce. Thus, targeted gene expression can be regulated by incorporating molecular switch technology. The HV-GHRH (SEQID No.: 1) or biological equivalent molecule displays a high degree of stability in serum, with a half-life of 6 hours, versus the natural GHRH, that has a 6-12 minutes half-life. Thus, by combining the powerful electroporation DNA delivery method with stable and regulable GHRH or biological equivalent encoded nucleic acid sequences, a therapy can be utilized that will enhance animal welfare, decrease culling rates and increase body condition scores.

Vectors

The term "vector" is used to refer to a carrier nucleic acid molecule into which a nucleic acid sequence can be inserted for introduction into a cell wherein, in some embodiments, it can be replicated. A nucleic acid sequence can be native to the animal, or it can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques.

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operatively linked coding sequence in a particular host cell. In addition to control sequences that govern transcription and translation, vectors and expression vectors may contain nucleic acid sequences that serve other functions as well and are described infra.

Plasmid Vectors

In certain embodiments, a linear DNA fragment from a plasmid vector is contemplated for use to transfect a eukaryotic cell, particularly a mammalian cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. Other plasmids contain genes for kanamycin or neomycin, or have a non-antibiotic selection mechanism. The pBR plasmid, or other microbial plasmid or phage must also contain, or be modified to contain, for example, promoters which can be used by the microbial organism for expression of its own proteins. A skilled artisan recognizes that any plasmid in the art may be modified for use in the methods of the present invention. In a specific embodiment, for example, a GHRH vector used for the therapeutic applications is synthetically produced and has a kanamycin resistance gene.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

Promoters and Enhancers

A promoter is a control sequence that is a region of a nucleic acid sequence at which initiation and rate of transcription of a gene product are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control", and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the thymidine kinase promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Tables 1 and 2 list non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

| Promoter and/or Enhancer | |
|---|---|
| Promoter/Enhancer | Relevant References |
| β-Actin | (Kawamoto et al., 1988; Kawamoto et al., 1989) |
| Muscle Creatine Kinase (MCK) | (Horlick and Benfield, 1989; Jaynes et al., 1988) |
| Metallothionein (MTII) | (Inouye et al., 1994; Narum et al., 2001; Skroch et al., 1993) |
| Albumin | (Pinkert et al., 1987; Tronche et al., 1989) |

TABLE 1-continued

| Promoter and/or Enhancer | |
|---|---|
| Promoter/Enhancer | Relevant References |
| β-Globin | (Tronche et al., 1990; Trudel and Costantini, 1987) |
| Insulin | (German et al., 1995; Ohlsson et al., 1991) |
| Rat Growth Hormone | (Larsen et al., 1986) |
| Troponin I (TN I) | (Lin et al., 1991; Yutzey and Konieczny, 1992) |
| Platelet-Derived Growth Factor (PDGF) | (Pech et al., 1989) |
| Duchenne Muscular Dystrophy | (Klamut et al., 1990; Klamut et al., 1996) |
| Cytomegalovirus (CMV) | (Boshart et al., 1985; Dorsch-Hasler et al., 1985) |
| Synthetic muscle specific promoters (c5-12, c1-28) | (Draghia-Akli et al., 1999; Draghia-Akli et al, 2002c; Li et al., 1999) |

TABLE 2

| Element/Inducer | |
|---|---|
| Element | Inducer |
| MT II | Phorbol Ester (TFA) |
| | Heavy metals |
| MMTV (mouse mammary tumor virus) | Glucocorticoids |
| β-Interferon | Poly(rI)x/Poly(rc) |
| Adenovirus 5 E2 | EIA |
| Collagenase | Phorbol Ester (TPA) |
| Stromelysin | Phorbol Ester (TPA) |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2κb | Interferon |
| HSP70 | EIA, SV40 Large T Antigen |
| Proliferin | Phorbol Ester-TPA |
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), DIA dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (Li et al., 1999), which contains a proximal serum response element ("SRE") from skeletal a-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors.

Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention.

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819; , each herein incorporated by reference).

Multiple Cloning Sites

Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998) incorporated herein by reference). "Restriction enzyme digestion" refers to catalytic cleavage of a nucleic acid molecule with an enzyme that functions only at specific locations in a nucleic acid molecule. Restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, (Chandler et al., 1997).

Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues ("polyA") to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

Polyadenylation Signals

In expression, particularly eukaryotic expression, one will typically include a polyadenylation signal to effect proper polyadenylation of the transcript. Preferred embodiments include the SV40 polyadenylation signal, skeletal alpha actin 3'UTR or the human or bovine growth hormone polyadenylation signal, convenient and known to function well in various target cells. Polyadenylation may increase the stability of the transcript or may facilitate cytoplasmic transport.

Origins of Replication

In order to propagate a vector in a host cell, it may contain one or more origins of replication sites (often termed "ori"), which is a specific nucleic acid sequence at which replication is initiated. Alternatively an autonomously replicating sequence ("ARS") can be employed if the host cell is yeast.

Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Mutagenesis

Where employed, mutagenesis was accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Site-Directed Mutagenesis

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as E. coli polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as E. coli cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multi-residue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site-specific mutants must be studied. However, improved techniques make production and rapid-screening of mutants much more straightforward. See also, U.S. Pat. Nos. 5,798,208 and 5,830,650, for a description of "walk-through" mutagenesis. Other methods of site-directed mutagenesis are disclosed in U.S. Pat. Nos. 5,220,007; 5,284,760; 5,354,670; 5,366,878; 5,389,514; 5,635,377; and 5,789,166.

Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No.5,384,253, incorporated herein by reference). Alternatively, recipient cells can be made more susceptible to transformation by mechanical wounding and other methods known in the art.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances maintain a resting transmembrane potential of circa 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula E=V/d, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the inter-electrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of two, four or six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

Overcoming the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determine by the nature of tissue, the size of the selected tissue and distance between electrodes. It is desirable that the voltage pulse be as homogenous as possible and of the correct amplitude. Excessive field strength results in the lysing of cells, whereas a low field strength results in reduced efficacy of electroporation. Some electroporation devices utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

Restriction Enzymes

In some embodiments of the present invention, a linear DNA fragment is generated by restriction enzyme digestion of a parent DNA molecule. Examples of restriction enzymes are provided below.

| Name | Recognition Sequence |
|---|---|
| AatII | GACGTC |
| Acc65 I | GGTACC |
| Acc I | GTMKAC |
| Aci I | CCGC |
| Acl I | AACGTT |
| Afe I | AGCGCT |
| Afl II | CTTAAG |
| Afl III | ACRYGT |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| ApaL I | GTGCAC |
| Apo I | RAATTY |

-continued

| Name | Recognition Sequence |
|---|---|
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |
| Bcl I | TGATCA |
| Bfa I | CTAG |
| Bgl I | GCCNNNNNGGC |
| Bgl II | AGATCT |
| Blp I | GCTNAGC |
| Bmr I | ACTGGG |
| Bpm I | GTGGAG |
| BsaA I | YACGTR |
| BsaB I | GATNNNNATC |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| Bsl I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp1286 I | GDGCHC |

-continued

| Name | Recognition Sequence |
|---|---|
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC |
| BstB I | TTCGAA |
| BstE II | GGTNACC |
| BstF5 I | GGATGNN |
| BstN I | CCWGG |
| BstU I | CGCG |
| BstX I | CCANNNNNNTGG |
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |

-continued

| Name | Recognition Sequence |
|---|---|
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinP1 I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |
| MspA1 I | CMGCKG |
| Msp I | CCGG |
| Mwo I | GCNNNNNNNGC |
| Nae I | GCCGGC |
| Nar I | GGCGCC |
| Nci I | CCSGG |
| Nco I | CCATGG |
| Nde I | CATATG |
| NgoMI V | GCCGGC |

-continued

| Name | Recognition Sequence |
|---|---|
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| PleI | GAGTC |
| Pme I | GTTTAAAC |
| Pml I | CACGTG |
| PpuM I | RGGWCCY |
| PshA I | GACNNNNGTC |
| Psi I | TTATAA |
| PspG I | CCWGG |
| PspOM I | GGGCCC |
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |

-continued

| Name | Recognition Sequence |
|---|---|
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTGG |
| Xho I | CTCGAG |
| Xma I | CCCGGG |
| Xmn I | GAANNNNTTC |

The term "restriction enzyme digestion" of DNA as used herein refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 1-2 units of enzyme in about 20 μl of buffer solution. Appropriate buffers and substrate amounts for particular restriction enzymes are specified by the manufacturer. Restriction enzymes are used to ensure plasmid integrity and correctness.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Construction of DNA Vecors and Methods

DNA constructs: In order to prevent or treat chronic conditions in subjects by utilizing plasmid mediated gene supplementation, it was first necessary to design several GHRH constructs. Briefly, the plasmid vectors contained the muscle specific synthetic promoter SPc5-12 (SEQID No.: 15)(Li et al., 1999) attached to a wild type species-specific or analog GHRH. Some wild-type GHRH sequences were cloned in our laboratory (dog, cat and horse); others (chicken, ovine, bovine, porcine) were synthesized according to the specialized literature. The signal peptides of these hormones have also been cloned by us and others. Also, synthetic signal peptides have been created by us to enhance the secretion of the transgene product from muscle cells into the circulation. The analog GHRH sequences were generated by site directed mutagenesis as described (Draghia-Akli et al., 1999). Briefly, mammalian GHRH analog cDNA's were generated by site directed mutagenesis of GHRH cDNA (SEQID No.: 18) (Altered Sites II in vitro Mutagenesis System, Promega, Madison, Wis.), and cloned into the BamHI/Hind III sites of pSPc5-12, to generate the specific GHRH construct. The entire plasmid sequence was then synthetically produced. A reduced 3' untranslated region (3'UTR) of growth hormone was included downstream of GHRH cDNA. The resultant plasmids contained mammalian analog coding region for GHRH, and the resultant amino acid sequences were not naturally present in mammals. Species-specific signal peptides were included in some constructs, and modified in others. Although not wanting to be bound by theory, the prevention or treatment chronic disease in subjects are determined ultimately by the circulating levels of GHRH hormones. Several different plasmids encoded different mutated or wild type amino acid sequences of GHRH or functional biological equivalents thereof, for example:

Plasmid Encoded Amino Acid Sequence

```
HV-GHRH (SEQID No.: 1):
HVDAIFTNSYRKVLAQLSARKLLQDILNRQQGERNQEQGA-OH

Pig-GHRH (SEQID No.: 2):
YADAIFTNSYRKVLGQLSARKLLQDIMSRQQGERNQEQGA-OH

Bovine-GHRH (SEQID No.: 3):
YADAIFTNSYRKVLGQLSARKLLQDIMNRQQGERNQEQGA-OH

Dog-GHRH (SEQID No.: 4):
YADAIFTNSYRKVLGQLSARKLLQDIMSRQQGERNREQGA-OH

Cat-GHRH (SEQID No.: 5):
YADAIFTNSYRKVLGQLSARKLLQDIMSRQQGERNQEQGA-OH

TI-GHRH (SEQID No.: 6):
YIDAIFTNSYRKVLAQLSARKLLQDILNRQQGERNQEQGA-OH

Ovine-GHRH (SEQID No.: 7):
YADAIFTNSYRKILGQLSARKLLQDIMNRQQGERNQEQGA-OH
```

-continued

```
Chicken-GHRH (SEQ ID No.: 8):
HADGIFSKAYRKLLGQLSARNYLHSLMAKRVGSGLGDEAEPLS-OH Horse-GHRH (partial) (SEQ ID No.: 9):
YADAIFTNNYRKVLGQLSARKILQDIMSR-----------OH Human-GHRH (SEQ ID No.: 10):
YADAIFTNSYRKVLGQLSARKLLQDIMSRQQGESNQERGA-OH TV-GHRH (SEQ ID No.: 11):
YVDAIFTNSYRKVLAQLSARKLLQDILNRQQGERNQEQGA-OH TA-15/27/28-GHRH (SEQ ID No.: 12):
YADAIFTNSYRKVLAQLSARKLLQDILNRQQGERNQEQGA-OH
```

In general, the encoded GHRH or functional biological equivalent thereof is of formula:

$$-X_1-X_2\text{-DAIFTNSYRKVL-}X_3\text{-QLSARKLLQDI-}X_4-X_5\text{-RQQGE-}X_6\text{-N-}X_7\text{-E-}X_8\text{-GA-OH} \quad \text{(SEQ ID No.: 14)}$$

wherein: $X_1$ is a D-or L-isomer of an amino acid selected from the group consisting of tyrosine ("Y"), or histidine ("H"); $X_2$ is a D-or L-isomer of an amino acid selected from the group consisting of alanine ("A"), valine ("V"), or isoleucine ("I"); $X_3$ is a D-or L-isomer of an amino acid selected from the group consisting of alanine ("A") or glycine ("G"); $X_4$ is a D-or L-isomer of an amino acid selected from the group consisting of methionine ("M"), or leucine ("L"); $X_5$ is a D-or L-isomer of an amino acid selected from the group consisting of serine ("S") or asparagines ("N"); $X_6$ is a D- or L-isomer of an amino acid selected from the group consisting of arginine ("R"), or serine ("S"); $X_7$ is a D- or or L-isomer of an amino acid selected from the group consisting of arginine ("R"), or glutamine ("Q"); and $X_8$ is a D- or L-isomer of an amino acid selected from the group consisting of arginine ("R"), or glutamine ("Q").

Although not wanting to be bound by theory, the prevention or treatment chronic disease in subjects are determined ultimately by the circulating levels of GHRH hormones, or local levels in the target organs. Several different plasmids encoded different mutated or wild type amino acid sequences of GHRH or functional biological equivalents thereof, and under the secretory control of species-specific or modified signal peptides, as of:

Plasmid Encoded Signal Peptide Amino Acid Sequence

```
HV-GHRH (SEQ ID No.: 41):
MVLWVFFFVILTLSNSSHCSPPPPLTLRMRR-OH

Pig-GHRH (SEQ ID No.: 42):
MVLWVFFFVILTLSNSSHCSPPPPLTLRMRR-OH

Bovine-GHRH (SEQ ID No.: 43):
MVLWVFFLVTLTLSSGSHGSLPS-QPLRIPR-OH

Dog-GHRH (SEQ ID No.: 44):
MVLWVFFLVILTLSSGSHSSPPS-LPIRIPR-OH

Cat-GHRH (SEQ ID No.: 45):
MVLWVFFLVILTLDSGSHCSPPS-LPLRMPR-OH

Ovine-GHRH (SEQ ID No.: 46):
MVLWVFFLVTLTLSSGSHGSLPS-QPLRIPR-OH

Chicken-GHRH (SEQ ID No.: 47):
-MALWVFFVLLTLTSGSHCSLPPSPPFRVRR-OH

Horse-GHRH (SEQ ID No.: 48):
MVLWVFFFVILTLSNSSHCSPPPPLTLRMRR-OH

Human-GHRH (SEQ ID No.: 49):
MPLWVFFFVILTLSNSSHCSPPPPLTLRMRR-OH

Synthetic RPRP (SEQ ID No.: 50):
MPLWVFFFVILTLSNSSHCSRPRPLTLRMRR-OH

Synthetic RPPP (SEQ ID No.: 51):
MPLWVFFFVILTLSNSSHCSRPPPLTLRMRR-OH
```

The plasmids contain the species-specific or modified signal peptides with the consensus sequence (SEQ ID No.: 52):

$$\text{MVLWVFF-}X_1\text{-VILTLS-}X_2\text{-}X_3\text{-SHCS-}X_4\text{-P-}X_5\text{-}X_6\text{-LPLRM-}X_7\text{-R—OH}$$

wherein: $X_1$ is a D-or L-isomer of an amino acid selected from the group consisting of leucine ("L"), or phenylalanine ("F"); $X_2$ is a D-or L-isomer of an amino acid selected from the group consisting of serine ("S"), or asparagine ("N"); $X_3$ is a D-or L-isomer of an amino acid selected from the group consisting of glycine ("G") or serine ("S"); $X_4$ may be absent, or is a D-or L-isomer of an amino acid selected from the group consisting of arginine ("R"), proline ("P") or serine ("S"); $X_5$ is a D-or L-isomer of an amino acid selected from the group consisting of arginine ("R"), proline ("P") or serine ("S"); $X_6$ is a D- or L-isomer of an amino acid selected from the group consisting of arginine ("R"), or proline ("P"); $X_7$ is a D- or L-isomer of an amino acid selected from the group consisting of arginine ("R"), or proline ("P").

Usually, the signal for proteolitic cleavage generally occurs at an arginine-arginine or lysine-arginine site, but it can be sometimes different, and only one basic amino-acid may be sufficient. In the case of GHRH the different signal peptides have different cleavage sites, with half of peptides having an arginine-arginine signal, and half having a proline-arginine signal. It may be possible that the arginine-arginine signal promotes higher secretion than the arginine-proline, based on the specific properties of the two amino-acids. This phenomenon has not been described for any of the hormones in the GHRH axis. Nevertheless, it is known that substitutions in signal peptides can have a profound impact on hormone secretion and clinical effects: for instance it is known that a leucine to proline substitution in the neuropeptide Y (NPY) signal results in significantly lower plasma NPY levels (Kallio et al., 2003), or that the polymorphism at position 25 of the gene encoding transforming growth factor-beta1 (TGF-beta1), which changes the amino acid sequence of the signal peptide sequence (arginine to proline), is causing a variation in TGF-beta1 production. In patients with severe hepatic fibrosis, the Pro25 allele is twice as frequent compared to patients with mild fibrosis (Tag et al., 2003).

Some of the signal peptides (dog, cat, horse) were previously unknown and isolated in our laboratory by species-specific hypothalamic genomic library screening. A custom cDNA library was constructed by Clontech Laboratories, inc., Palo Alto, Calif. The starting tissue for the library was dog, cat or horse hypothalamus (4.7-5.2 gm) which had been collected from animals kept in experimental facilities (NIH regulations) from birth to death and stored at −80° C. The cDNA library was screened by PCR using a 5' primer selected from the BamHI/HindIII fragment of human GHRH and a 3' primer selected from sequence in exon 5 of bovine GHRH.

```
Bam/Hind III
5' Primer:
ATG GTG CTC TGG GTG TTC TT   (SEQ ID No.: 53)
```

-continued

Exon 5
3' Primer:
TTC ATC TTT GGG AGT TCC TG (SEQID No.: 54)

PCR conditions were as following: DNA (library) 3 µl, 10× Accutaq buffer 5 µl, DMSO 1 µl, dNTP's (10 mM) 1 µl, Exon3-5' primer (50 ng) 1 µl, Exon 5-3'primer (50 ng) 1 µl, water 37.5 µl, Accutaq 0.5 µl, with the following cycling parameters: 94° C. 10 min, 94° C. 30 sec, 55° C. 30 sec, 68° C. 30 sec for 35 cycles, followed by a cycle at 68 ° C. for 5 min.

The PCR fragment generated, approx. 200 bp, was subcloned using the topo cloning kit and sent for sequencing. A positive clone for each species was found to be complete and aligned and compared with other GHRH sequences, as that of human GHRH.

Primers were designed with specific mutations to incorporate a restriction sites to facilitate sub-cloning into expression vectors: NcoI, Hind III sites and 2 stop codons for insertion into the new pAV backbone. The newly generated expected band size is approximately 240 bp.

PCR Conditions were as following: DNA (positive clone) 10 ng, 10×Accutaq buffer 5 µl, DMSO 1 µl, dNTP's (10 mM) 1 µl, 5' primer (50 ng) 1 µl, 3'primer (50 ng) 1 µl, water 40.5 µl, Accutaq 0.5 µl. The cycling parameters were as following: 95° C. for 3' min, 94° C. 30 sec, 52° C. 30 sec, 68° C. 30 sec, for 30 cycles, followed by on extension at 68° C. for 5 min.

PCR reaction mix digested with NcoI and HindiHI and ligated into the new backbone using Takara ligase; clones were then sequenced to confirm that restriction sites and stop codons had been incorporated. Muscle cells (Sol 8 or L6) were transfected with the resulting vector and a Northern blot confirmed presence of species specific RNA.

The plasmids described above do not contain polylinker, IGF-I gene, a skeletal alpha-actin promoter or a skeletal alpha-actin 3' UTR/NCR. Furthermore, these plasmids were introduced by muscle injection, followed by in vivo electroporation, as described below.

In terms of "functional biological equivalents", it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Functional biological equivalents are thus defined herein as those proteins (and poly-nucleotides) in selected amino acids (or codons) may be substituted. A peptide comprising a functional biological equivalent of GHRH is a polypeptide that has been engineered to contain distinct amino acid sequences while simultaneously having similar or improved biologically activity when compared to GHRH. For example one biological activity of GHRH is to facilitate growth hormone ("GH") secretion in the subject.

Figure 3:
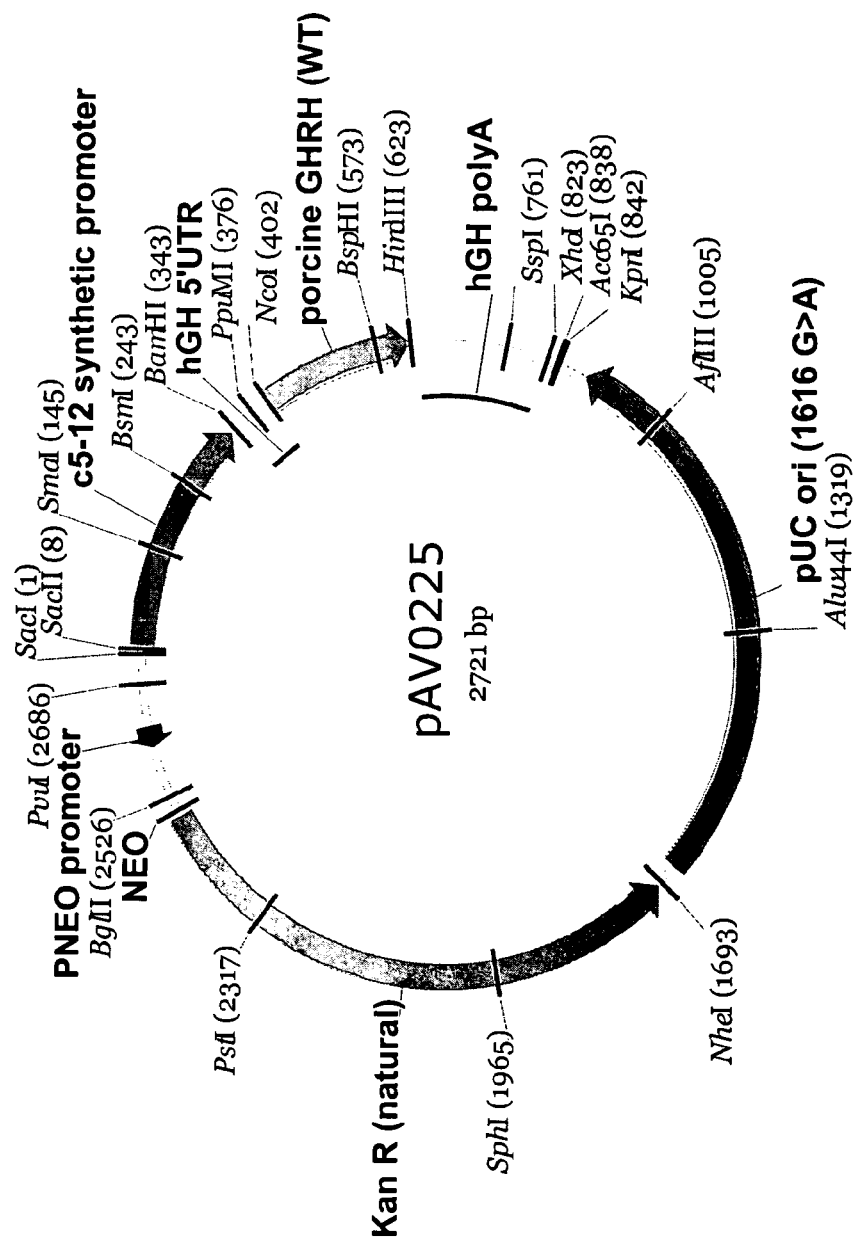
FIG. 3 shows a restriction map of pAV0225 expression plasmid.
Figure 4:
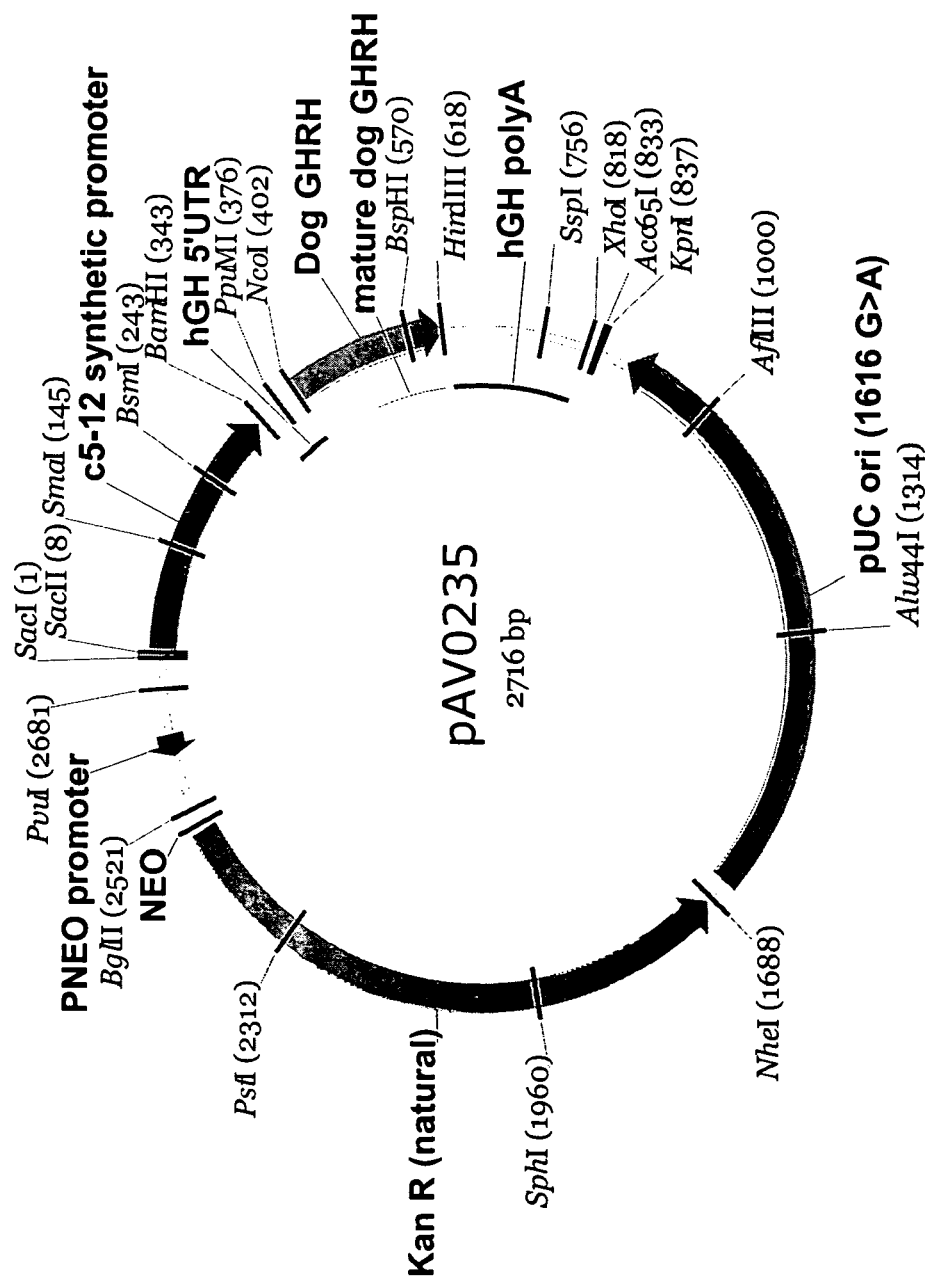
FIG. 4 shows a restriction map of pAV0235 expression plasmid.
Figure 5:
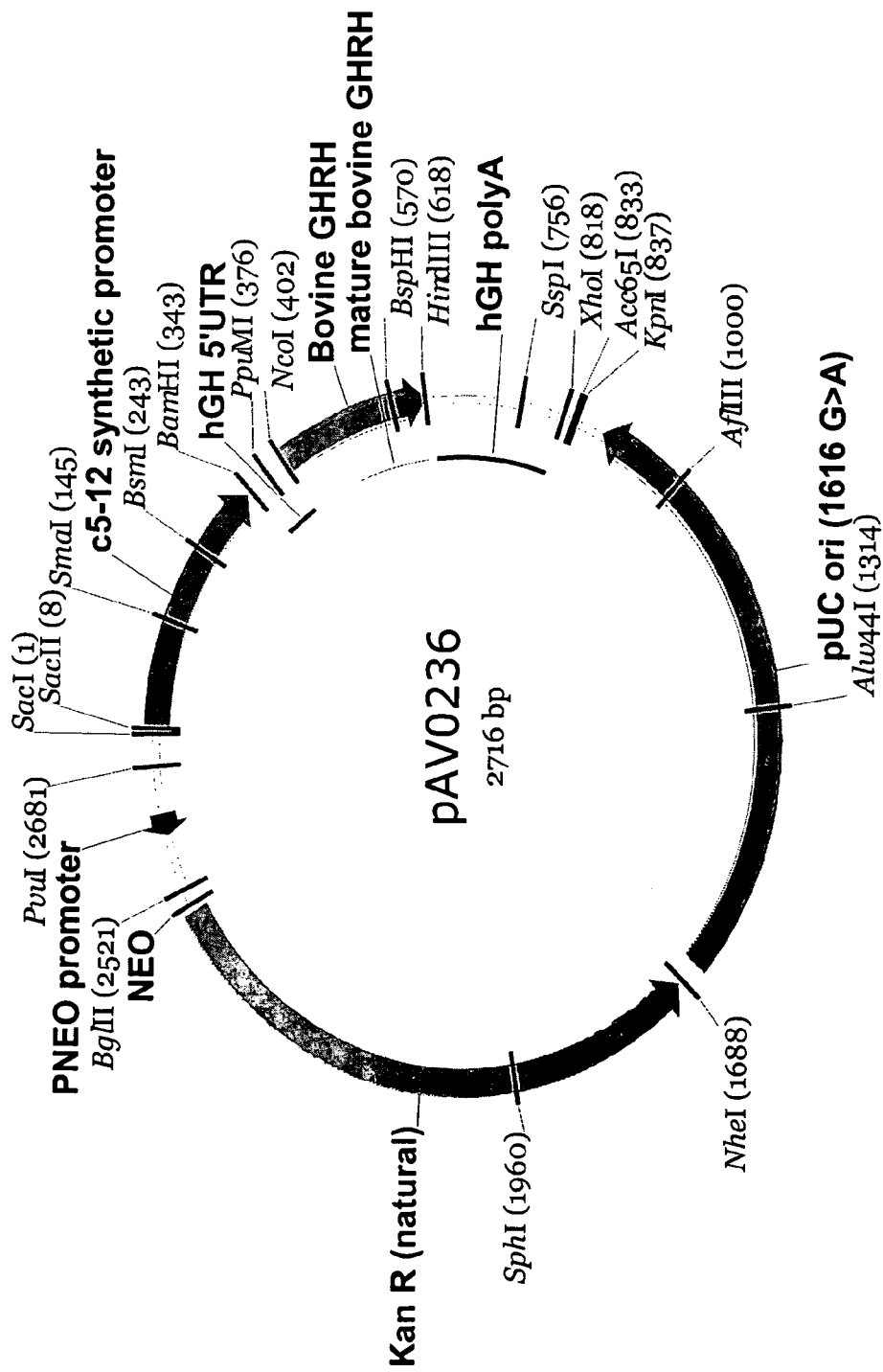
FIG. 5 shows a restriction map of pAV0236 expression plasmid.
Figure 6:
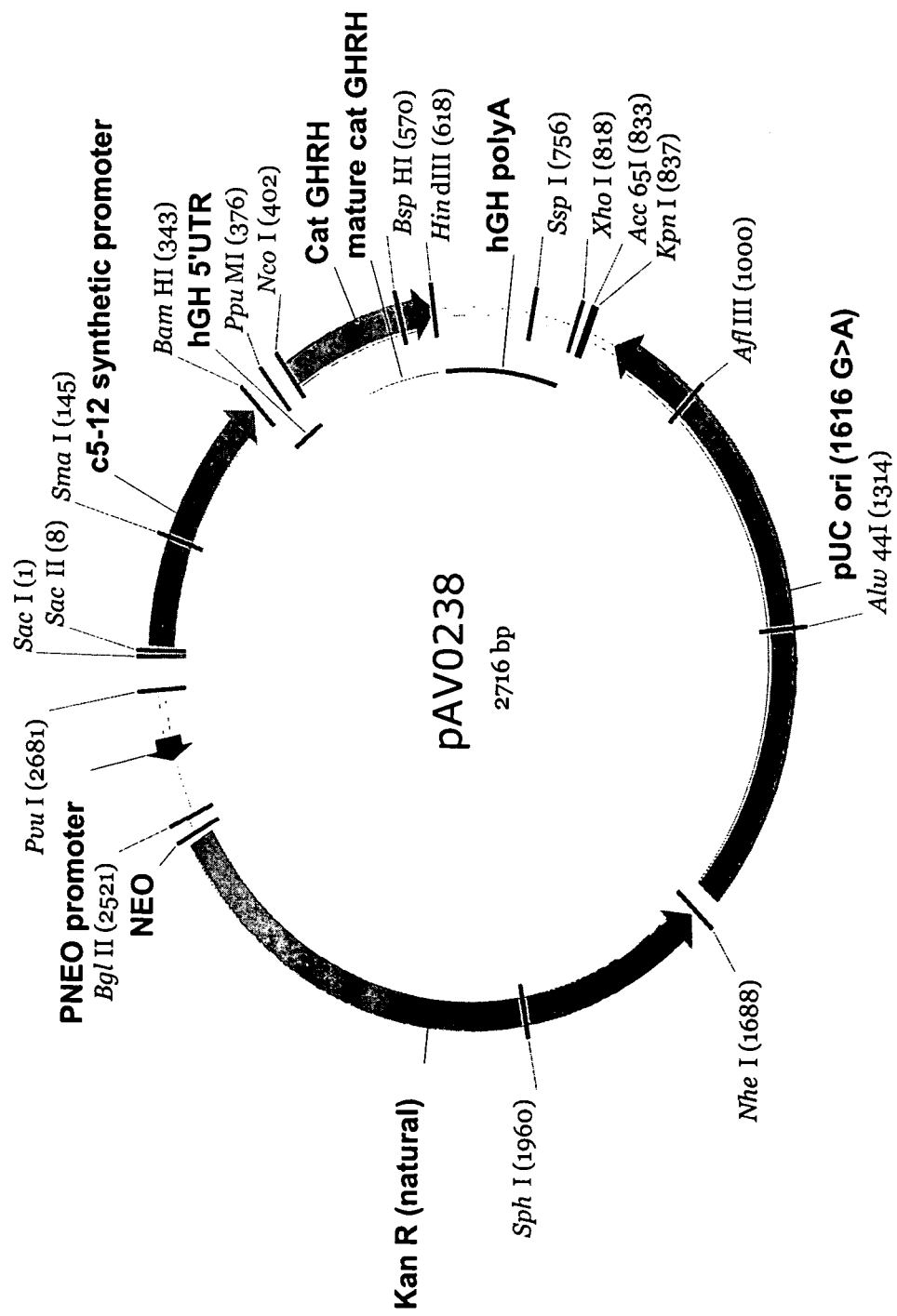
FIG. 6 shows a restriction map of pAV0238 expression plasmid.
Figure 7:
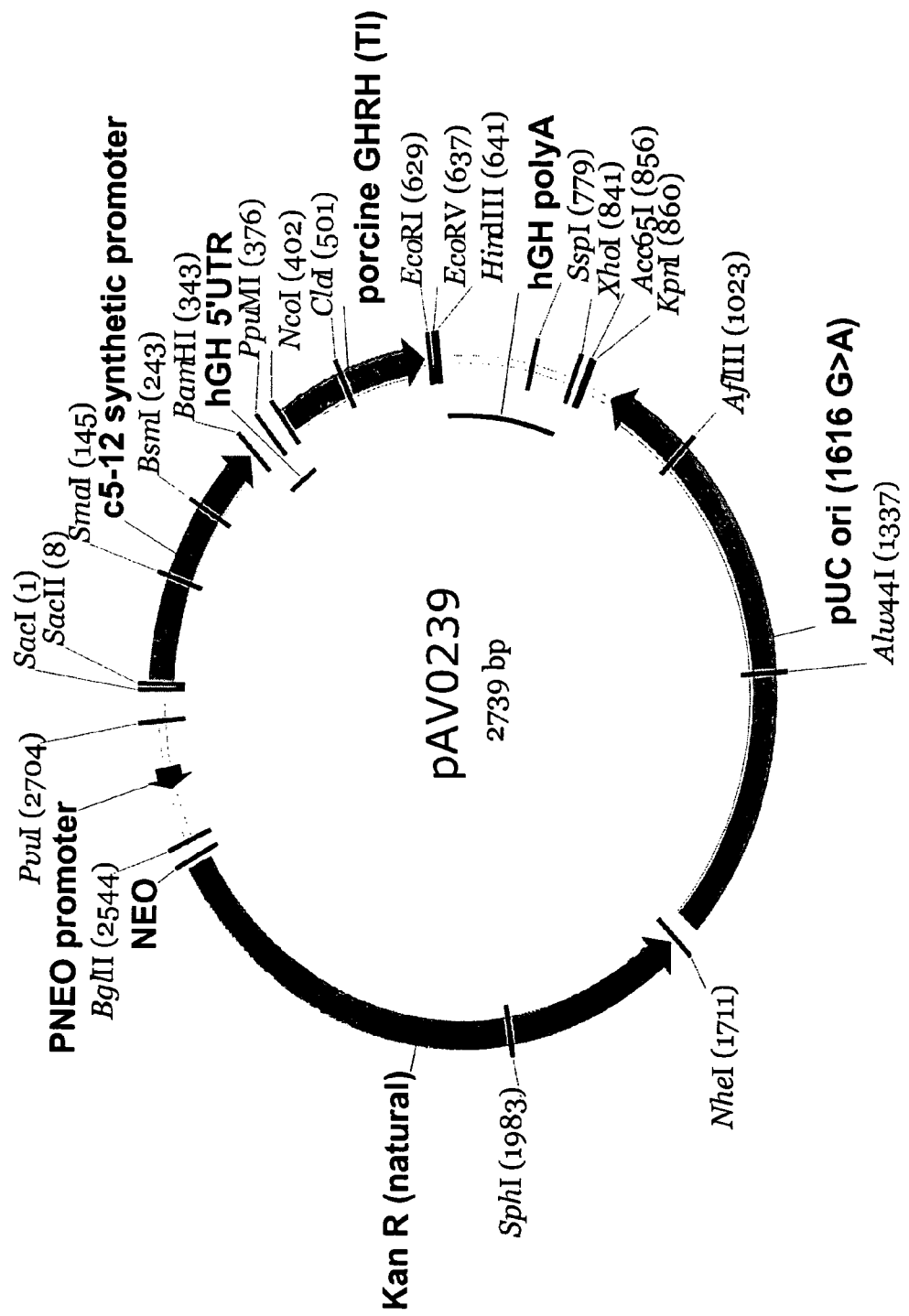
FIG. 7 shows a restriction map of pAV0239 expression plasmid.
Figure 8:
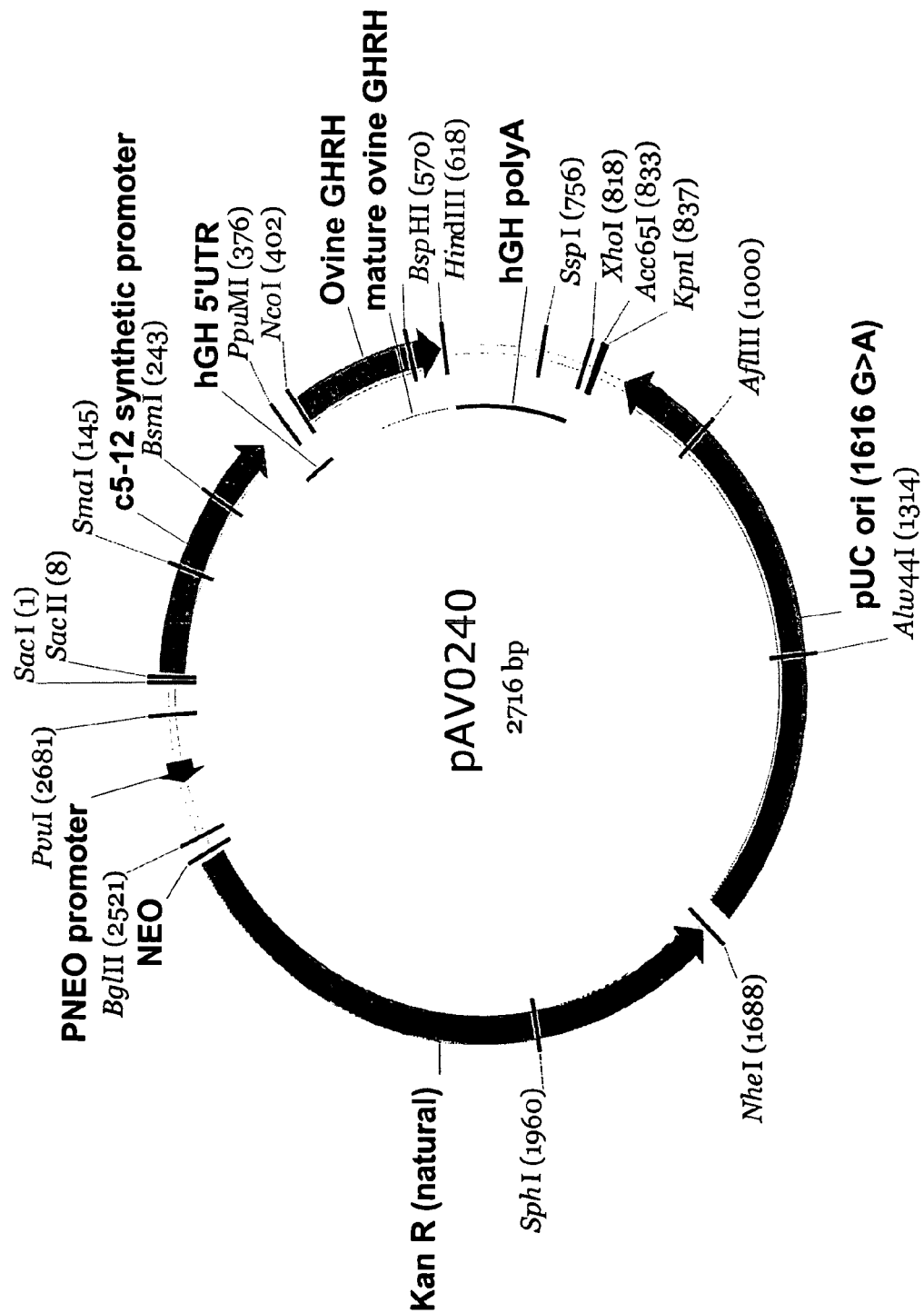
FIG. 8 shows a restriction map of pAV0240 expression plasmid.
Figure 9:
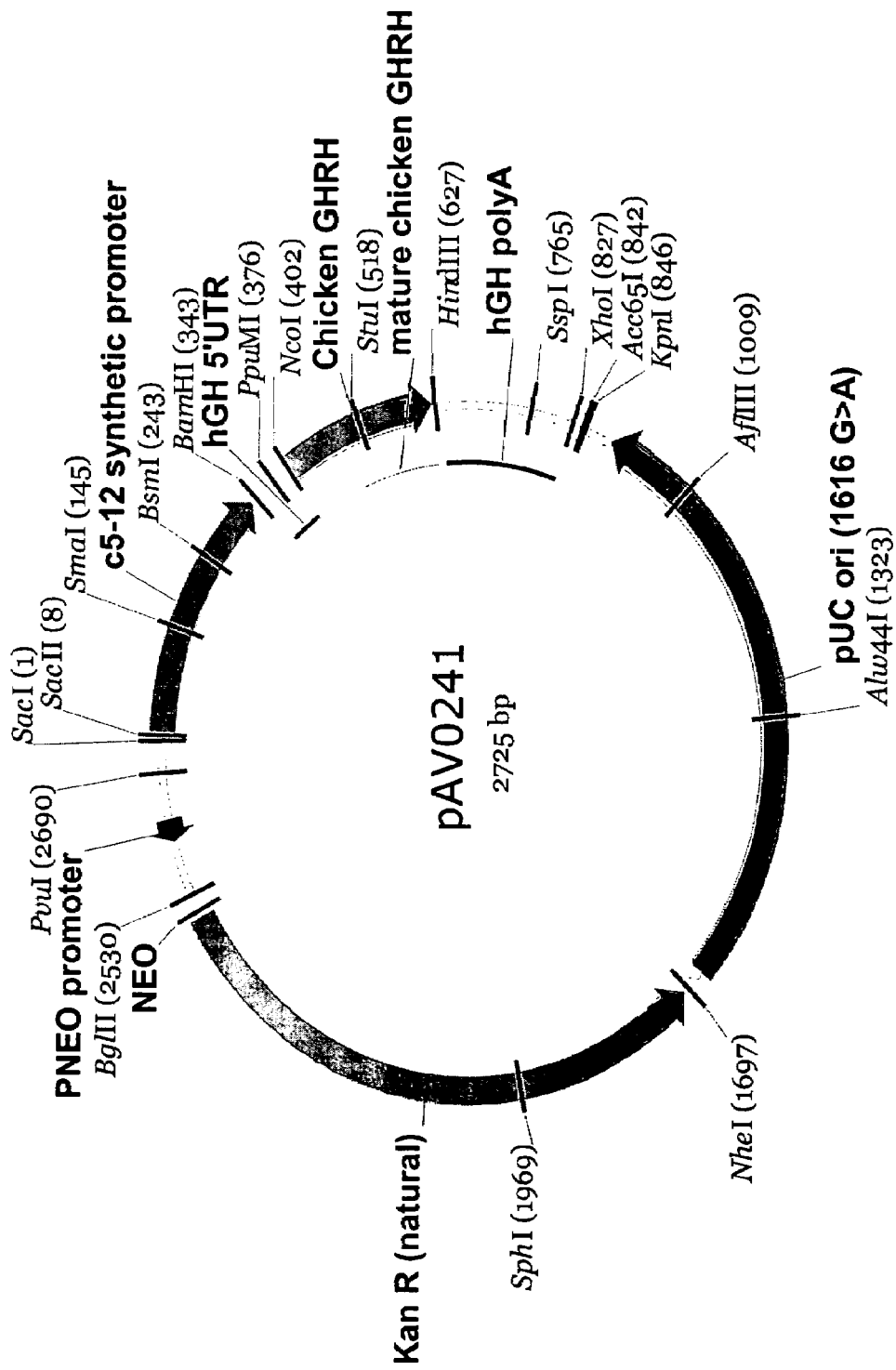
FIG. 9 shows a restriction map of pAV0241 expression plasmid.
Figure 10:
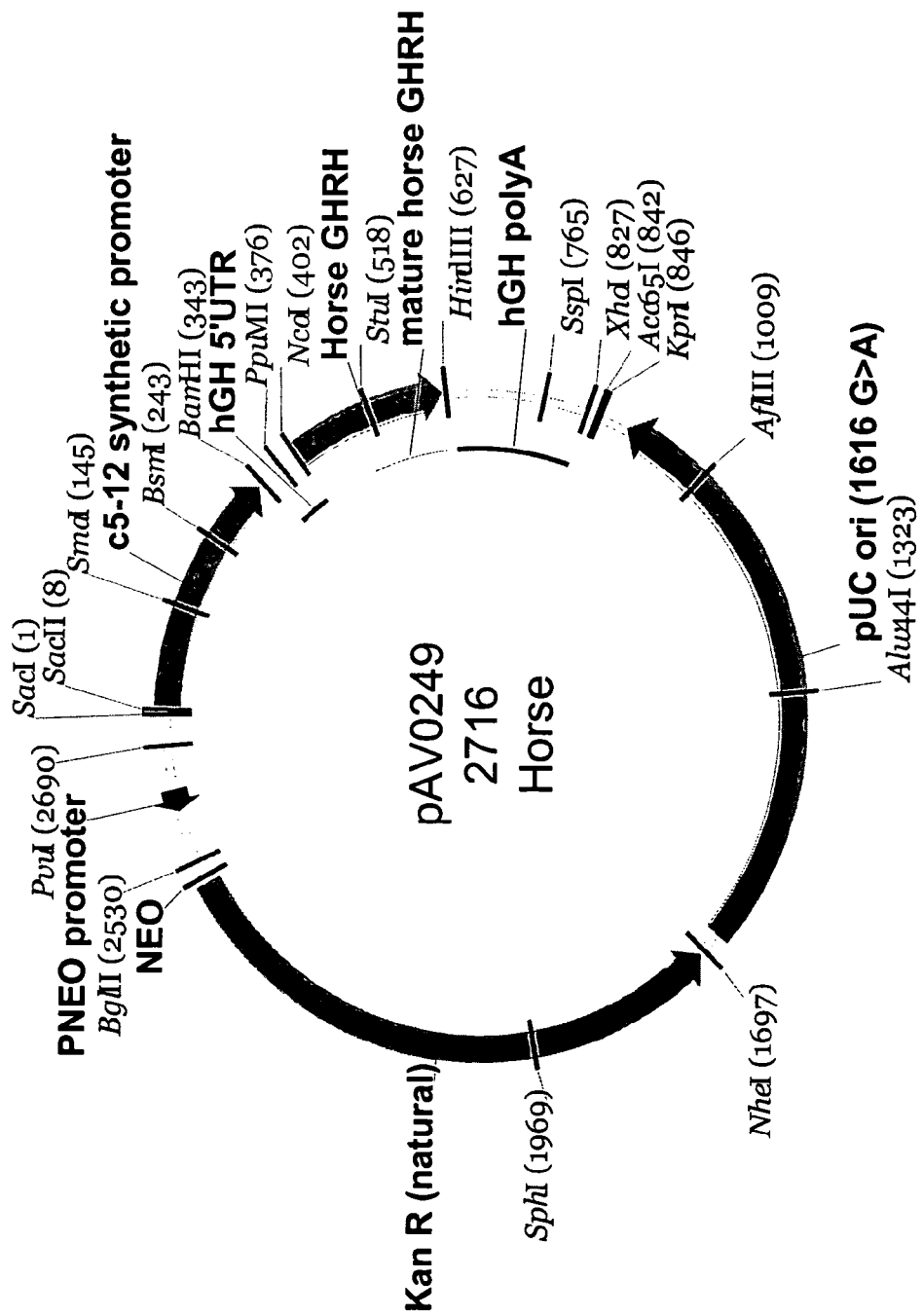
FIG. 10 shows a restriction map of pAV0249 expression plasmid.

Optimized Plasmid Backbone. One aspect of the current invention is the optimized plasmid backbone. The synthetic plasmids presented below contain eukaryotic sequences that are synthetically optimized for species-specific mammalian transcription. An existing pSP-HV-GHRH plasmid ("pAV0125") (SEQID No.: 22), was synthetically optimized to form a new plasmid (SEQID No.: 25). The plasmid pAV0125 was described in U.S. Pat. No. 6,551,996 titled "Super-active porcine growth hormone releasing hormone analog," issued on Apr. 22, 2003 with Schwartz, et al., listed as inventors ("the Schwartz '996 Patent"), which teaches application of a GHRH analog containing mutations that improve the ability to elicit the release of growth hormone. This 3,534 bp plasmid pAV0125 (SEQID No.: 22) contains a plasmid backbone with various component from different commercially available plasmids, for example, a synthetic promoter SPc5-12 (SEQID No.: 15), a modified porcine GHRH sequence (SEQID #20), and a 3'end of human growth hormone (SEQID #37). Other specific examples of optimized synthetic plasmids include an optimized wt-porcine GHRH plasmid, pAV0225 (SEQID No.: 26) FIG. 3; dog GHRH plasmid, pAV0235 (SEQID No.: 27) FIG. 4; bovine GHRH plasmid, pAV0236 (SEQID No.: 28) FIG. 5; cat GHRH plasmid, pAV0238 (SEQID No.: 29) FIG. 6; a TI-GHRH plasmid, pAV0239 (SEQID No.: 30) FIG. 7; ovine GHRH plasmid, pAV0240 (SEQID No.: 31) FIG. 8; chicken GHRH plasmid, pAV0241 (SEQID No.: 32) FIG. 9; horse GHRH plasmid, pAV0249 (SEQID No.: 33) FIG. 10. The therapeutic encoded gene for such optimized plasmids may also include species specific or optimized signal peptide sequences, and/or optimized nucleic acid sequences that encode modified GHRH molecules or functional biological equivalents thereof (e.g. see FIG. 11).

Example 2

Signal Peptides Determine Secretion of Trangene Products

Expression of the species specific GHRH under the secretory control of their species-specific signal peptides was examined in transfected mouse myoblasts (with the mouse specific construct used as a control). The plasmids used in the assay were: optimized wt-porcine GHRH plasmid with a porcine signal sequence, pAV0225 (SEQID No.: 26) FIG. 3; dog GHRH plasmid with a dog signal sequence, pAV0235 (SEQID No.: 27) FIG. 4; cat GHRH plasmid with a cat signal sequence, pAV0238 (SEQID No.: 29) FIG. 6; and TI-GHRH plasmid with a human signal sequence, pAV0239 (SEQID No.: 30) FIG. 7. Species-specific transfected cells were placed into differentiation media for 72 hours to initiate withdrawal from the cell cycle and to induce post-fusion differentiation. The media was changed to a minimal serum-free media for a 24-hours pulse. Cells were harvested 96 hours post-differentiation. Northern blot analysis showed the expected size transcripts.

Conditioned serum-free media from species-specific and control transfected myoblasts were collected and purified on C18 Sep-Columns (Peninsula Laboratories, Belmont, Calif.), which served to separate the peptide to be assayed from potentially interfering substances and to concentrate the samples to determine levels of radio-immunoassayable GHRH. Transfected cells were harvested into a specific lysis buffer and extracted using the same procedure to assay the intracellular GHRH. GHRH was measured by a heterologous human assay system (Peninsula Laboratories, Belmont, Calif.). Sensitivity of the assay is 1 pg/tube. All samples were run in the same assay. The intra-assay variability was 3%.

The relative proportion of the intracellular (I) versus secreted (S) GHRH is presented (FIG. 1). The control samples had, as expected, a report of 1I:1S. When the GHRH was under the control of the porcine specific signal peptide, the report was 1I:1.56S ($P<0.03$). When the human signal peptide was used, the proportion was 1I:2.23S ($P<0.04$), and when the dog signal was used, the report became 1I:1.43S ($P<0.04$). Interestingly, when the cat specific signal peptide was used, this report was 1I:1.33S ($P<0.3$). Thus it is possible to tightly control the relative proportion of hormone secreted from a cell versus the amount that stays into the cell. This characteristic may be very important when molecules are used to treat systemic diseases (as GH-deficiencies), versus local diseases (as diabetic ulcer). In the first case one would like to have as much newly synthesized peptide released into the circulation, while in the second case one would need a high local concentration of hormone, with minimal systemic "spilling", to avoid adverse effects.

Example 3

Synthesis Signal Peptides Determine High Secretion of Trangene Products

In order to create the synthetic signal peptides, we have first analyzed the most frequent codons in homo sapiens for "arginine": CGU=4.6%; CGC=10.7%; CGA=6.3%; CGG=11.7%; AGA=11.7%; and AGG=11.7%. We decided to use codons that are frequently used to encode for arginine, while not creating repetitive patterns in the signal peptide coding sequence. We have focused on the proline cluster in positions 21-24 "PPPP" (wild-type DNA sequence=CCA/CCT/CCC/CCT).

For the RPPP mutation the first proline was changed to arginine (RPPP DNA sequence=AGA/CCT/CCC/CCT). For the RPRP mutation, the third proline was also changed to arginine (RPRP sequence=AGA/CCT/AGG/CCT).

The changes in the DNA sequence were performed by PCR. The following primers were used:

```
RPRP Upper primer
5'-3': GCT CCA GAC CTA GGC CTT        (SEQID No.: 55)
TGA C RPRP Lower primer
5' - 3': GTC AAA GGC CTA GGT CTG      (SEQID No.: 56)
GAG C RPPP Upper primer
5' - 3': TGC TCC AGA CCT CCC CCT      (SEQID No.: 57)
TTG AC RPPP Lower primer
5' - 3': GTC AAA GGG GGA GGT CTG      (SEQID No.: 58)
GAG C Nco I Primer
5'-3' sense: CCT AGC TGC CAT GGT      (SEQID No.: 59)
GCT CTG Hind III Primer
5'-3'antisense: CCC GAT AAG CTT       (SEQID No.: 60)
TCA TTA TGC TCC
```

All primers were diluted to 50 ng/μl, and the template, the plasmid vector pAV0243 was diluted to 20 ng/μl. The PCR reaction was diluted into ReadyMix (Sigma, P4600) which includes the buffer, Taq polymerase enzyme, $MgCl_2$ and dNTP's.

Initial PCR reaction was run with upper strand primers and Hind III primers and the lower strand with NcoI primers to generate upper and lower bands containing the desired mutations. These bands were gel purified and used as template in a second PCR with the NcoI and HindIII primers.

The PCR parameters for initial cycle to generate upper and lower strand mutations were as following: a hot start cycle of 95° C. for 8 min, followed by 30 cycles of 94° C. for 30 sec, 55° C. for 30 sec, and 72° C. for 40 sec. An extension cycle completed the reaction: 72° C. for 5 min.

Upper and lower bands were excised and purified to be used as template in second round of PCR. Approximately 20 ng of each band was used for template in the second round of PCR with NcoI/Hind III primers at 50 ng each. The same PCR parameters as described above were used. This PCR generated the expected band size of approximately 220 bp. The band was ligated into Invitrogen Zero Blunt TOPO kit. Colonies were picked, mini-preps prepared, and clones were sent for sequence. A positive clone of the expected sequence was ligated into NcoI/HindIII site of backbone pAV0242.

Figure 14:
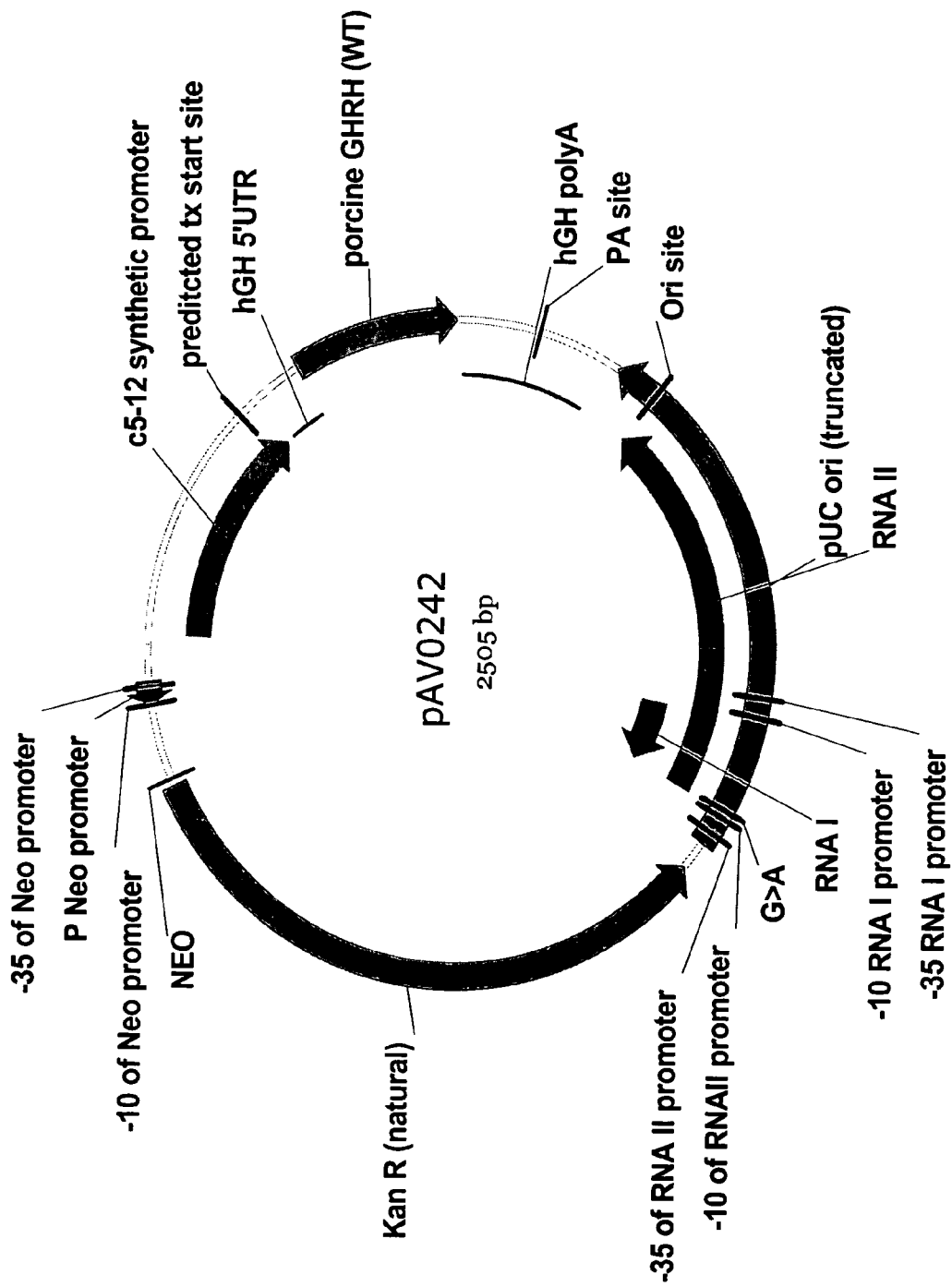
FIG. 14 shows a restriction map of pAV0242 expression plasmid.
Figure 15:
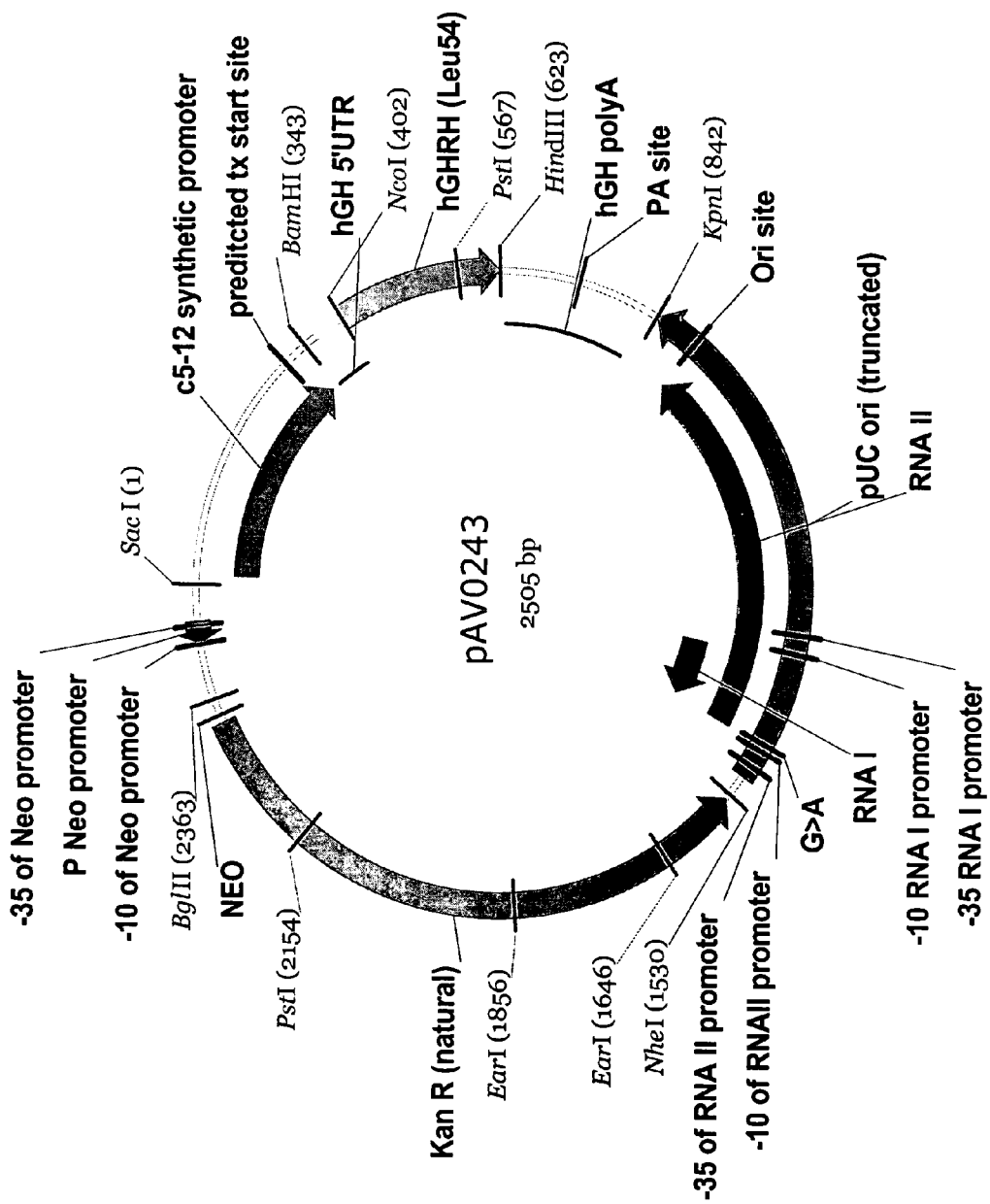
FIG. 15 shows a restriction map of pAV0243 expression plasmid.
Figure 16:
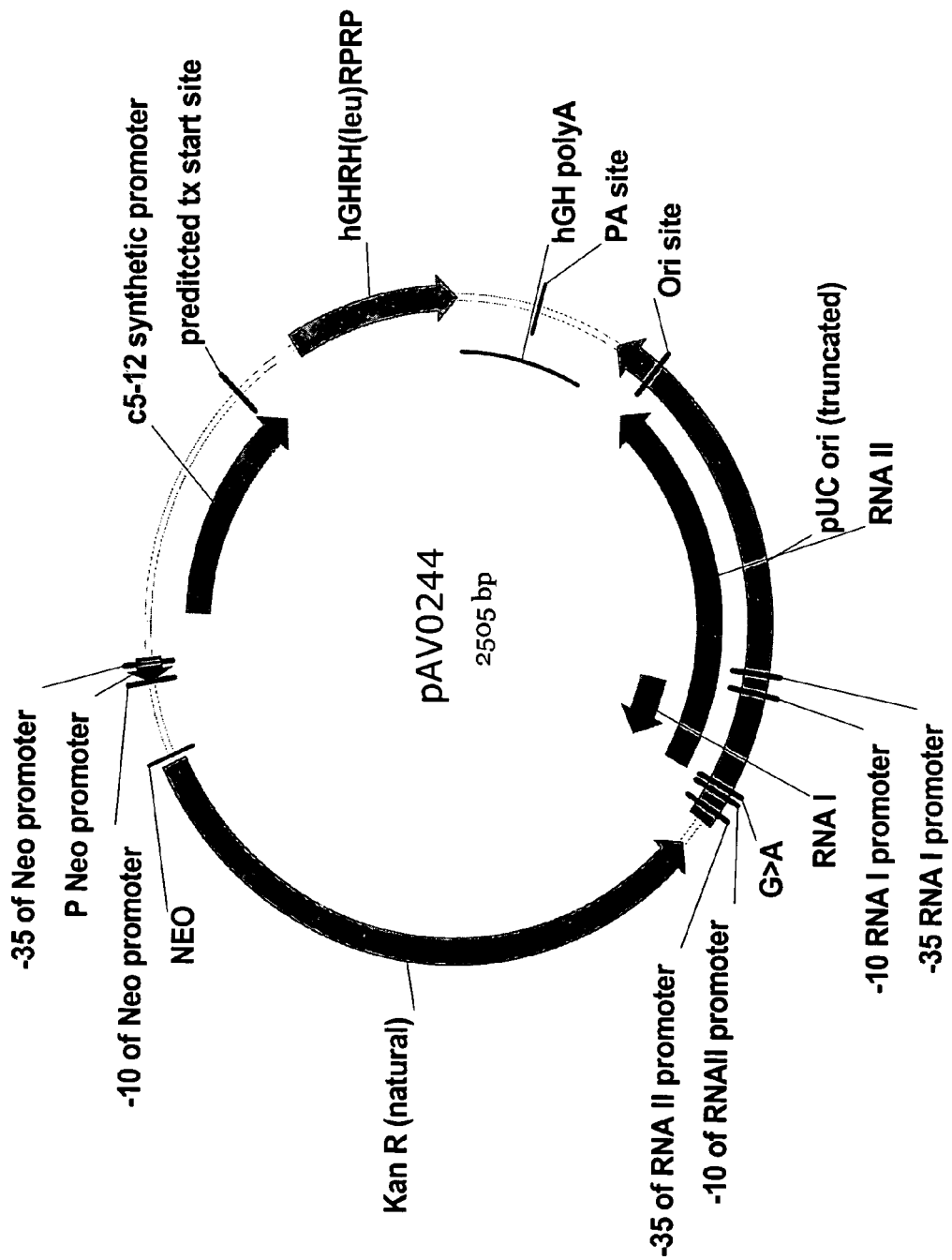
FIG. 16 shows a restriction map of pAV0244 expression plasmid.
Figure 17:
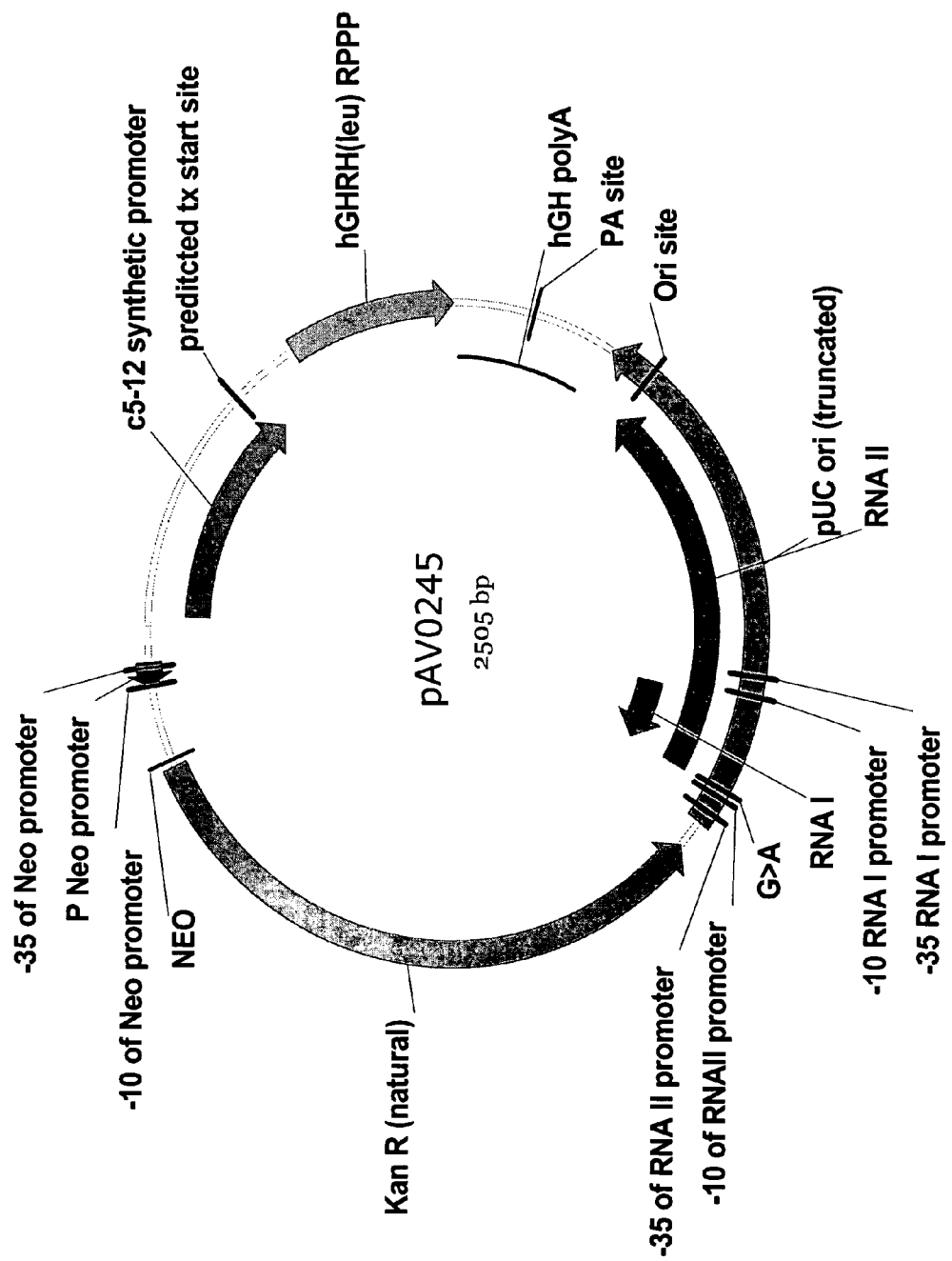
FIG. 17 shows a restriction map of pAV0245 expression plasmid.

Expression of the species specific GHRH under the secretory control of their species-specific signal peptides was examined in transfected mouse myoblasts (with the mouse specific construct used as a control). A SEAP (secreated embryonic alkaline phosphatase) expressing vetor was used as negative control. Plasmids containing the wild-type GHRH signal peptide on a new improved plasmid backbone (subject of the "High Yield Synthetic Plasmids" Application, having as inventors Ruxandra Draghia-Akli, and Melissa Pope), pAV0242 (SEQID No.: 61) (FIG. 14) and pAV0243 (SEQID No.: 62)(FIG. 15), the RPRP synthetic signal, pAV0244 (SEQID No.: 63)(FIG. 16), and the RPPP synthetic signal, pAV0245 (SEQID No.: 64)(FIG. 17) were assyed for secretory potency.

Muscle specific cells at $5 \times 10^5$ cell/plate (L6 and/or Sol8) were transfected with 4 μg plasmids containing the GHRH with the human specific or with the synthetic signal peptides. As our plasmids contain a muscle specific promoter that is active predominantly in differentiated cells, transfected cells were placed into differentiation media for 48 hours to initiate withdrawal from the cell cycle and to induce post-fusion differentiation. The media was changed to a minimal serum-free media for a 24 hours pulse. Cells were harvested 96 hours post-differentiation. Briefly, the procedure was as following: Media was collected, kept in separate tubes, spun down to eleiminate cell debris and transfered to a clean tube with 1% TFA (v/v). The cell debris pellet was saved and this tube was used for collection of cells. We added to the plates 0.5 ml homogenization buffer (50 mM HEPES, 0.1% Triton X, 4 mM EGTA, 10 mM EDTA, 15 mM Sodium pyrophosphate, 25 mM NaF, 5 mM $NaVO_4$, Protease Inhibitor cocktail (5 μl/ml Sigma P8340), water), we scraped the plates and transfered cells to corresponding tube with cell pellet. The cells were mixed well, spun down and the supernatant collected. An equal volume of 1% TFA was added to the solution. All samples were frozen at $-80°$ C. until the assay was performed. All samples were processed in the same assay. The trubes were thawed on ice, spun down to eliminate any possible debris, and the supemanatant run on C18 Sep-Columns (Peninsula Laboratories, Belmont, Calif.). Total protein levels were measured using the Bradford method (BioRad).

Conditioned serum-free media from species-specific and control transfected myoblasts were collected and purified on C18 Sep-Columns (Peninsula Laboratories, Belmont, Calif.), which served to separate the peptide to be assayed from potentially interfering substances and to concentrate the samples to determine levels of radio-immunoassayable GHRH. As described above, transfected cells were harvested into a specific lysis buffer and extracted using the same procedure to assay the intracellular GHRH. GHRH was measured by a heterologous human assay system (Peninsula Laboratories, Belmont, Calif.). Sensitivity of the assay is 1 pg/tube. All samples were run in the same assay. The intra-assay variability was 3.6%.

Figure 12:
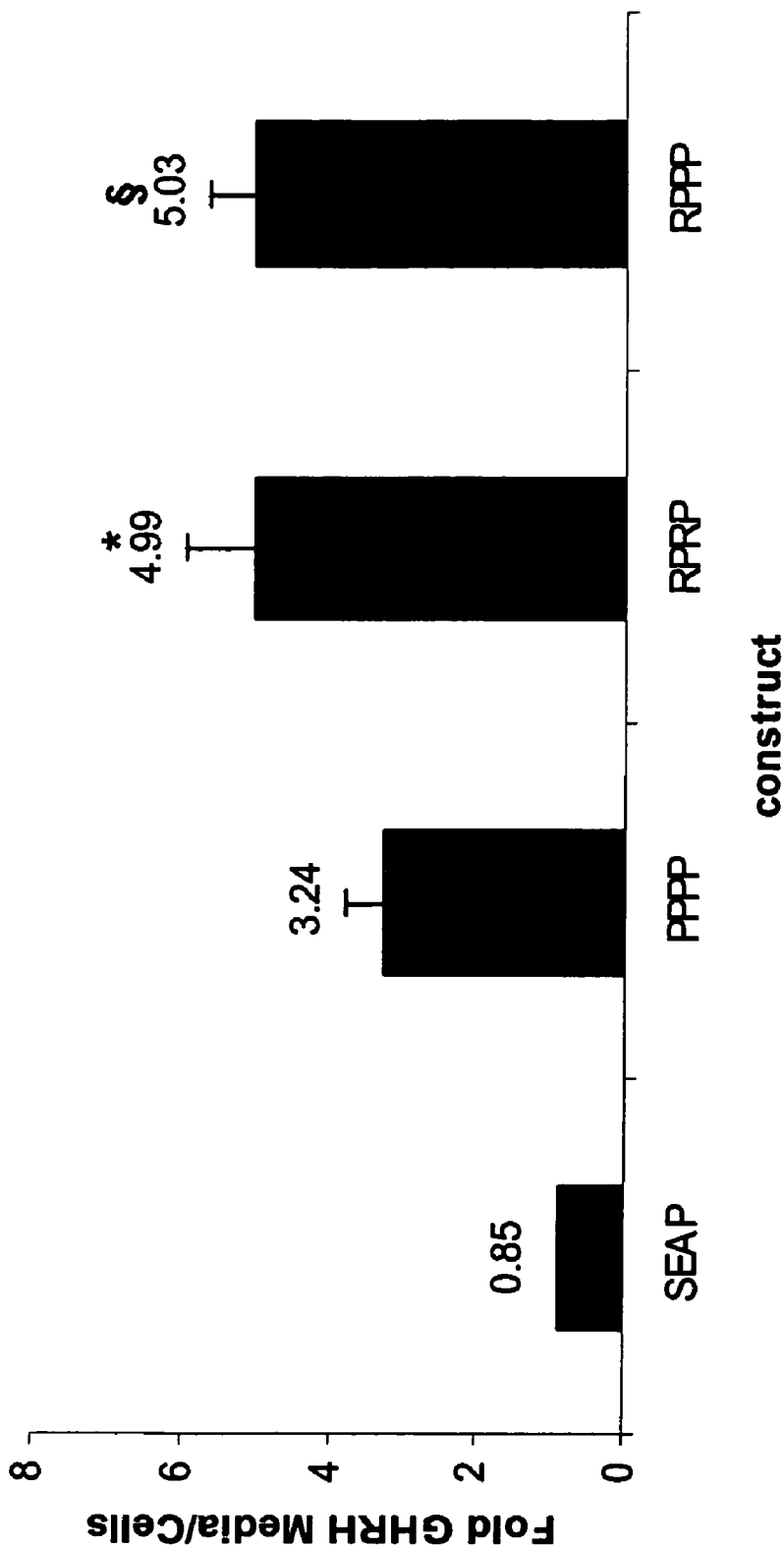
FIG. 12 shows the relative proportion of GHRH secreted from muscle cells and present into the culture media, and intracellular GHRH when the wild-type human signal peptide is compared to synthetic signal peptides RPPP and RPRP, as measured by specific radio-immunoassay.

The relative proportion of the intracellular (I) versus secreted (S) GHRH into the media is presented (FIG. 12). The control samples had, as expected, a report of approximately 1I:1S. When the GHRH was under the control of the wild type human signal peptide was used, the proportion was 1I:3.2S ($P<0.09$), and when the RPRP signal was used, the report became 1I:4.98S (*, P<0.04). Interestingly, when the RPPP specific signal peptide was used, this report was 1I:5.02S (§, P<0.002). Thus, it is possible to tightly control the relative proportion of hormone secreted from a cell versus the amount that stays into the cell. This characteristic may be very important when plasmid or other vectors that encode for a variety of molecules are used to treat systemic diseases. In this case one would like to have as much newly synthesized peptide released into the circulation, and a minimal plasmid dose to be sufficient to ensure physiological levels of the hormone, enzyme of peptide.

Figure 13:
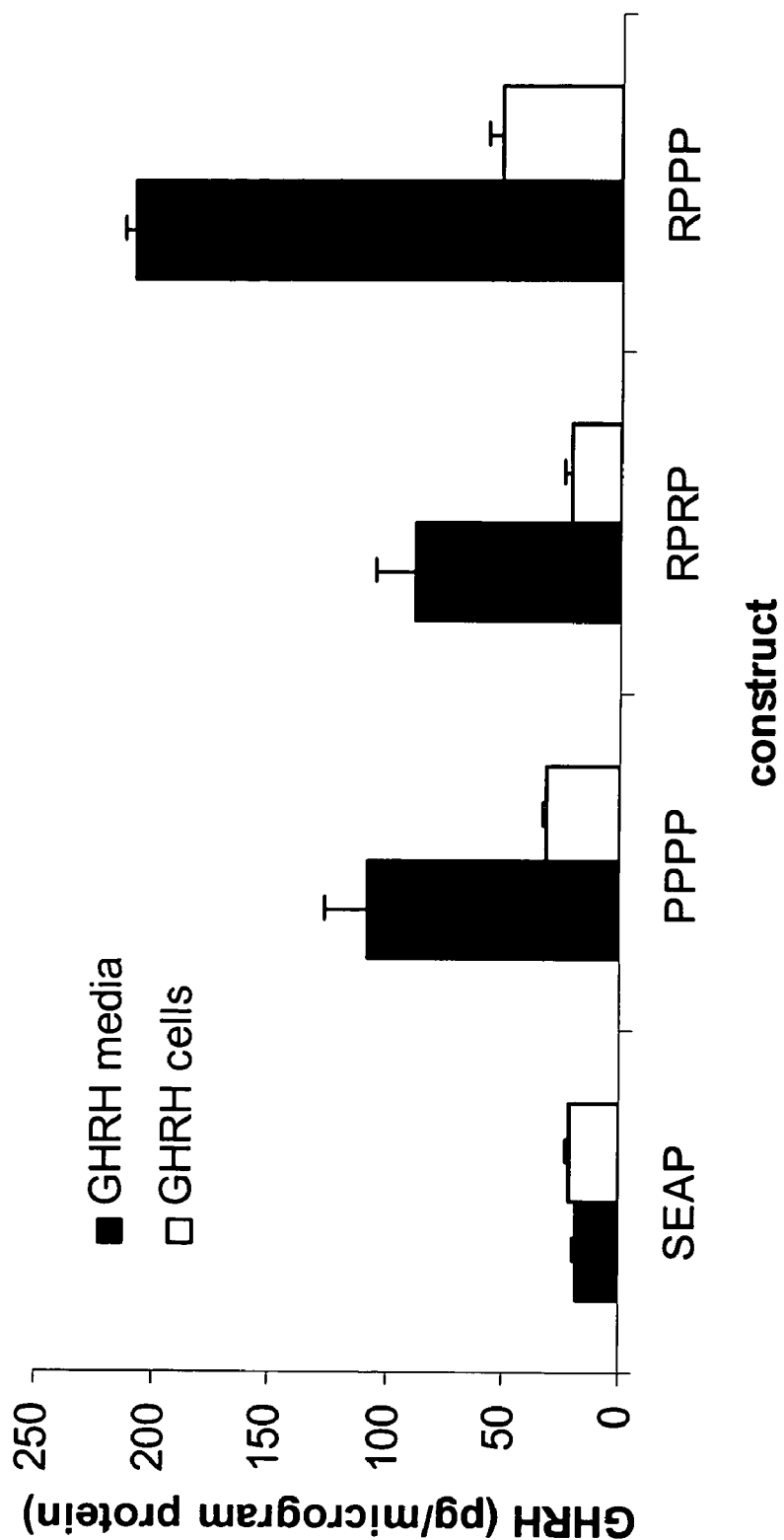
FIG. 13 shows the absolute values of GHRH secreted from muscle cells and present into the culture media, and intracellular GHRH when the wild-type human signal peptide is compared to synthetic signal peptides RPPP and RPRP, as measured by specific radio-immunoassay.

The amount of hormone produced by the cells and secreted was also measured. As shown in FIG. 13, the amount of GHRH increased two-fold over wild-type human signal peptide sequence (PPPP), when the RPPP signal peptide was included in the construct.

The embodiments provided herein illustrate that the plasmid design and incorporation of appropriate species-specific or synthetic signal peptide sequences is essential for the amount of newly synthesized protein that will be secreted versus the amount that will be kept intracellular, and that different species-specific signal peptides for the same hormone may have completely different properties. This characteristic may be used for the therapy of disease, in particular chronic disease. For instance, recent studies have demonstrated the presence of many neuropeptides and their receptors in different organs, suggesting that these peptides operate as local regulators, with effects on cell development and function, besides they known function as endocrine modulators. However, their precise physiologic roles and mechanisms of action remain largely unknown. Thus, the amount of secreted (mediating endocrine effects) versus intracellular (mediating, paracrine, autocrine effects) amount of a specific hormone is of exquisite importance.

One skilled in the art readily appreciates that this invention is well adapted to carry out the objectives and obtain the ends and advantages mentioned as well as those inherent therein. Growth hormone, growth hormone releasing hormone, analogs, plasmids, vectors, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

REFERENCES CITED

The entire content of each of the following U.S. patent documents and published references is hereby incorporated by reference.

U.S. PATENT DOCUMENTS

U.S. Pat. No. 5,847,066 issued on Dec. 8, 1998 with Coy et al. listed as inventors.
U.S. Pat. No. 5,846,936 issued on Dec. 8, 1998 with Felix et al. listed as inventors.
U.S. Pat. No. 5,792,747 issued on Aug. 11, 1998 with Schally et al. listed as inventors.
U.S. Pat. No. 5,776,901 issued on Jul. 7, 1998 with Bowers et al. listed as inventors.
U.S. Pat. No. 5,756,264 issued on May 26, 1998 with Schwartz et al. listed as inventors.
U.S. Pat. No. 5,696,089 issued on Dec. 9, 1997 with Felix et al. listed as inventors.
U.S. Pat. No. 5,486,505 issued on Jan. 23, 1996 with Bowers et al. listed as inventors.
U.S. Pat. No. 5,292,721 issued on Mar. 8, 1994 with Boyd et al. listed as inventors.
U.S. Pat. No. 5,137,872 issued on Aug. 11, 1992 with Seely et al. listed as inventors.
U.S. Pat. No. 5,134,210 issued on Jul. 28, 1992 with Boyd et al. listed as inventors.
U.S. Pat. No. 5,084,442 issued on Jan. 28, 1992 with Felix et al. listed as inventors.
U.S. Pat. No. 5,061,690 issued on Oct. 29, 1991 with Kann et al. listed as inventors.
U.S. Pat. No. 5,036,045 issued on Jul. 30, 1991 with Thorner listed as the inventor.
U.S. Pat. No. 5,023,322 issued on Jun. 11, 1991 with Kovacs et al. listed as inventors.
U.S. Pat. No. 4,839,344 issued on Jun. 13, 1989 with Bowers et al. listed as inventors.
U.S. Pat. No. 4,410,512 issued on Oct. 18, 1983 with Bowers et al. listed as inventors.
U.S. Pat. No. RE33,699 issued on Sep. 24, 1991 with Drengler listed as the inventor.
U.S. Pat. No. 4,833,166 issued on May 23, 1989 with Grosvenor et al. listed as inventors.
U.S. Pat. No. 4,228,158 issued on Oct. 14, 1980 with Momany et al. listed as inventors.
U.S. Pat. No. 4,228,156 issued on Oct. 14, 1980 with Momany et al. listed as inventors.
U.S. Pat. No. 4,226,857 issued on Oct. 7, 1980 with Momany et al. listed as inventors.
U.S. Pat. No. 4,224,316 issued on Sep. 23, 1980 with Momany et al. listed as inventors.
U.S. Pat. No. 4,223,021 issued on Sep. 16, 1980 with Momany et al. listed as inventors.
U.S. Pat. No. 4,223,020 issued on Sep. 16, 1980 with Momany et al. listed as inventors.
U.S. Pat. No. 4,223,019 issued on Sep. 16, 1980 with Momany et al. listed as inventors.
U.S. Pat. No. 5,702,359 titled "Needle electrodes for mediated delivery of drugs and genes," issued on Dec. 30, 1997, with Hofmann, et al., listed as inventors.
U.S. Pat. No. 5,439,440 titled "Electroporation system with voltage control feedback for clinical applications," issued on Aug. 8, 1995 with Hofmann listed as inventor.
PCT application WO/96/12520 titled "Electroporetic Gene and Drug Therapy by Induced Electric Fields," published on May 5, 1996 with Hofmann et al., listed as inventors.
PCT application WO/96/12006 titled "Flow Through Electroporation Apparatus and Method," published on Apr. 25, 1996 with Hofmann et al., listed as inventors.
PCT application WO/95/19805 titled "Electroporation and Iontophoresis Apparatus and Method For insertion of Drugs and genes inot Cells," published on Jul. 27, 1995 with Hofmann listed as inventor.
PCT application WO/97/07826 titled "In Vivo Electroporation of Cells," published on Mar. 6, 1997, with Nicolau et al., listed as inventors.

Other Literature Cited

Acsadi, G., G. Dickson, D. R. Love, A. Jani, F. S. Walsh, A. Gurusinghe, Wolff, J A, and K. E. Davies. 1991. Human dystrophin expression in mdx mice after intramuscular injection of DNA constructs. Nature 352:815-818.
Aihara, H. and J. Miyazaki. 1998. Gene transfer into muscle by electroporation in vivo. Nat. Biotechnol. 16:867-870.

Almendro, N., T. Bellon, C. Rius, P. Lastres, C. Langa, A. Corbi, and C. Bernabeu. 1996. Cloning of the human platelet endothelial cell adhesion molecule-1 promoter and its tissue-specific expression. Structural and functional characterization. J. Immunol. 157:5411-5421.

Aratani, Y., R. Okazaki, and H. Koyama. 1992. End extension repair of introduced targeting vectors mediated by homologous recombination in mammalian cells. Nucleic Acids Res. 20:4795-4801.

Argente, J., J. Pozo, and J. A. Chowen. 1996. The growth hormone axis: control and effects. Hormone Research 45 Suppl 1:9-11.

Arvan, P. and D. Castle. 1998. Sorting and storage during secretory granule biogenesis: looking backward and looking forward. Biochem. J. 332:593-610.

Babiuk, L. A., R. Pontarollo, S. Babiuk, B. Loehr, and van Drunen Littel-van den Hurk. 2003. Induction of immune responses by DNA vaccines in large animals. Vaccine 21:649-658.

Baertschi, A. J., D. Monnier, U. Schmidt, E. S. Levitan, S. Fakan, and A. Roatti. 2001. Acid prohormone sequence determines size, shape, and docking of secretory vesicles in atrial myocytes. Circ. Res. 89:E23-E29.

Baum, B. J., M. E. Berkman, Y. Marmary, C. M. Goldsmith, L. Baccaglini, S. Wang, R. B. Wellner, A. T. Hoque, J. C. Atkinson, H. Yamagishi, H. Kagami, A. F. Parlow, and J. Chao. 1999. Polarized secretion of transgene products from salivary glands in vivo. Hum. Gene Ther. 20;10:2789-2797.

Bercu, B. B. and R. F. Walker. 1997. Growth Hormone Secretagogues In Children With Altered Growth. Acta Paediatrica 86:102-106.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Blethen, S. L. and A. C. Rundle. 1996. Slipped capital femoral epiphysis in children treated with growth hormone. A summary of the National Cooperative Growth Study experience. Horm. Res. 46:113-116.

Bohlen, P., F. Esch, P. Brazeau, N. Ling, and R. Guillemin. 1983. Isolation and characterization of the porcine hypothalamic growth hormone releasing factor. Biochem. Biophys. Res. Commun. 116:726-734.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Breslin, M. B., I. Lindberg, S. Benjannet, J. P. Mathis, C. Lazure, and N. G. Seidah. 1993. Differential processing of proenkephalin by prohormone convertases 1(3) and 2 and furin. J. Biol. Chem. 268:27084-27093.

Butler, A. A., G. R. Ambler, B. H. Breier, D. LeRoith, C. T. Roberts, Jr., and P. D. Glucklnan. 1994. Growth hormone (GH) and insulin-like growth factor-I (IGF-I) treatment of the GH-deficient dwarf rat: differential effects on IGF-I transcription start site expression in hepatic and extrahepatic tissues and lack of effect on type I IGF receptor mRNA expression. Mol. Cell Endocrinol. 101:321-330.

Carbonelli, D. L., E. Corley, M. Seigelchifer, and J. Zorzopulos. 1999. A plasmid vector for isolation of strong promoters in Escherichia coli. FEMS Microbiol. Lett. 177:75-82.

Caroni, P. and C. Schneider. 1994. Signaling by insulin-like growth factors in paralyzed skeletal muscle: rapid induction of IGF 1 expression in muscle fibers and prevention of interstitial cell proliferation by IGF-BP5 and IGF-BP4. J. Neurosci. 14:3378-3388.

Castle, A. M. and J. D. Castle. 1998. Enhanced glycosylation and sulfation of secretory proteoglycans is coupled to the expression of a basic secretory protein. Mol. Biol. Cell 9:575-583.

Castle, A. M., A. Y. Huang, and J. D. Castle. 1998. Immunoglobulin-derived polypeptides enter the regulated secretory pathway in AtT-20 cells. FEBS Lett.20;439:341-345.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U. S. A 94:3596-3601.

Chevalier, R. L., S. Goyal, A. Kim, A. Y. Chang, D. Landau, and D. LeRoith. 2000. Renal tubulointerstitial injury from ureteral obstruction in the neonatal rat is attenuated by IGF-1. Kidney Int. 57:882-890.

Cocea, L. 1997. Duplication of a region in the multiple cloning site of a plasmid vector to enhance cloning-mediated addition of restriction sites to a DNA fragment. Biotechniques 23:814-816.

Corpas, E., S. M. Harman, M. A. Pineyro, R. Roberson, and M. R. Blackman. 1993. Continuous subcutaneous infusions of growth hormone (GH) releasing hormone 1-44 for 14 days increase GH and insulin-like growth factor-I levels in old men. J. Clin. Endocrinol. Metab. 76:134-138.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276:6937-6944.

Danko, I. and J. A. Wolff. 1994. Direct gene transfer into muscle. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Dialynas, E., H. Brown-Borg, and A. Bartke. 1999. Immune function in transgenic mice overexpressing growth hormone (GH) releasing hormone, GH or GH antagonist. Proc. Soc. Exp. Biol. Med. 221:178-183.

Dolnik, V., M. Novotny, and J. Chmelik. 1993. Electromigration behavior of poly-(L-glutamate) conformers in concentrated polyacrylamide gels. Biopolymers 33:1299-1306.

Dorsch-Hasler, K., G. M. Keil, F. Weber, M. Jasin, W. Schafffier, and U. H. Koszinowski. 1985. A long and complex enhancer activates transcription of the gene coding for the highly abundant immediate early mRNA in murine cytomegalovirus. Proc. Natl. Acad. Sci. U. S. A 82:8325-8329.

Draghia-Akli, R., K. K. Cummings, A. S. Khan, P. A. Brown, and R. H. Carpenter. 2003a. Effects of plasmid-mediated growth hormone releasing hormone supplementation in young healthy Beagle dogs. Journal of Animal Science 81:2301-2310.

Draghia-Akli, R., K. M. Ellis, L. A. Hill, P. B. Malone, and M. L. Fiorotto. 2003b. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., K. A. Hahn, G. K. King, K. Cummings, and R. H. Carpenter. 2002a. Effects Of Plasmid Mediated Growth Hormone Releasing Hormone In Severely Debilitated Dogs With Cancer. Molecular Therapy 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technology in Cancer Research & Treatment 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Dubreuil, P., D. Petitclerc, G. Pelletier, P. Gaudreau, C. Farmer, Mowles, TF, and P. Brazeau. 1990. Effect of dose and frequency of administration of a potent analog of human growth hormone-releasing factor on hormone secretion and growth in pigs. Journal of Animal Science 68:1254-1268.

Duck, S. C., H. P. Schwarz, G. Costin, R. Rapaport, S. Arslanian, A. Hayek, M. Connors, and J. Jaramillo. 1992. Subcutaneous growth hormone-releasing hormone therapy in growth hormone-deficient children: first year of therapy. J Clin Endocrinol Metab 75:1115-1120.

El Meskini, R., L. Jin, R. Marx, A. Bruzzaniti, J. Lee, R. Emeson, and R. Mains. 2001. A signal sequence is sufficient for green fluorescent protein to be routed to regulated secretory granules. Endocrinology 142:864-873.

Erikstrup, C., L. M. Pedersen, L. Heickendorff, T. Ledet, and L. M. Rasmussen. 2001. Production of hyaluronan and chondroitin sulphate proteoglycans from human arterial smooth muscle—the effect of glucose, insulin, IGF-I or growth hormone. Eur. J Endocrinol. 145:193-198.

Esch, F. S., P. Bohlen, N. C. Ling, P. E. Brazeau, W. B. Wehrenberg, M. 0. Thorner, M. J. Cronin, and R. Guillemin. 1982. Characterization of a 40 residue peptide from a human pancreatic tumor with growth hormone releasing activity. Biochem Biophys Res Comm 109:152-158.

Etherton, T. D., J. P. Wiggins, C. S. Chung, C. M. Evock, J. F. Rebhun, and P. E. Walton. 1986. Stimulation of pig growth performance by porcine growth hormone and growth hormone-releasing factor. Journal of Animal Science 63:1389-1399.

Evans, W. S., M. L. Vance, D. L. Kaiser, R. P. Sellers, J. L. Borges, T. R. Downs, L. A. Frohman, J. Rivier, W. Vale, and M. O. Thorner. 1985. Effects of intravenous, subcutaneous, and intranasal administration of growth hormone (GH)-releasing hormone-40 on serum GH concentrations in normal men. J Clin Endocrinol Metab 61:846-850.

Fernandez, V. G., L. Cacicedo, M. J. Lorenzo, M. T. los Frailes, J. I. Lara, and F. F. Sanchez. 1994. Biosynthesis of growth hormone-releasing factor by fetal rat cerebrocortical and hypothalamic cells. Peptides 15:825-828.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Foncea, R., M. Andersson, A. Ketterman, V. Blakesley, M. Sapag-Hagar, P. H. Sugden, D. LeRoith, and S. Lavandero. 1997. Insulin-like growth factor-I rapidly activates multiple signal transduction pathways in cultured rat cardiac myocytes. J. Biol. Chem. 272:19115-19124.

Frohman, L. A., T. R. Downs, E. P. Heimer, and A. M. Felix. 1989. Dipeptidylpeptidase IV and trypsin-like enzymatic degradation of human growth hormone-releasing hormone in plasma. J. Clin. Invest. 83:1533-1540.

Frohman, L. A., J. L. Thominet, C. B. Webb, M. L. Vance, H. Uderman, J. Rivier, W. Vale, and M. O. Thorner. 1984. Metabolic clearance and plasma disappearance rates of human pancreatic tumor growth hormone releasing factor in man. J. Clin. Invest. 73:1304-1311.

Fryer, A. D. and D. B. Jacoby. 1993. Effect of inflammatory cell mediators on M2 muscarinic receptors in the lungs. Life Sci. 52:529-536.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and. 1995. The insulin gene promoter. A simplified nomenclature. Diabetes 44:1002-1004.

Gesundheit, N. and J. K. Alexander. 1995. Endocrine Therapy with Recombinant Hormones and Growth Factors. Page 491 in Molecular Endocrinology: Basic Concepts and Clinical Correlations. B. D. Weintraub, ed. Raven Press, Ltd., New York.

Gopinath, R. and T. D. Etherton. 1989a. Effects of porcine growth hormone on glucose metabolism of pigs: I. Acute and chronic effects on plasma glucose and insulin status. J. Anim Sci. 67:682-688.

Gopinath, R. and T. D. Etherton. 1989b. Effects of porcine growth hormone on glucose metabolism of pigs: II. Glucose tolerance, peripheral tissue insulin sensitivity and glucose kinetics. J. Anim Sci. 67:689-697.

Gramolini, A. O., G. Belanger, and B. J. Jasmin. 2001. Distinct regions in the 3' untranslated region are responsible for targeting and stabilizing utrophin transcripts in skeletal muscle cells. J Cell Biol. 154:1173-1183.

Guillemin, R., P. Brazeau, P. Bohlen, F. Esch, N. Ling, and W. B. Wehrenberg. 1982. Growth hormone-releasing factor from a human pancreatic tumor that caused acromegaly. Science 218:585-587.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Hoess, R. H. and K. Abremski. 1985. Mechanism of strand cleavage and exchange in the Cre-lox site-specific recombination system. J. Mol. Biol. 181:351-362.

Horlick, R. A. and P. A. Benfield. 1989. The upstream muscle-specific enhancer of the rat muscle creatine kinase gene is composed of multiple elements. Mol. Cell Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jardieu, P., R. Clark, D. Mortensen, and K. Dorshkind. 1994. In vivo administration of insulin-like growth factor-I stimulates primary B lymphopoiesis and enhances lymphocyte recovery after bone marrow transplantation. J Immunol. 152:4320-4327.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

Kallio, J., U. Pesonen, U. Jaakkola, M. K. Karvonen, H. Helenius, and M. Koulu. 2003. Changes in diurnal sympathoadrenal balance and pituitary hormone secretion in subjects with Leu7Pro polymorphism in the prepro-neuropeptide Y. J. Clin. Endocrinol. Metab 88:3278-3283.

Kallio, J., U. Pesonen, M. K. Karvonen, M. Kojima, H. Hosoda, K. Kangawa, and M. Koulu. 2001. Enhanced exercise-induced GH secretion in subjects with Pro7 substitution in the prepro-NPY. J. Clin. Endocrinol. Metab 86:5348-5352.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Kelly, R. B. 1985. Pathways of protein secretion in eukaryotes. Science 230:25-32.

Khan, A. S., I. W. Anscombe, K. K. Cummings, M. A. Pope, L. C. Smith, and R. Draghia-Akli. 2003a. Effects of plasmid-mediated growth hormone releasing hormone supplementation on LL-2 adenocarcinoma in mice. Mol. Ther. 8:459-466.

Khan, A. S., I. W. Anscombe, K. K. Cummings, M. A. Pope, L. C. Smith, and R. Draghia-Akli. 2003b. Regulated plasmid-mediated growth hormone releasing hormone stimulation decreases tumor growth in nude mice. Am. J. Physiol. Endocrinol. Metab. In preparation.

Khorram, O., M. Garthwaite, and T. Golos. 2001. The influence of aging and sex hormones on expression of growth hormone-releasing hormone in the human immune system. J Clin. Endocrinol. Metab 86:3157-3161.

Klamut, H. J., L. O. Bosnoyan-Collins, R. G. Worton, P. N. Ray, and H. L. Davis. 1996. Identification of a transcriptional enhancer within muscle intron 1 of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10: 193-205.

Koo, G. C., C. Huang, R. Camacho, C. Trainor, J. T. Blake, A. Sirotina-Meisher, K. D. Schleim, T. J. Wu, K. Cheng, R. Nargund, and G. McKissick. 2001. Immune enhancing effect of a growth hormone secretagogue. J Immunol. 166: 4195-4201.

Kooistra, H. S., G. Voorhout, J. A. Mol, and A. Rijnberk. 2000. Combined pituitary hormone deficiency in german shepherd dogs with dwarfism. Domest. Anim Endocrinol. 19:177-190.

Kooistra, H. S., G. Voorhout, P. J. Selman, and A. Rijnberk. 1998. Progestin-induced growth hormone (GH) production in the treatment of dogs with congenital GH deficiency. Domest. Anim Endocrinol. 15:93-102.

Kraus, J., M. Wolte, N. Schonwetter, and V. Hollt. 1998. Alternative promoter usage and tissue specific expression of the mouse somatostatin receptor 2 gene. FEBS Lett. 428:165-170.

Lapierre, H., G. Pelletier, D. Petitclerc, P. Dubreuil, J. Morisset, P. Gaudreau, Y. Couture, and P. Brazeau. 1991. Effect of human growth hormone-releasing factor and(or) thyrotropin-releasing factor on growth, carcass composition, diet digestibility, nutrient balance, and plasma constituents in dairy calves. J Anim Sci 69:587-598.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Hamey, and D. D. Moore. 1986. Sequences required for cell-type specific thyroid hormone regulation of rat growth hormone promoter activity. J. Biol. Chem. 261:14373-14376.

Lee, M. A., K. H. Cheong, D. Shields, S. D. Park, and S. H. Hong. 2002. Intracellular trafficking and metabolic turnover of yeast prepro-alpha-factor-SRIF precursors in GH3 cells. Exp. Mol. Med. 34:285-293.

Lee, S. H., W. Wang, S. Yajima, P. A. Jose, and M. M. Mouradian. 1997. Tissue-specific promoter usage in the D1A dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Milas, C. Charnsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Liu, J. L. and D. LeRoith. 1999. Insulin-like growth factor I is essential for postnatal growth in response to growth hormone. Endocrinology 140:5178-5184.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lowe, W. L., Jr., M. Adamo, H. Werner, C. T. Roberts, Jr., and D. LeRoith. 1989. Regulation by fasting of rat insulin-like growth factor I and its receptor. Effects on gene expression and binding. J. Clin. Invest 84:619-626.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Macchi, P., I. Hemraj, B. Goetze, B. Grunewald, M. Mallardo, and M. A. Kiebler. 2003. A GFP-based System to Uncouple MRNA Transport from Translation in a Single Living Neuron. Mol. Biol. Cell 14:1570-1582.

Macejak, D. G. and P. Sarnow. 1991. Internal initiation of translation mediated by the 5' leader of a cellular mRNA. Nature 353:90-94.

Martoglio, B. 2003. Intramembrane proteolysis and post-targeting functions of signal peptides. Biochem. Soc. Trans. 31:1243-1247.

Martoglio, B. and B. Dobberstein. 1998. Signal sequences: more than just greasy peptides. Trends Cell Biol. 8:410-415.

Matsubara, H., Y. Gunji, T. Maeda, K. Tasaki, Y. Koide, T. Asano, T. Ochiai, S. Sakiyama, and M. Tagawa. 2001. Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McNally, M. A., J. S. Lebkowski, T. B. Okarma, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Moore, H. P. and R. B. Kelly. 1985. Secretory protein targeting in a pituitary cell line: differential transport of foreign secretory proteins to distinct secretory pathways. J. Cell Biol. 101:1773-1781.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J Mol. Med. 7:37-42.

Murray, R. D. and S. M. Shalet. 2000. Growth hormone: current and future therapeutic applications. Expert. Opin. Pharmacother. 1:975-990.

Naim, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhrmann, H. Liang, M. Oakley, A. Taye, B. K. Sim, and S. L. Hoffmnan. 2001. Codon optimization of gene fragments encoding Plasmodium falciparum merzoite proteins enhances DNA vaccine protein expression and immunogenicity in mice. Infect. Immun. 69:7250-7253.

Neumann, E., M. Schaefer-Ridder, Y. Wang, and P. H. Hofschneider. 1982. Gene transfer into mouse lyoma cells by electroporation in high electric fields. EMBO J. 1:841-845.

Nillni, E. A., R. Steinmetz, and O. H. Pescovitz. 1999. Post-translational processing of progrowth hormone-releasing hormone. Endocrinology 140:5817-5827.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Parks, J. S., R. W. Pfaffle, M. R. Brown, H. Abdul-Latif, and L. R. Meacham. 1995. Growth Hormone Deficiency. Page 473 in Molecular Endocrinology: Basic Concepts and Clinical Correlations. B. D. Weintraub, ed. Raven Press, Ltd., New York.

Parrizas, M. and D. LeRoith. 1997. Insulin-like growth factor-1 inhibition of apoptosis is associated with increased expression of the bcl-xL gene product. Endocrinology 138:1355-1358.

Pavasant, P., T. Shizari, and C. B. Underhill. 1996. Hyaluronan synthesis by epiphysial chondrocytes is regulated by growth hormone, insulin-like growth factor-1, parathyroid hormone and transforming growth factor-beta 1. Matrix Biol. 15:423-432.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Pinkert, C. A., D. M. Ornitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U. S. A 81:7161-7165.

Prentice, H., R. A. Kloner, T. Prigozy, T. Christensen, L. Newman, Y. Li, and L. Kedes. 1994. Tissue restricted gene expression assayed by direct DNA injection into cardiac and skeletal muscle. J Mol Cell Cardiology 26:1393-1401.

Rabinovsky, E. D. and R. Draghia-Akli. 2004. Insulin-like Growth Factor I Plasmid Therapy Promotes in Vivo Angiogenesis. Mol. Ther. 9:46-54.

Rabinovsky, E. D., G. M. Smith, D. P. Browder, H. D. Shine, and J. L. McManaman. 1992. Peripheral nerve injury down-regulates CNTF expression in adult rat sciatic nerves. J. Neurosci. Res. 31:188-192.

Rijnberk, A., H. van Herpen, J. A. Mol, and G. R. Rutteman. 1993. Disturbed release of growth hormone in mature dogs: a comparison with congenital growth hormone deficiency. Vet. Rec. 133:542-545.

Robbins, K., S. McCabe, T. Scheiner, J. Strasser, R. Clark, and P. Jardieu. 1994. Immunological effects of insulin-like growth factor-I—enhancement of immunoglobulin synthesis. Clin. Exp. Immunol. 95:337-342.

Satozawa, N., K. Takezawa, T. Miwa, S. Takahashi, M. Hayakawa, and H. Ooka. 2000. Differences in the effects of 20 K- and 22 K-hGH on water retention in rats. Growth Horm. IGF. Res. 10: 187-192.

Schaner, P., R. B. Todd, N. G. Seidah, and E. A. Nillni. 1997. Processing of prothyrotropin-releasing hormone by the family of prohormone convertases. J. Biol. Chem. 272: 19958-19968.

Skroch, P., C. Buchrnan, and M. Karin. 1993. Regulation of human and yeast metallothionein gene transcription by heavy metal ions. Prog. Clin. Biol. Res. 380:113-28.:113-128.

Smeekens, S. P., A. G. Montag, G. Thomas, C. Albiges-Rizo, R. Carroll, M. Benig, L. A. Phillips, S. Martin, S. Ohagi, P. Gardner, and 1992. Proinsulin processing by the subtilisin-related proprotein convertases flirin, PC2, and PC3. Proc. Natl. Acad. Sci. U. S. A 89:8822-8826.

Smith, L. C. and J. L. Nordstrom. 2000. Advances in plasmid gene delivery and expression in skeletal muscle. Curr. Opin. Mol. Ther. 2:150-154.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Tag, C. G., S. Mengsteab, C. Hellerbrand, F. Lammert, A. M. Gressner, and R. Weiskirchen. 2003. Analysis of the transforming growth factor-beta1 (TGF-beta1) codon 25 gene polymorphism by LightCycler-analysis in patients with chronic hepatitis C infection. Cytokine 24:173-181.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J Kidney Dis. 38:S50-S53.

Thorner, M. O., L. A. Frohman, D. A. Leong, J. Thominet, T. Downs, P. Hellmann, J. Chitwood, J. M. Vaughan, and W. Vale. 1984. Extrahypothalamic growth-hormone-releasing factor (GRF) secretion is a rare cause of acromegaly: plasma GRF levels in 177 acromegalic patients. J Clin Endocrinol Metab 59:846-849.

Thorner, M. O., M. L. Hartman, M. L. Vance, S. S. Pezzoli, and E. J. Ampleford. 1995. Neuroendocrine regulation of growth hormone secretion. Neuroscience & Biobehavioral Reviews 19:465-468.

Thorner, M. O., M. L. Vance, W. S. Evans, A. D. Rogol, J. Rivier, W. Vale, Blizzard, and RM. 1986. Clinical studies with GHRH in man. Hormone Research 24:91-98.

Tollefsen, S., M. Vordermeier, I. Olsen, A. K. Storset, L. J. Reitan, D. Clifford, D. B. Lowrie, H. G. Wiker, K. Huygen, G. Hewinson, I. Mathiesen, and T. E. Tjelle. 2003. DNA injection in combination with electroporation: a novel method for vaccination of farmed ruminants. Scand. J Immunol. 57:229-238.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, PM, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2 (XI) collagen promoter. J. Biol. Chem. 273:22861-22864.

Tsunekawa, B., M. Wada, M. Ikeda, H. Uchida, N. Naito, and M. Honjo. 1999. The 20-kilodalton (kDa) human growth hormone (hGH) differs from the 22-kDa hGH in the effect on the human prolactin receptor. Endocrinology 140:3909-3918.

Tsurumi, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion. Circulation 94:3281-3290.

Tur-Kaspa, R., L. Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

van Rooij, E. M., B. L. Haagmans, H. L. Glansbeek, Y. E. de Visser, M. G. de Bruin, W. Boersma, and A. T. Bianchi. 2000. A DNA vaccine coding for glycoprotein B of pseudorabies virus induces cell-mediated immunity in pigs and reduces virus excretion early after infection. Vet. Immunol. Immunopathol. 74:121-136.

Vance, M. L. 1990. Growth-hormone-releasing hormone. Clinical Chemistry 36:415-420.

Vance, M. L., D. L. Kaiser, W. S. Evans, R. Furlanetto, W. Vale, J. Rivier, and M. O. Thorner. 1985. Pulsatile growth hormone secretion in normal man during a continuous 24-hour infusion of human growth hormone releasing factor (1-40). Evidence for intermittent somatostatin secretion. J. Clin. Invest. 75:1584-1590.

Veldhuis, J. D., A. Iranmanesh, and A. Weltman. 1997. Elements in the pathophysiology of diminished growth hormone secretion in aging humans. Endocrine 7:41-48.

Verhelst, J., R. Abs, M. Vandeweghe, J. Mockel, J. J. Legros, G. Copinschi, C. Mahler, B. Velkeniers, L. Vanhaelst, A. Van Aelst, D. De Rijdt, A. Stevenaert, and A. Beckers. 1997. Two years of replacement therapy in adults with growth hormone deficiency. Clin. Endocrinol. (Oxf) 47:485-494.

Vilquin, J. T., P. F. Kennel, M. Patumeau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Vittone, J., M. R. Blackman, J. Busby-Whitehead, C. Tsiao, K. J. Stewart, J. Tobin, T. Stevens, M. F. Bellantoni, M. A. Rogers, G. Baumann, J. Roth, S. M. Harman, and R. G. S. Spencer. 1997. Effects of single nightly injections of growth hormone-releasing hormone (GHRH 1-29) in healthy elderly men. Metabolism: Clinical and Experimental 46:89-96.

Wada, M., H. Uchida, M. Ikeda, B. Tsunekawa, N. Naito, S. Banba, E. Tanaka, Y. Hashimoto, and M. Honjo. 1998. The 20-kilodalton (kDa) human growth hormone (hGH) differs from the 22-kDa hGH in the complex formation with cell surface hGH receptor and hGH-binding protein circulating in human plasma. Mol. Endocrinol. 12:146-156.

Wells, K. E., J. Maule, R. Kingston, K. Foster, J. McMahon, E. Damien, A. Poole, and D. J. Wells. 1997. Immune responses, not promoter inactivation, are responsible for decreased long-term expression following plasmid gene transfer into skeletal muscle. FEBS Lett. 407:164-168.

Wolff, J. A., R. W. Malone, P. Williams, W. Chong, G. Acsadi, A. Jani, Felgner, and PL. 1990. Direct gene transfer into mouse muscle in vivo. Science 247:1465-1468.

Wong, P. M., Q. Yuan, H. Chen, B. M. Sultzer, and S. W. Chung. 2001. A single point mutation at the 3'-untranslated region of Ran mRNA leads to profound changes in lipopolysaccharide endotoxin-mediated responses. J Biol. Chem. 276:33129-33138.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442:109-119.

Zhou, A. and R. E. Mains. 1994. Endoproteolytic processing of proopiomelanocortin and prohormone convertases 1 and 2 in neuroendocrine cells overexpressing prohormone convertases 1 or 2. J. Biol. Chem. 269:17440-17447.

What is claimed is:

1. A method of expressing and secreting an encoded growth-hormone-releasing-hormone ("GHRH") peptide from a cell of a subject comprising; delivering into the cell of the subject an isolated nucleic acid expression construct that comprises a promoter operatively linked to a nucleic acid sequence encoding a signal peptide coupled to the encoded GHRH peptide, wherein the encoded signal peptide has the amino acid sequence of SEQ ID NO:51 and the encoded GHRH has the amino acid sequence of SEQ ID NO:10, wherein the delivering into the cell of the subject the nucleic acid expression construct initiates expression of the encoded signal peptide and GHRH.

2. The method of claim 1, wherein delivering comprises: an electroporation method in conjunction with a carrier.

3. The method of claim 2, wherein the electroporation method comprises:
   a. penetrating a tissue in the subject with a plurality of needle electrodes, wherein the plurality of needle electrodes are arranged in a spaced relationship;
   b. introducing the nucleic acid expression construct into the tissue between the plurality of needle electrodes; and
   c. applying an electrical pulse to the plurality of needle electrodes.

4. The method of claim 3, wherein the nucleic acid expression construct is delivered in a single dose.

5. The method of claim 4, wherein the single dose comprises about a 0.01-10 mg quantity of nucleic acid expression construct.

6. The method of claim 2, wherein the carrier further comprises, a transfection-facilitating polypeptide.

7. The method of claim 6, wherein the transfection-facilitating polypeptide comprises a charged polypeptide.

8. The method of claim 7, wherein the transfection-facilitating polypeptide comprises poly-L-glutamate.

9. The method of claim 1, wherein the cell of the subject comprise diploid cells.

10. The method of claim 1, wherein the cell of the subject comprise muscle cells.

11. The method of claim 1, wherein the subject comprises human, ruminant animal, food animal, or work animal.

12. An isolated nucleic acid molecule comprising a sequence that encodes a signal peptide coupled to an encoded growth-hormone-releasing-hormone ("GHRH") peptide, wherein the encoded signal peptide has the amino acid sequence of SEQ ID NO:51 and the encoded GHRH has the amino acid sequence of SEQ ID NO:10.

13. A method of secreting an encoded growth-hormone-releasing-hormone ("GHRH") peptide from a cell of a subject comprising:
   a. penetrating a tissue in the subject with a plurality of needle electrodes, wherein the plurality of needle electrodes are arranged in a spaced relationship;
   b. introducing a single dose of an isolated nucleic acid expression construct into the tissue between the plurality of needle electrodes, wherein the single dose comprises a transfection-facilitating polypeptide; and
   c. applying an electrical pulse to the plurality of needle electrodes; wherein, the isolated nucleic acid construct comprises a promoter sequence operatively linked to a sequence that encodes a signal peptide coupled to an encoded growth-hormone-releasing-hormone ("GHRH") peptide, wherein the encoded signal peptide has the amino acid sequence of SEQ ID NO:51 and the encoded GHRH has the amino acid sequence of SEQ ID NO:10; the transfection-facilitating polypeptide comprises poly-L-glutamate; and the subject comprises human, ruminant animal, food animal, or work animal.

* * * * *

```
SEQUENCE LISTING

<160> NUMBER OF SEQ ID NOS: 64

<210> SEQ ID NO 1
<211> LENGTH: 40
<212> TYPE: PRT
<213> ORGANISM: artificial sequence
<220> FEATURE:
<223> OTHER INFORMATION: This is a HV-growth hormone releasing hormone
      ("GHRH") analog.

<400> SEQUENCE: 1

His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 2
<211> LENGTH: 40
<212> TYPE: PRT
<213> ORGANISM: Artificial sequence
<220> FEATURE:
<223> OTHER INFORMATION: This is an amino acid sequence for Pig-GHRH

<400> SEQUENCE: 2

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40
```

```
<210> SEQ ID NO 3
<211> LENGTH: 40
<212> TYPE: PRT
<213> ORGANISM: artificial sequence
<220> FEATURE:
<223> OTHER INFORMATION: This is an amino acid sequence for Bovine-GHRH

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 4
<211> LENGTH: 40
<212> TYPE: PRT
<213> ORGANISM: artificial sequence
<220> FEATURE:
<223> OTHER INFORMATION: This is an amino acid sequence for Dog-GHRH

<400> SEQUENCE: 4

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Arg Glu Gln Gly Ala
        35                  40

<210> SEQ ID NO 5
<211> LENGTH: 40
<212> TYPE: PRT
<213> ORGANISM: Artificial Sequence
<220> FEATURE:
<223> OTHER INFORMATION: This is an amino acid sequence for Cat-GHRH

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 6
<211> LENGTH: 40
<212> TYPE: PRT
<213> ORGANISM: artificial sequence
<220> FEATURE:
<223> OTHER INFORMATION: This is a TI- growth hormone releasing hormone
      ("GHRH") analog.

<400> SEQUENCE: 6

Tyr Ile Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 7
<211> LENGTH: 40
```

<212> TYPE: PRT
<213> ORGANISM: artificial sequence
<220> FEATURE:
<223> OTHER INFORMATION: This is an amino acid sequence for Ovine-GHRH

<400> SEQUENCE: 7

Tyr Ala Asp Ala Ile Phe Thr Asn Ser Tyr Arg Lys Ile Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 8
<211> LENGTH: 43
<212> TYPE: PRT
<213> ORGANISM: artificial sequence
<220> FEATURE:
<223> OTHER INFORMATION: This is an amino acid sequence for Chicken-GHRH

<400> SEQUENCE: 8

His Ala Asp Gly Ile Phe Ser Lys Ala Tyr Arg Lys Leu Leu Gly Gln
1               5                   10                  15

Leu Ser Ala Arg Asn Tyr Leu His Ser Leu Met Ala Lys Arg Val Gly
            20                  25                  30

Ser Gly Leu Gly Asp Glu Ala Glu Pro Leu Ser
        35                  40

<210> SEQ ID NO 9
<211> LENGTH: 40
<212> TYPE: PRT
<213> ORGANISM: artificial sequence
<220> FEATURE:
<223> OTHER INFORMATION: This is an amino acid sequence for Horse GHRH.
<220> FEATURE:
<221> NAME/KEY: misc_feature
<222> LOCATION: (1)..(1)
<223> OTHER INFORMATION: "X" can be any AA sequence
<220> FEATURE:
<221> NAME/KEY: misc_feature
<222> LOCATION: (30)..(40)
<223> OTHER INFORMATION: "X" can be any AA sequence

<400> SEQUENCE: 9

Xaa Ala Asp Ala Ile Phe Thr Asn Asn Tyr Arg Lys Val Leu Gly Gln
1               5                   10                  15

Leu Ser Ala Arg Lys Ile Leu Gln Asp Ile Met Ser Arg Xaa Xaa Xaa
            20                  25                  30

Xaa Xaa Xaa Xaa Xaa Xaa Xaa Xaa
        35                  40

<210> SEQ ID NO 10
<211> LENGTH: 40
<212> TYPE: PRT
<213> ORGANISM: artificial sequence
<220> FEATURE:
<223> OTHER INFORMATION: This is an amino acid sequence for human
      (1-40)-GHRH

<400> SEQUENCE: 10

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala
            35                  40

<210> SEQ ID NO 11
<211> LENGTH: 40
<212> TYPE: PRT
<213> ORGANISM: artificial sequence
<220> FEATURE:
<223> OTHER INFORMATION: This is a TV-growth hormone releasing hormone
      ("GHRH") analog.

<400> SEQUENCE: 11

Tyr Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
            35                  40

<210> SEQ ID NO 12
<211> LENGTH: 40
<212> TYPE: PRT
<213> ORGANISM: artificial sequence
<220> FEATURE:
<223> OTHER INFORMATION: This is a TA-growth hormone releasing hormone
      ("GHRH") analog.

<400> SEQUENCE: 12

Tyr Ala Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
            35                  40

<210> SEQ ID NO 13
<211> LENGTH: 44
<212> TYPE: PRT
<213> ORGANISM: artificial sequence
<220> FEATURE:
<223> OTHER INFORMATION: This is a human (1-44) growth hormone releasing
      hormone ("GHRH").

<400> SEQUENCE: 13

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40

<210> SEQ ID NO 14
<211> LENGTH: 40
<212> TYPE: PRT
<213> ORGANISM: artificial sequence
<220> FEATURE:
<223> OTHER INFORMATION: This is the artificial sequence for GHRH
      (1-40)OH.
<220> FEATURE:
<221> NAME/KEY: MISC_FEATURE
<222> LOCATION: (1)..(1)
<223> OTHER INFORMATION: Xaa at position 1 may be tyrosine, or histidine
<220> FEATURE:
<221> NAME/KEY: MISC_FEATURE
<222> LOCATION: (2)..(2)
<223> OTHER INFORMATION: Xaa at position 2 may be alanine, valine, or

```
        isoleucine.
<220> FEATURE:
<221> NAME/KEY: MISC_FEATURE
<222> LOCATION: (15)..(15)
<223> OTHER INFORMATION: Xaa at position 15 may be alanine, valine, or
        isoleucine.
<220> FEATURE:
<221> NAME/KEY: MISC_FEATURE
<222> LOCATION: (27)..(27)
<223> OTHER INFORMATION: Xaa at position 27 may be methionine, or
        leucine.
<220> FEATURE:
<221> NAME/KEY: MISC_FEATURE
<222> LOCATION: (28)..(28)
<223> OTHER INFORMATION: Xaa at position 28 may be serine or asparagine.
<220> FEATURE:
<221> NAME/KEY: MISC_FEATURE
<222> LOCATION: (34)..(34)
<223> OTHER INFORMATION: Xaa at position 34 may be arginine or serine.
<220> FEATURE:
<221> NAME/KEY: MISC_FEATURE
<222> LOCATION: (36)..(36)
<223> OTHER INFORMATION: Xaa at position 36 may be arginine or glutamine.
<220> FEATURE:
<221> NAME/KEY: MISC_FEATURE
<222> LOCATION: (38)..(38)
<223> OTHER INFORMATION: Xaa at position 38 may be arginine or glutamine

<400> SEQUENCE: 14

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Xaa Asn Xaa Glu Xaa Gly Ala
        35                  40

<210> SEQ ID NO 15
<211> LENGTH: 323
<212> TYPE: DNA
<213> ORGANISM: artificial sequence
<220> FEATURE:
<223> OTHER INFORMATION: This is a nucleic acid sequence of a eukaryotic
        promoter c5-12.

<400> SEQUENCE: 15
cggccgtccg ccctcggcac catcctcacg acacccaaat atggcgacgg gtgaggaatg      60
gtggggagtt attttagag cggtgaggaa ggtgggcagg cagcaggtgt tggcgctcta     120
aaaataactc ccgggagtta tttttagagc ggaggaatgg tggacaccca aatatggcga    180
cggttcctca cccgtcgcca tatttgggtg tccgccctcg gccggggccg cattcctggg    240
ggccgggcgg tgctcccgcc cgcctcgata aaaggctccg gggccggcgg cggcccacga    300
gctacccgga ggagcgggag gcg                                            323

<210> SEQ ID NO 16
<211> LENGTH: 190
<212> TYPE: DNA
<213> ORGANISM: artificial sequence
<220> FEATURE:
<223> OTHER INFORMATION: Nucleic acid sequence of a human growth hormone
        poly A tail.

<400> SEQUENCE: 16
gggtggcatc cctgtgaccc ctccccagtg cctctcctgg ccctggaagt tgccactcca     60
gtgcccacca gccttgtcct aataaaatta agttgcatca ttttgtctga ctaggtgtcc    120
ttctataata ttatgggggtg gaggggggtg gtatggagca aggggcaagt tgggaagaca    180
```

```
acctgtaggg                                                              190

<210> SEQ ID NO 17
<211> LENGTH: 795
<212> TYPE: DNA
<213> ORGANISM: artificial sequence
<220> FEATURE:
<223> OTHER INFORMATION: Nucleic acid sequence for antibiotic resistance
      gene kanamycin.

<400> SEQUENCE: 17
atgattgaac aagatggatt gcacgcaggt tctccggccg cttgggtgga gaggctattc        60
ggctatgact gggcacaaca gacaatcggc tgctctgatg ccgccgtgtt ccggctgtca       120
gcgcaggggc gcccggttct ttttgtcaag accgacctgt ccggtgccct gaatgaactg       180
caggacgagg cagcgcggct atcgtggctg gccacgacgg gcgttccttg cgcagctgtg       240
ctcgacgttg tcactgaagc gggaagggac tggctgctat tgggcgaagt gccggggcag       300
gatctcctgt catctcacct tgctcctgcc gagaaagtat ccatcatggc tgatgcaatg       360
cggcggctgc atacgcttga tccggctacc tgcccattcg accaccaagc gaaacatcgc       420
atcgagcgag cacgtactcg gatggaagcc ggtcttgtcg atcaggatga tctggacgaa       480
gagcatcagg ggctcgcgcc agccgaactg ttcgccaggc tcaaggcgcg catgcccgac       540
ggcgaggatc tcgtcgtgac tcatggcgat gcctgcttgc cgaatatcat ggtggaaaat       600
ggccgctttt ctggattcat cgactgtggc cggctgggtg tggcggaccg ctatcaggac       660
atagcgttgg ctacccgtga tattgctgaa gagcttggcg gcgaatgggc tgaccgcttc       720
ctcgtgcttt acggtatcgc cgctcccgat tcgcagcgca tcgccttcta tcgccttctt       780
gacgagttct tctga                                                       795

<210> SEQ ID NO 18
<211> LENGTH: 219
<212> TYPE: DNA
<213> ORGANISM: artificial sequence
<220> FEATURE:
<223> OTHER INFORMATION: Sequence for an analog porcine GHRH sequence.

<400> SEQUENCE: 18
atggtgctct gggtgttctt ctttgtgatc ctcaccctca gcaacagctc ccactgctcc        60
ccacctcccc ctttgacccct caggatgcgg cggcacgtag atgccatctt caccaacagc      120
taccggaagg tgctggccca gctgtccgcc gcaagctgc tccaggacat cctgaacagg        180
cagcagggag agaggaacca agagcaagga gcataatga                              219

<210> SEQ ID NO 19
<211> LENGTH: 246
<212> TYPE: DNA
<213> ORGANISM: artificial sequence
<220> FEATURE:
<223> OTHER INFORMATION: Sequence for an analog mouse GHRH sequence.

<400> SEQUENCE: 19
gccatggtgc tctgggtgct ctttgtgatc ctcatcctca ccagcggcag ccactgcagc        60
ctgcctccca gccctccctt caggatgcag aggcacgtgg acgccatctt caccaccaac       120
tacaggaagc tgctgagcca gctgtacgcc aggaaggtga tccaggacat catgaacaag       180
cagggcgaga ggatccagga gcagagggcc aggctgagct gataagcttg cgatgagttc       240
ttctaa                                                                 246
```

<210> SEQ ID NO 20
<211> LENGTH: 234
<212> TYPE: DNA
<213> ORGANISM: artificial sequence
<220> FEATURE:
<223> OTHER INFORMATION: Sequence for an analog rat GHRH sequence.

<400> SEQUENCE: 20

```
gccatggccc tgtgggtgtt cttcgtgctg ctgaccctga ccagcggaag ccactgcagc      60
ctgcctccca gccctccctt cagggtgcgc cggcacgccg acgccatctt caccagcagc     120
tacaggagga tcctgggcca gctgtacgct aggaagctcc tgcacgagat catgaacagg     180
cagcagggcg agaggaacca ggagcagagg agcaggttca actgataagc ttgc           234
```

<210> SEQ ID NO 21
<211> LENGTH: 29
<212> TYPE: DNA
<213> ORGANISM: artificial sequence
<220> FEATURE:
<223> OTHER INFORMATION: Nucleic acid sequence of a prokaryotic PNEO promoter.

<400> SEQUENCE: 21

```
accttaccag agggcgcccc agctggcaa                                         29
```

<210> SEQ ID NO 22
<211> LENGTH: 3534
<212> TYPE: DNA
<213> ORGANISM: artificial sequence
<220> FEATURE:
<223> OTHER INFORMATION: Plasmid vector having an analog GHRH sequence.

<400> SEQUENCE: 22

```
gttgtaaaac gacggccagt gaattgtaat acgactcact ataggcgaa ttggagctcc       60 accgcggtgg cggccgtccg ccctcggcac catcctcacg acacccaaat atggcgacgg     120
gtgaggaatg gtgggagtt atttttagag cggtgaggaa ggtgggcagg cagcaggtgt     180
tggcgctcta aaataactc ccgggagtta ttttagagc ggaggaatgg tggacaccca      240
aatatggcga cggttcctca cccgtcgcca tatttgggtg tccgccctcg gccggggccg     300
cattcctggg ggccgggcgg tgctcccgcc cgcctcgata aaaggctccg gggccggcgg     360
cggcccacga gctacccgga ggagcgggag cgccaagct ctagaactag tggatcccaa     420
ggcccaactc cccgaaccac tcagggtcct gtggacagct cacctagctg ccatggtgct     480
ctgggtgttc ttctttgtga tcctcaccct cagcaacagc tcccactgct ccccacctcc     540 cccttttgacc ctcaggatgc ggcggcacgt agatgccatc ttcaccaaca gctaccggaa     600
ggtgctggcc cagctgtccg cccgcaagct gctccaggac atcctgaaca ggcagcaggg     660
agagaggaac caagagcaag gagcataatg actgcaggaa ttcgatatca agcttatcgg     720
ggtggcatcc ctgtgacccc tccccagtgc ctctcctggc cctggaagtt gccactccag     780
tgcccaccag ccttgtccta ataaaattaa gttgcatcat tttgtctgac taggtgtcct     840
tctataatat tatggggtgg agggggtgg tatggagcaa gggcaagtt gggaagacaa      900 cctgtagggc ctgcggggtc tattgggaac caagctggag tgcagtggca caatcttggc     960
tcactgcaat ctccgcctcc tgggttcaag cgattctcct gcctcagcct cccgagttgt    1020
tgggattcca ggcatgcatg accaggctca gctaattttt gttttttgg tagagacggg    1080 gtttcaccat attggccagg ctggtctcca actcctaatc tcaggtgatc tacccacctt    1140
```

```
ggcctcccaa attgctggga ttacaggcgt gaaccactgc tcccttccct gtccttctga   1200 tttaaaata actataccag caggaggacg tccagacaca gcataggcta cctggccatg   1260
cccaaccggt gggacatttg agttgcttgc ttggcactgt cctctcatgc gttgggtcca   1320
ctcagtagat gcctgttgaa ttcgataccg tcgacctcga ggggggggccc ggtaccagct   1380 tttgttccct ttagtgaggg ttaatttcga gcttggcgta atcatggtca tagctgtttc   1440
ctgtgtgaaa ttgttatccg ctcacaattc cacacaacat acgagccgga agcataaagt   1500
gtaaagcctg gggtgcctaa tgagtgagct aactcacatt aattgcgttg cgctcactgc   1560
ccgctttcca gtcgggaaac ctgtcgtgcc agctgcatta atgaatcggc caacgcgcgg   1620
ggagaggcgg tttgcgtatt gggcgctctt ccgcttcctc gctcactgac tcgctgcgct   1680
cggtcgttcg gctgcggcga gcggtatcag ctcactcaaa ggcggtaata cggttatcca   1740
cagaatcagg ggataacgca ggaaagaaca tgtgagcaaa aggccagcaa aaggccagga   1800
accgtaaaaa ggccgcgttg ctggcgtttt tccataggct ccgcccccct gacgagcatc   1860
acaaaaatcg acgctcaagt cagaggtggc gaaacccgac aggactataa agataccagg   1920
cgtttccccc tggaagctcc ctcgtgcgct ctcctgttcc gaccctgccg cttaccggat   1980
acctgtccgc ctttctccct tcgggaagcg tggcgctttc tcatagctca cgctgtaggt   2040
atctcagttc ggtgtaggtc gttcgctcca agctgggctg tgtgcacgaa ccccccgttc   2100
agcccgaccg ctgcgcctta tccggtaact atcgtcttga gtccaacccg gtaagacacg   2160
acttatcgcc actggcagca gccactggta acaggattag cagagcgagg tatgtaggcg   2220
gtgctacaga gttcttgaag tggtggccta actacggcta cactagaaga acagtatttg   2280
gtatctgcgc tctgctgaag ccagttacct tcggaaaaag agttggtagc tcttgatccg   2340
gcaaacaaac caccgctggt agcggtggtt tttttgtttg caagcagcag attacgcgca   2400
gaaaaaaagg atctcaagaa gatcctttga tcttttctac ggggtctgac gctcagaaga   2460
actcgtcaag aaggcgatag aaggcgatgc gctgcgaatc gggagcggcg ataccgtaaa   2520
gcacgaggaa gcggtcagcc cattcgccgc caagctcttc agcaatatca cgggtagcca   2580
acgctatgtc ctgatagcgg tccgccacac ccagccggcc acagtcgatg aatccagaaa   2640
agcggccatt ttccaccatg atattcggca agcaggcatc gccatgggtc acgacgagat   2700
cctcgccgtc gggcatgcgc gccttgagcc tggcgaacag ttcggctggc gcgagcccct   2760
gatgctcttc gtccagatca tcctgatcga caagaccggc ttccatccga gtacgtgctc   2820
gctcgatgcg atgtttcgct tggtggtcga atgggcaggt agccggatca agcgtatgca   2880
gccgccgcat tgcatcagcc atgatggata ctttctcggc aggagcaagg tgagatgaca   2940
ggagatcctg ccccggcact tcgcccaata gcagccagtc ccttcccgct tcagtgacaa   3000
cgtcgagcac agctgcgcaa ggaacgcccg tcgtggccag ccacgatagc cgcgctgcct   3060
cgtcctgcag ttcattcagg gcaccggaca ggtcggtctt gacaaaaaga accgggcgcc   3120
cctgcgctga cagccggaac acggcggcat cagagcagcc gattgtctgt tgtgcccagt   3180
catagccgaa tagcctctcc acccaagcgg ccggagaacc tgcgtgcaat ccatcttgtt   3240
caatcatgcg aaacgatcct catcctgtct cttgatcaga tcttgatccc ctgcgccatc   3300
agatccttgg cggcaagaaa gccatccagt ttactttgca gggcttccca accttaccag   3360
agggcgcccc agctggcaat tccggttcgc ttgctgtcca taaaaccgcc cagtctagca   3420
actgttggga agggcgatcg gtgcgggcct cttcgctatt acgccagctg gcgaaagggg   3480
gatgtgctgc aaggcgatta agttgggtaa cgccagggtt ttcccagtca cgac          3534
```

<210> SEQ ID NO 23
<211> LENGTH: 2722
<212> TYPE: DNA
<213> ORGANISM: artificial sequence
<220> FEATURE:
<223> OTHER INFORMATION: Plasmid vector having a codon optimized mouse
      GHRH sequence

<400> SEQUENCE: 23

| | | | | | |
|---|---|---|---|---|---|
| ccaccgcggt | ggcggccgtc | cgccctcggc | accatcctca | cgacacccaa | atatggcgac | 60 |
| gggtgaggaa | tggtggggag | ttattttag | agcggtgagg | aaggtgggca | ggcagcaggt | 120 |
| gttggcgctc | taaaaataac | tcccgggagt | tattttaga | gcggaggaat | ggtggacacc | 180 |
| caaatatggc | gacggttcct | cacccgtcgc | catatttggg | tgtccgccct | cggccggggc | 240 |
| cgcattcctg | ggggccgggc | ggtgctcccg | cccgcctcga | taaaaggctc | cggggccggc | 300 |
| ggcggcccac | gagctacccg | gaggagcggg | aggcgccaag | cggatcccaa | ggcccaactc | 360 |
| cccgaaccac | tcagggtcct | gtggacagct | cacctagctg | ccatggtgct | ctgggtgctc | 420 |
| tttgtgatcc | tcatcctcac | cagcggcagc | cactgcagcc | tgcctcccag | ccctcccttc | 480 |
| aggatgcaga | ggcacgtgga | cgccatcttc | accaccaact | acaggaagct | gctgagccag | 540 |
| ctgtacgcca | ggaaggtgat | ccaggacatc | atgaacaagc | agggcgagag | gatccaggag | 600 |
| cagagggcca | ggctgagctg | ataagcttat | cggggtggca | tccctgtgac | ccctccccag | 660 |
| tgcctctcct | ggccctggaa | gttgccactc | cagtgcccac | cagccttgtc | ctaataaaat | 720 |
| taagttgcat | cattttgtct | gactaggtgt | ccttctataa | tattatgggg | tggaggggggg | 780 |
| tggtatggag | caaggggcaa | gttgggaaga | caacctgtag | ggctcgaggg | ggggcccggt | 840 |
| accagctttt | gttcccttta | gtgagggtta | atttcgagct | tggtcttccg | cttcctcgct | 900 |
| cactgactcg | ctgcgctcgg | tcgttcggct | gcggcgagcg | gtatcagctc | actcaaaggc | 960 |
| ggtaatacgg | ttatccacag | aatcagggga | taacgcagga | aagaacatgt | gagcaaaagg | 1020 |
| ccagcaaaag | gccaggaacc | gtaaaaaggc | cgcgttgctg | gcgttttttcc | ataggctccg | 1080 |
| cccccctgac | gagcatcaca | aaaatcgacg | ctcaagtcag | aggtggcgaa | acccgacagg | 1140 |
| actataaaga | taccaggcgt | ttccccctgg | aagctccctc | gtgcgctctc | ctgttccgac | 1200 |
| cctgccgctt | accggatacc | tgtccgcctt | tctcccttcg | ggaagcgtgg | cgctttctca | 1260 |
| tagctcacgc | tgtaggtatc | tcagttcggt | gtaggtcgtt | cgctccaagc | tgggctgtgt | 1320 |
| gcacgaaccc | cccgttcagc | ccgaccgctg | cgccttatcc | ggtaactatc | gtcttgagtc | 1380 |
| caacccggta | agacacgact | tatcgccact | ggcagcagcc | actggtaaca | ggattagcag | 1440 |
| agcgaggtat | gtaggcggtg | ctacagagtt | cttgaagtgg | tggcctaact | acggctacac | 1500 |
| tagaagaaca | gtatttggta | tctgcgctct | gctgaagcca | gttaccttcg | gaaaaagagt | 1560 |
| tggtagctct | tgatccggca | aacaaaccac | cgctggtagc | ggtggttttt | ttgtttgcaa | 1620 |
| gcagcagatt | acgcgcagaa | aaaaaggatc | tcaagaagat | cctttgatct | tttctacggg | 1680 |
| gtctgacgct | cagctagcgc | tcagaagaac | tcgtcaagaa | ggcgatagaa | ggcgatgcgc | 1740 |
| tgcgaatcgg | gagcggcgat | accgtaaagc | acgaggaagc | ggtcagccca | ttcgccgcca | 1800 |
| agctcttcag | caatatcacg | ggtagccaac | gctatgtcct | gatagcggtc | cgccacaccc | 1860 |
| agccggccac | agtcgatgaa | tccagaaaag | cggccatttt | ccaccatgat | attcggcaag | 1920 |
| caggcatcgc | catgagtcac | gacgagatcc | tcgccgtcgg | gcatgcgcgc | cttgagcctg | 1980 |
| gcgaacagtt | cggctggcgc | gagcccctga | tgctcttcgt | ccagatcatc | ctgatcgaca | 2040 |

-continued

| | |
|---|---|
| agaccggctt ccatccgagt acgtgctcgc tcgatgcgat gtttcgcttg gtggtcgaat | 2100 |
| gggcaggtag ccggatcaag cgtatgcagc cgccgcattg catcagccat gatggatact | 2160 |
| ttctcggcag gagcaaggtg agatgacagg agatcctgcc ccggcacttc gcccaatagc | 2220 |
| agccagtccc ttcccgcttc agtgacaacg tcgagcacag ctgcgcaagg aacgcccgtc | 2280 |
| gtggccagcc acgatagccg cgctgcctcg tcctgcagtt cattcagggc accggacagg | 2340 |
| tcggtcttga caaaaagaac cgggcgcccc tgcgctgaca gccggaacac ggcggcatca | 2400 |
| gagcagccga ttgtctgttg tgcccagtca tagccgaata gcctctccac ccaagcggcc | 2460 |
| ggagaacctg cgtgcaatcc atcttgttca atcatgcgaa acgatcctca tcctgtctct | 2520 |
| tgatcagatc ttgatcccct gcgccatcag atccttggcg gcaagaaagc catccagttt | 2580 |
| actttgcagg gcttcccaac cttaccagag ggcgcccag ctggcaattc cggttcgctt | 2640 |
| gctgtccata aaaccgccca gtctagcaac tgttgggaag ggcgatcgtg taatacgact | 2700 |
| cactataggg cgaattggag ct | 2722 |

<210> SEQ ID NO 24
<211> LENGTH: 2725
<212> TYPE: DNA
<213> ORGANISM: artificial sequence
<220> FEATURE:
<223> OTHER INFORMATION: Plasmid vector having a codon optimized rat
    GHRH sequence

<400> SEQUENCE: 24

| | |
|---|---|
| ccaccgcggt ggcggccgtc cgccctcggc accatcctca cgacacccaa atatggcgac | 60 |
| gggtgaggaa tggtggggag ttatttttag agcggtgagg aaggtgggca ggcagcaggt | 120 |
| gttggcgctc taaaaataac tcccgggagt tatttttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc cggggccggc | 300 |
| ggcggcccac gagctacccg gaggagcggg aggcgccaag cggatcccaa ggcccaactc | 360 |
| cccgaaccac tcagggtcct gtggacagct cactagctg ccatggccct gtgggtgttc | 420 |
| ttcgtgctgc tgaccctgac cagcggaagc cactgcagcc tgcctcccag ccctccctttc | 480 |
| agggtgcgcc ggcacgccga cgccatcttc accagcagct acaggaggat cctgggccag | 540 |
| ctgtacgcta ggaagctcct gcacgagatc atgaacaggc agcagggcga gaggaaccag | 600 |
| gagcagagga gcaggttcaa ctgataagct tatcggggtg gcatccctgt gacccctccc | 660 |
| cagtgcctct cctggccctg gaagttgcca ctccagtgcc caccagcctt gtcctaataa | 720 |
| aattaagttg catcattttg tctgactagg tgtccttcta taatattatg gggtggaggg | 780 |
| gggtggtatg gagcaagggg caagttggga agacaacctg tagggctcga ggggggcccc | 840 |
| ggtaccagct tttgttcct ttagtgaggg ttaatttcga gcttggtctt ccgcttcctc | 900 |
| gctcactgac tcgctgcgct cggtcgttcg gctgcggcga gcggtatcag ctcactcaaa | 960 |
| ggcggtaata cggttatcca cagaatcagg ggataacgca ggaaagaaca tgtgagcaaa | 1020 |
| aggccagcaa aaggccagga accgtaaaaa ggccgcgttg ctggcgtttt tccataggct | 1080 |
| ccgcccccct gacgagcatc acaaaaatcg acgctcaagt cagaggtggc gaaacccgac | 1140 |
| aggactataa agataccagg cgtttccccc tggaagctcc ctcgtgcgct ctcctgttcc | 1200 |
| gaccctgccg cttaccggat acctgtccgc ctttctccct tcgggaagcg tggcgctttc | 1260 |
| tcatagctca cgctgtaggt atctcagttc ggtgtaggtc gttcgctcca agctgggctg | 1320 |

```
tgtgcacgaa ccccccgttc agcccgaccg ctgcgcctta tccggtaact atcgtcttga    1380
gtccaacccg gtaagacacg acttatcgcc actggcagca gccactggta acaggattag    1440
cagagcgagg tatgtaggcg gtgctacaga gttcttgaag tggtggccta actacggcta    1500
cactagaaga acagtatttg gtatctgcgc tctgctgaag ccagttacct tcggaaaaag    1560
agttggtagc tcttgatccg gcaaacaaac caccgctggt agcggtggtt ttttgtttg    1620 caagcagcag attacgcgca gaaaaaagg atctcaagaa gatcctttga tcttttctac    1680
ggggtctgac gctcagctag cgctcagaag aactcgtcaa gaaggcgata aaggcgatg    1740 cgctgcgaat cgggagcggc gataccgtaa agcacgagga agcggtcagc ccattcgccg    1800
ccaagctctt cagcaatatc acgggtagcc aacgctatgt cctgatagcg gtccgccaca    1860
cccagccggc cacagtcgat gaatccagaa agcggccat tttccaccat gatattcggc    1920
aagcaggcat cgccatgagt cacgacgaga tcctcgccgt cgggcatgcg cgccttgagc    1980
ctggcgaaca gttcggctgg cgcgagcccc tgatgctctt cgtccagatc atcctgatcg    2040
acaagaccgg cttccatccg agtacgtgct cgctcgatgc gatgtttcgc ttggtggtcg    2100
aatgggcagg tagccggatc aagcgtatgc agccgccgca ttgcatcagc catgatggat    2160
actttctcgg caggagcaag gtgagatgac aggagatcct gccccggcac ttcgcccaat    2220
agcagccagt cccttcccgc ttcagtgaca acgtcgagca gctgcgca aggaacgccc    2280 gtcgtggcca gccacgatag ccgcgctgcc tcgtcctgca gttcattcag ggcaccggac    2340
aggtcggtct tgacaaaaag aaccgggcgc ccctgcgctg acagccggaa cacggcggca    2400
tcagagcagc cgattgtctg ttgtgcccag tcatagccga atagcctctc cacccaagcg    2460
gccggagaac ctgcgtgcaa tccatcttgt tcaatcatgc gaaacgatcc tcatcctgtc    2520
tcttgatcag atcttgatcc cctgcgccat cagatccttg gcggcaagaa agccatccag    2580
tttactttgc agggcttccc aaccttacca gagggcgccc cagctggcaa ttccggttcg    2640
cttgctgtcc ataaaaccgc ccagtctagc aactgttggg aagggcgatc gtgtaatacg    2700
actcactata gggcgaattg gagct                                          2725
```

<210> SEQ ID NO 25
<211> LENGTH: 2725
<212> TYPE: DNA
<213> ORGANISM: artificial sequence
<220> FEATURE:
<223> OTHER INFORMATION: This is the codon optimized HV-GHRH expression plasmid.

<400> SEQUENCE: 25

```
ccaccgcggt ggcggccgtc cgccctcggc accatcctca cgacacccaa atatggcgac      60
gggtgaggaa tggtggggag ttatttttag agcggtgagg aaggtgggca ggcagcaggt    120 gttgcgctc taaaataac tcccgggagt tatttttaga gcggaggaat ggtggacacc      180
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct cccacctcc cctttgacc     480 ctcaggatgc ggcggcacgt agatgccatc ttcaccaaca gctaccggaa ggtgctggcc    540
cagctgtccg cccgcaagct gctccaggac atcctgaaca ggcagcaggg agagaggaac    600
```

-continued

```
caagagcaag gagcataatg acatcaagct tatcggggtg gcatccctgt gaccccctccc    660
cagtgcctct cctggccctg gaagttgcca ctccagtgcc caccagcctt gtcctaataa    720
aattaagttg catcattttg tctgactagg tgtccttcta taatattatg gggtggaggg    780
gggtggtatg gagcaagggg caagttggga agacaacctg tagggctcga gggggggccc    840
ggtaccagct tttgttccct ttagtgaggg ttaatttcga gcttggtctt ccgcttcctc    900
gctcactgac tcgctgcgct cggtcgttcg gctgcggcga cggtatcag ctcactcaaa     960
ggcggtaata cggttatcca gaatcagg ggataacgca ggaaagaaca tgtgagcaaa     1020
aggccagcaa aaggccagga accgtaaaaa ggccgcgttg ctggcgtttt tccataggct    1080
ccgcccccct gacgagcatc acaaaaatcg acgctcaagt cagaggtggc gaaacccgac    1140
aggactataa agataccagg cgtttccccc tggaagctcc ctcgtgcgct ctcctgttcc    1200
gaccctgccg cttaccggat acctgtccgc ctttctccct tcgggaagcg tggcgctttc    1260
tcatagctca cgctgtaggt atctcagttc ggtgtaggtc gttcgctcca agctgggctg    1320
tgtgcacgaa ccccccgttc agcccgaccg ctgcgcctta tccggtaact atcgtcttga    1380
gtccaacccg gtaagacacg acttatcgcc actggcagca gccactggta acaggattag    1440
cagagcgagg tatgtaggcg gtgctacaga gttcttgaag tggtggccta actacggcta    1500
cactagaaga acagtatttg gtatctgcgc tctgctgaag ccagttacct tcggaaaaag    1560
agttggtagc tcttgatccg gcaaacaaac caccgctggt agcggtggtt ttttgtttta    1620
caagcagcag attacgcgca gaaaaaaagg atctcaagaa gatcctttga tcttttctac    1680
ggggtctgac gctcagctag cgctcagaag aactcgtcaa gaaggcgata gaaggcgatg    1740
cgctgcgaat cgggagcggc gataccgtaa agcacgagga agcggtcagc ccattcgccg    1800
ccaagctctt cagcaatatc acgggtagcc aacgctatgt cctgatagcg gtccgccaca    1860
cccagccggc cacagtcgat gaatccagaa aagcggccat tttccaccat gatattcggc    1920
aagcaggcat cgccatgagt cacgacgaga tcctcgccgt cgggcatgcg cgccttgagc    1980
ctggcgaaca gttcggctgg cgcgagcccc tgatgctctt cgtccagatc atcctgatcg    2040
acaagaccgg cttccatccg agtacgtgct cgctcgatgc gatgtttcgc ttggtggtcg    2100
aatgggcagg tagccggatc aagcgtatgc agccgccgca ttgcatcagc catgatggat    2160
actttctcgg caggagcaag gtgagatgac aggagatcct gccccggcac ttcgcccaat    2220
agcagccagt cccttcccgc ttcagtgaca acgtcgagca cagctgcgca aggaacgccc    2280
gtcgtggcca gccacgatag ccgcgctgcc tcgtcctgca gttcattcag ggcaccggac    2340
aggtcggtct tgacaaaaag aaccgggcgc ccctgcgctg acagccggaa cacggcggca    2400
tcagagcagc cgattgtctg ttgtgcccag tcatagccga atagcctctc cacccaagcg    2460
gccggagaac ctgcgtgcaa tccatcttgt tcaatcatgc gaaacgatcc tcatcctgtc    2520
tcttgatcag atcttgatcc cctgcgccat cagatccttg gcggcaagaa agccatccag    2580
tttactttgc agggcttccc aaccttacca gagggcgccc cagctggcaa ttccggttcg    2640
cttgctgtcc ataaaaccgc ccagtctagc aactgttggg aagggcgatc gtgtaataCG    2700
actcactata gggcgaattg gagct                                         2725
```

<210> SEQ ID NO 26
<211> LENGTH: 2721
<212> TYPE: DNA
<213> ORGANISM: artificial sequence
<220> FEATURE:

<223> OTHER INFORMATION: This is the codon optimized pig-GHRH expression plasmid.

<400> SEQUENCE: 26

| | | | | | |
|---|---|---|---|---|---|
| ccaccgcggt | ggcggccgtc | cgccctcggc | accatcctca | cgacacccaa | atatggcgac | 60 |
| gggtgaggaa | tggtggggag | ttattttttag | agcggtgagg | aaggtgggca | ggcagcaggt | 120 |
| gttggcgctc | taaaaataac | tcccgggagt | tattttttaga | gcggaggaat | ggtgacacc | 180 |
| caaatatggc | gacggttcct | cacccgtcgc | catatttggg | tgtccgccct | cggccggggc | 240 |
| cgcattcctg | ggggccgggc | ggtgctcccg | cccgcctcga | taaaaggctc | cggggccggc | 300 |
| ggcggcccac | gagctacccg | gaggagcggg | aggcgccaag | cggatcccaa | ggcccaactc | 360 |
| cccgaaccac | tcagggtcct | gtggacagct | cacctagctg | ccatggtgct | ctgggtgttc | 420 |
| ttctttgtga | tcctcaccct | cagcaacagc | tcccactgct | ccccacctcc | cccttgacc | 480 |
| ctcaggatgc | ggcggtatgc | agatgccatc | ttcaccaaca | gctaccggaa | ggtgctgggc | 540 |
| cagctgtccg | cccgcaagct | gctccaggac | atcatgagca | ggcagcaggg | agagaggaac | 600 |
| caagagcaag | gagcataatg | aaagcttatc | ggggtggcat | ccctgtgacc | cctccccagt | 660 |
| gcctctcctg | gccctggaag | ttgccactcc | agtgcccacc | agccttgtcc | taataaaatt | 720 |
| aagttgcatc | attttgtctg | actaggtgtc | cttctataat | attatggggt | ggagggggt | 780 |
| ggtatggagc | aaggggcaag | ttgggaagac | aacctgtagg | gctcgagggg | gggcccggta | 840 |
| ccagcttttg | ttcccttttag | tgaggttaa | tttcgagctt | ggtcttccgc | ttcctcgctc | 900 |
| actgactcgc | tgcgctcggt | cgttcggctg | cggcgagcgg | tatcagctca | ctcaaaggcg | 960 |
| gtaatacggt | tatccacaga | atcaggggat | aacgcaggaa | agaacatgtg | agcaaaaggc | 1020 |
| cagcaaaagg | ccaggaaccg | taaaaaggcc | gcgttgctgg | cgtttttcca | taggctccgc | 1080 |
| ccccctgacg | agcatcacaa | aaatcgacgc | tcaagtcaga | ggtggcgaaa | cccgacagga | 1140 |
| ctataaagat | accaggcgtt | tccccctgga | agctccctcg | tgcgctctcc | tgttccgacc | 1200 |
| ctgccgctta | ccggatacct | gtccgccttt | ctcccttcgg | gaagcgtggc | gctttctcat | 1260 |
| agctcacgct | gtaggtatct | cagttcggtg | taggtcgttc | gctccaagct | gggctgtgtg | 1320 |
| cacgaacccc | ccgttcagcc | cgaccgctgc | gccttatccg | gtaactatcg | tcttgagtcc | 1380 |
| aacccggtaa | gacacgactt | atcgccactg | gcagcagcca | ctggtaacag | gattagcaga | 1440 |
| gcgaggtatg | taggcggtgc | tacagagttc | ttgaagtggt | ggcctaacta | cggctacact | 1500 |
| agaagaacag | tatttggtat | ctgcgctctg | ctgaagccag | ttaccttcgg | aaaaagagtt | 1560 |
| ggtagctctt | gatccggcaa | acaaaccacc | gctggtagcg | gtggtttttt | tgtttacaag | 1620 |
| cagcagatta | cgcgcagaaa | aaaaggatct | caagaagatc | ctttgatctt | ttctacgggg | 1680 |
| tctgacgctc | agctagcgct | cagaagaact | cgtcaagaag | gcgatagaag | gcgatgcgct | 1740 |
| gcgaatcggg | agcggcgata | ccgtaaagca | cgaggaagcg | gtcagcccat | tcgccgccaa | 1800 |
| gctcttcagc | aatatcacgg | gtagccaacg | ctatgtcctg | atagcggtcc | gccacaccca | 1860 |
| gccggccaca | gtcgatgaat | ccagaaaagc | ggccattttc | caccatgata | ttcggcaagc | 1920 |
| aggcatcgcc | atgagtcacg | acgagatcct | cgccgtcggg | catgcgcgcc | ttgagcctgg | 1980 |
| cgaacagttc | ggctggcgcg | agcccctgat | gctcttcgtc | cagatcatcc | tgatcgacaa | 2040 |
| gaccggcttc | catccgagta | cgtgctcgct | cgatgcgatg | tttcgcttgg | tggtcgaatg | 2100 |
| ggcaggtagc | cggatcaagc | gtatgcagcc | gccgcattgc | atcagccatg | atggatactt | 2160 |
| tctcggcagg | agcaaggtga | gatgacagga | gatcctgccc | cggcacttcg | cccaatagca | 2220 |

-continued

| | | |
|---|---|---|
| gccagtccct tcccgcttca gtgacaacgt cgagcacagc tgcgcaagga acgcccgtcg | 2280 |
| tggccagcca cgatagccgc gctgcctcgt cctgcagttc attcagggca ccggacaggt | 2340 |
| cggtcttgac aaaaagaacc gggcgcccct gcgctgacag ccggaacacg gcggcatcag | 2400 |
| agcagccgat tgtctgttgt gcccagtcat agccgaatag cctctccacc caagcggccg | 2460 |
| gagaacctgc gtgcaatcca tcttgttcaa tcatgcgaaa cgatcctcat cctgtctctt | 2520 |
| gatcagatct tgatcccctg cgccatcaga tccttggcgg caagaaagcc atccagttta | 2580 |
| ctttgcaggg cttcccaacc ttaccagagg gcgcccagc tggcaattcc ggttcgcttg | 2640 |
| ctgtccataa aaccgcccag tctagcaact gttgggaagg gcgatcgtgt aatacgactc | 2700 |
| actatagggc gaattggagc t | 2721 |

<210> SEQ ID NO 27
<211> LENGTH: 2716
<212> TYPE: DNA
<213> ORGANISM: artificial sequence
<220> FEATURE:
<223> OTHER INFORMATION: This is the codon optimized dog-GHRH expression plasmid.

<400> SEQUENCE: 27

| | | |
|---|---|---|
| ccaccgcggt ggcggccgtc cgccctcggc accatcctca cgacacccaa atatggcgac | 60 |
| gggtgaggaa tggtggggag ttatttttag agcggtgagg aaggtgggca ggcagcaggt | 120 |
| gttggcgctc taaaataac tcccgggagt tattttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc ggggccggc | 300 |
| ggcggcccac gagctacccg gaggagcggg aggcgccaag cggatcccaa ggcccaactc | 360 |
| cccgaaccac tcagggtcct gtggacagct cacctagctg ccatggtgct ctgggtgttc | 420 |
| ttcctggtga tcctcaccct cagcagtggt tcccactctt ccccgccatc cctgccatc | 480 |
| agaatccctc ggtatgcaga cgccatcttc accaacagct accggaaggt gctgggccag | 540 |
| ctgtccgccc gcaagctcct scaggacatc atgagccggc agcagggaga gagaaaccgg | 600 |
| gagcaaggag catagtaagc ttatcggggt ggcatccctg tgacccctcc ccagtgcctc | 660 |
| tcctggccct ggaagttgcc actccagtgc ccaccagcct tgtcctaata aaattaagtt | 720 |
| gcatcatttt gtctgactag gtgtccttct ataatattat ggggtggagg gggtggtat | 780 |
| ggagcaaggg gcaagttggg aagacaacct gtagggctcg agggggggcc cggtaccagc | 840 |
| ttttgttccc tttagtgagg gttaatttcg agcttggtct tccgcttcct cgctcactga | 900 |
| ctcgctgcgc tcggtcgttc ggctgcggcg agcggtatca gctcactcaa aggcggtaat | 960 |
| acggttatcc acagaatcag gggataacgc aggaaagaac atgtgagcaa aaggccagca | 1020 |
| aaaggccagg aaccgtaaaa aggccgcgtt gctggcgttt ttccataggc tccgccccc | 1080 |
| tgacgagcat cacaaaaatc gacgctcaag tcagaggtgg cgaaacccga caggactata | 1140 |
| aagataccag gcgtttcccc ctggaagctc cctcgtgcgc tctcctgttc cgaccctgcc | 1200 |
| gcttaccgga tacctgtccg cctttctccc ttcgggaagc gtggcgcttt ctcatagctc | 1260 |
| acgctgtagg tatctcagtt cggtgtaggt cgttcgctcc aagctgggct gtgtgcacga | 1320 |
| acccccccgtt cagcccgacc gctgcgcctt atccggtaac tatcgtcttg agtccaaccc | 1380 |
| ggtaagacac gacttatcgc cactggcagc agccactggt aacaggatta gcagagcgag | 1440 |
| gtatgtaggc ggtgctacag agttcttgaa gtggtggcct aactacggct acactagaag | 1500 |

```
aacagtattt ggtatctgcg ctctgctgaa gccagttacc ttcggaaaaa gagttggtag    1560
ctcttgatcc ggcaaacaaa ccaccgctgg tagcggtggt tttttgttt acaagcagca    1620 gattacgcgc agaaaaaaag gatctcaaga agatcctttg atcttttcta cggggtctga    1680
cgctcagcta gcgctcagaa gaactcgtca agaaggcgat agaaggcgat gcgctgcgaa    1740
tcgggagcgg cgataccgta aagcacgagg aagcggtcag cccattcgcc gccaagctct    1800
tcagcaatat cacgggtagc caacgctatg tcctgatagc ggtccgccac acccagccgg    1860
ccacagtcga tgaatccaga aaagcggcca ttttccacca tgatattcgg caagcaggca    1920
tcgccatgag tcacgacgag atcctcgccg tcgggcatgc gcgccttgag cctggcgaac    1980
agttcggctg gcgcgagccc ctgatgctct tcgtccagat catcctgatc gacaagaccg    2040
gcttccatcc gagtacgtgc tcgctcgatg cgatgtttcg cttggtggtc gaatgggcag    2100
gtagccggat caagcgtatg cagccgccgc attgcatcag ccatgatgga tactttctcg    2160
gcaggagcaa ggtgagatga caggagatcc tgccccggca cttcgcccaa tagcagccag    2220
tcccttcccg cttcagtgac aacgtcgagc acagctgcgc aaggaacgcc cgtcgtggcc    2280
agccacgata gccgcgctgc ctcgtcctgc agttcattca gggcaccgga caggtcggtc    2340
ttgacaaaaa gaaccgggcg cccctgcgct gacagccgga acacggcggc atcagagcag    2400
ccgattgtct gttgtgccca gtcatagccg aatagcctct ccacccaagc ggccggagaa    2460
cctgcgtgca atccatcttg ttcaatcatg cgaaacgatc ctcatcctgt ctcttgatca    2520
gatcttgatc ccctgcgcca tcagatcctt ggcggcaaga aagccatcca gtttactttg    2580
cagggcttcc caaccttacc agagggcgcc ccagctggca attccggttc gcttgctgtc    2640
cataaaaccg cccagtctag caactgttgg gaagggcgat cgtgtaatac gactcactat    2700
agggcgaatt ggagct                                                   2716

<210> SEQ ID NO 28
<211> LENGTH: 2716
<212> TYPE: DNA
<213> ORGANISM: artificial sequence
<220> FEATURE:
<223> OTHER INFORMATION: This is the codon optimized bovine-GHRH
      expression plasmid.

<400> SEQUENCE: 28
ccaccgcggt ggcggccgtc cgccctcggc accatcctca cgacacccaa atatggcgac      60
gggtgaggaa tggtggggag ttatttttag agcggtgagg aagtgggca ggcagcaggt     120 gttggcgctc taaaaataac tcccgggagt tatttttaga gcggaggaat ggtggacacc     180
caaatatggc gacggttcct caccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct caccagctg ccatggtgct gtgggtgttc     420
ttcctggtga ccctgacccect gagcagcggc tcccacggct ccctgccctc ccagcctctg     480
cgcatccctc gctacgccga cgccatcttc accaacagct accgcaaggt gctcggccag     540
ctcagcgccc gcaagctcct gcaggacatc atgaaccggc agcagggcga gcgcaaccag     600
gagcagggag cctgataagc ttatcggggt ggcatccctg tgacccctcc ccagtgcctc     660 tcctggcccct ggaagttgcc actccagtgc ccaccagcct tgtcctaata aaattaagtt     720
gcatcatttt gtctgactag gtgtccttct ataatattat ggggtggagg gggtggtat      780
```

```
ggagcaaggg gcaagttggg aagacaacct gtagggctcg agggggggcc cggtaccagc    840
ttttgttccc tttagtgagg gttaatttcg agcttggtct ccgcttcct cgctcactga     900 ctcgctgcgc tcggtcgttc ggctgcggcg agcggtatca gctcactcaa aggcggtaat    960
acggttatcc acagaatcag gggataacgc aggaaagaac atgtgagcaa aggccagca   1020 aaaggccagg aaccgtaaaa aggccgcgtt gctggcgttt ttccataggc tccgccccc   1080 tgacgagcat cacaaaaatc gacgctcaag tcagaggtgg cgaaacccga caggactata   1140
aagataccag gcgtttcccc ctggaagctc cctcgtgcgc tctcctgttc cgaccctgcc   1200
gcttaccgga tacctgtccg cctttctccc ttcgggaagc gtggcgcttt ctcatagctc   1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag   1500
aacagtattt ggtatctgcg ctctgctgaa gccagttacc ttcggaaaaa gagttggtag   1560
ctcttgatcc ggcaaacaaa ccaccgctgg tagcggtggt ttttttgttt acaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa   1740
tcgggagcgg cgataccgta agcacgagg aagcggtcag cccattcgcc gccaagctct   1800
tcagcaatat cacgggtagc caacgctatg tcctgatagc ggtccgccac acccagccgg   1860
ccacagtcga tgaatccaga aaagcggcca ttttccacca tgatattcgg caagcaggca   1920
tcgccatgag tcacgacgag atcctcgccg tcgggcatgc gcgccttgag cctggcgaac   1980
agttcggctg gcgcgagccc ctgatgctct tcgtccagat catcctgatc gacaagaccg   2040
gcttccatcc gagtacgtgc tcgctcgatg cgatgtttcg cttggtggtc gaatgggcag   2100
gtagccggat caagcgtatg cagccgccgc attgcatcag ccatgatgga tactttctcg   2160
gcaggagcaa ggtgagatga caggagatcc tgccccggca cttcgcccaa tagcagccag   2220
tcccttcccg cttcagtgac aacgtcgagc acagctgcgc aaggaacgcc cgtcgtggcc   2280
agccacgata gccgcgctgc ctcgtcctgc agttcattca gggcaccgga caggtcggtc   2340
ttgacaaaaa gaaccgggcg cccctgcgct gacagccgga acacggcggc atcagagcag   2400
ccgattgtct gttgtgccca gtcatagccg aatagcctct ccacccaagc ggccggagaa   2460
cctgcgtgca atccatcttg ttcaatcatg cgaaacgatc ctcatcctgt ctcttgatca   2520
gatcttgatc ccctgcgcca tcagatcctt ggcggcaaga agccatcca gtttactttg   2580 cagggcttcc caaccttacc agagggcgcc ccagctggca attccggttc gcttgctgtc   2640
cataaaaccg cccagtctag caactgttgg aagggcgat cgtgtaatac gactcactat   2700
agggcgaatt ggagct                                                  2716
```

<210> SEQ ID NO 29
<211> LENGTH: 2716
<212> TYPE: DNA
<213> ORGANISM: artificial sequence
<220> FEATURE:
<223> OTHER INFORMATION: This is the codon optimized cat-GHRH expression plasmid.

<400> SEQUENCE: 29

```
ccaccgcggt ggcggccgtc cgccctcggc accatcctca cgacacccaa atatggcgac     60
```

-continued

```
gggtgaggaa tggtggggag ttatttttag agcggtgagg aaggtgggca ggcagcaggt       120
gttggcgctc taaaaataac tcccgggagt tattttaga gcggaggaat ggtggacacc        180
caaatatggc gacggttcct cacccgtcgc catatttggg tgtccgccct cggccggggc      240
cgcattcctg ggggccgggc ggtgctcccg cccgcctcga taaaaggctc cggggccggc       300
ggcggcccac gagctacccg gaggagcggg aggcgccaag cggatcccaa ggcccaactc       360
cccgaaccac tcagggtcct gtggacagct cacctagctg ccatggtgct ctgggtgttc      420
ttcctggtga tcctcaccce ssacagtggc tcccactgct ccccgccatc cctgcccctc       480
agaatgcctc ggtatgcaga tgccatcttc accaacagct accggaaggt gctgggtcag      540
ctgtctgccc gcaagctact gcaggacatc atgagcagac agcagggaga gagaaaccag      600
gagcaaggag cataataagc ttatcgggt ggcatccctg tgaccctcc ccagtgcctc        660 tcctggccct ggaagttgcc actccagtgc ccaccagcct tgtcctaata aaattaagtt     720
gcatcatttt gtctgactag gtgtccttct ataatattat ggggtggagg ggggtggtat    780
ggagcaaggg gcaagttggg aagacaacct gtagggctcg aggggggggcc cggtaccagc    840 ttttgttccc tttagtgagg gttaatttcg agcttggtct tccgcttcct cgctcactga     900
ctcgctgcgc tcggtcgttc ggctgcggcg agcggtatca gctcactcaa aggcggtaat    960
acggttatcc acagaatcag gggataacgc aggaaagaac atgtgagcaa aaggccagca    1020
aaaggccagg aaccgtaaaa aggccgcgtt gctggcgttt ttccataggc tccgccccc    1080 tgacgagcat cacaaaaatc gacgctcaag tcagaggtgg cgaaacccga caggactata    1140
aagataccag gcgtttcccc ctggaagctc cctcgtgcgc tctcctgttc cgaccctgcc    1200
gcttaccgga tacctgtccg cctttctccc ttcgggaagc gtggcgcttt ctcatagctc    1260
acgctgtagg tatctcagtt cggtgtaggt cgttcgctcc aagctgggct gtgtgcacga   1320
accccccgtt cagcccgacc gctgcgcctt atccggtaac tatcgtcttg agtccaaccc   1380
ggtaagacac gacttatcgc cactggcagc agccactggt aacaggatta gcagagcgag   1440
gtatgtaggc ggtgctacag agttcttgaa gtggtggcct aactacggct acactagaag    1500
aacagtattt ggtatctgcg ctctgctgaa gccagttacc ttcggaaaaa gagttggtag   1560
ctcttgatcc ggcaaacaaa ccaccgctgg tagcggtggt ttttttgttt acaagcagca   1620
gattacgcgc agaaaaaaag gatctcaaga agatcctttg atcttttcta cggggtctga   1680
cgctcagcta gcgctcagaa gaactcgtca agaaggcgat agaaggcgat gcgctgcgaa    1740
tcgggagcgg cgataccgta aagcacgagg aagcggtcag cccattcgcc gccaagctct    1800
tcagcaatat cacgggtagc caacgctatg tcctgatagc ggtccgccac acccagccgg    1860
ccacagtcga tgaatccaga aaagcggcca ttttccacca tgatattcgg caagcaggca    1920
tcgccatgag tcacgacgag atcctcgccg tcgggcatgc gcgccttgag cctggcgaac    1980
agttcggctg gcgcgagccc ctgatgctct tcgtccagat catcctgatc gacaagaccg    2040
gcttccatcc gagtacgtgc tcgctcgatg cgatgtttcg cttggtggtc gaatgggcag    2100
gtagccggat caagcgtatg cagccgccgc attgcatcag ccatgatgga tactttctcg    2160
gcaggagcaa ggtgagatga caggagatcc tgccccggca cttcgcccaa tagcagccag    2220
tcccttcccg cttcagtgac aacgtcgagc acagctgcgc aaggaacgcc cgtcgtggcc    2280
agccacgata gccgcgctgc ctcgtcctgc agttcattca gggcaccgga caggtcggtc    2340
ttgacaaaaa gaaccgggcg cccctgcgct gacagccgga acacggcggc atcagagcag    2400
ccgattgtct gttgtgccca gtcatagccg aatagcctct ccacccaagc ggccggagaa    2460
```

-continued

```
cctgcgtgca atccatcttg ttcaatcatg cgaaacgatc ctcatcctgt ctcttgatca    2520
gatcttgatc ccctgcgcca tcagatcctt ggcggcaaga aagccatcca gtttactttg    2580
cagggcttcc aaccttacc agagggcgcc ccagctggca attccggttc gcttgctgtc    2640
cataaaaccg cccagtctag caactgttgg gaagggcgat cgtgtaatac gactcactat    2700
agggcgaatt ggagct                                                    2716
```

<210> SEQ ID NO 30
<211> LENGTH: 2739
<212> TYPE: DNA
<213> ORGANISM: artificial sequence
<220> FEATURE:
<223> OTHER INFORMATION: This is the codon optimized TI-GHRH expression
      plasmid.

<400> SEQUENCE: 30

```
ccaccgcggt ggcggccgtc cgccctcggc accatcctca cgacacccaa atatggcgac     60
gggtgaggaa tggtggggag ttattttag agcggtgagg aaggtgggca ggcagcaggt    120
gttggcgctc taaaataac tcccgggagt tattttaga gcgaggaat ggtggacacc      180 caaatatggc gacggttcct cacccgtcgc catatttggg tgtccgccct cggccggggc    240
cgcattcctg ggggccgggc ggtgctcccg ccgcctcga taaaggctc cggggccggc     300 ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct ccccacctcc ccctttgacc    480
ctcaggatgc ggcggtatat cgatgccatc ttcaccaaca gctaccggaa ggtgctggcc    540
cagctgtccg cccgcaagct gctccaggac atcctgaaca ggcagcaggg agagaggaac    600
caagagcaag gagcataatg actgcaggaa ttcgatatca gcttatcgg ggtggcatcc     660 ctgtgacccc tccccagtgc ctctcctggc cctggaagtt gccactccag tgcccaccag    720
ccttgtccta ataaaattaa gttgcatcat tttgtctgac taggtgtcct tctataatat    780 tatgggtgg aggggggtgg tatggagcaa ggggcaagtt gggaagacaa cctgtagggc     840 tcgaggggg gcccggtacc agcttttgtt ccctttagtg agggttaatt tcgagcttgg    900
tcttccgctt cctcgctcac tgactcgctg cgctcggtcg ttcggctgcg gcgagcggta    960
tcagctcact caaaggcggt aatacggtta tccacagaat caggggataa cgcaggaaag   1020
aacatgtgag caaaaggcca gcaaaaggcc aggaaccgta aaaaggccgc gttgctggcg    1080
tttttccata ggctccgccc ccctgacgag catcacaaaa atcgacgctc aagtcagagg   1140
tggcgaaacc cgacaggact ataaagatac caggcgtttc ccctggaag ctccctcgtg    1200 cgctctcctg ttccgaccct gccgcttacc ggatacctgt ccgcctttct cccttcggga    1260
agcgtggcgc tttctcatag ctcacgctgt aggtatctca gttcggtgta ggtcgttcgc   1320
tccaagctgg gctgtgtgca cgaaccccc gttcagcccg accgctgcgc cttatccggt    1380
aactatcgtc ttgagtccaa cccggtaaga cacgacttat cgccactggc agcagccact   1440
ggtaacagga ttagcagagc gaggtatgta ggcggtgcta cagagttctt gaagtggtgg   1500
cctaactacg gctacactag aagaacagta tttggtatct gcgctctgct gaagccagtt   1560
accttcggaa aaagagttgg tagctcttga tccggcaaac aaaccaccgc tggtagcggt   1620
ggtttttttg tttacaagca gcagattacg cgcagaaaaa aaggatctca agaagatcct   1680
ttgatctttt ctacggggtc tgacgctcag ctagcgctca gaagaactcg tcaagaaggc   1740
```

```
gatagaaggc gatgcgctgc gaatcgggag cggcgatacc gtaaagcacg aggaagcggt    1800
cagcccattc gccgccaagc tcttcagcaa tatcacgggt agccaacgct atgtcctgat    1860
agcggtccgc cacacccagc cggccacagt cgatgaatcc agaaaagcgg ccattttcca    1920
ccatgatatt cggcaagcag gcatcgccat gagtcacgac gagatcctcg ccgtcgggca    1980
tgcgcgcctt gagcctggcg aacagttcgg ctggcgcgag ccctgatgc tcttcgtcca    2040 gatcatcctg atcgacaaga ccggcttcca tccgagtacg tgctcgctcg atgcgatgtt    2100
tcgcttggtg tcgaatggg caggtagccg atcaagcgt atgcagccgc cgcattgcat     2160
cagccatgat ggatactttc tcggcaggag caaggtgaga tgacaggaga tcctgccccg    2220
gcacttcgcc caatagcagc cagtcccttc ccgcttcagt gacaacgtcg agcacagctg    2280
cgcaaggaac gcccgtcgtg gccagccacg atagccgcgc tgcctcgtcc tgcagttcat    2340
tcagggcacc ggacaggtcg gtcttgacaa aaagaaccgg gcgcccctgc gctgacagcc    2400
ggaacacggc ggcatcagag cagccgattg tctgttgtgc ccagtcatag ccgaatagcc    2460
tctccaccca gcggccgga gaacctgcgt gcaatccatc ttgttcaatc atgcgaaacg     2520
atcctcatcc tgtctcttga tcagatcttg atcccctgcg ccatcagatc cttggcggca    2580
agaaagccat ccagtttact ttgcagggct cccaacctt accagagggc gcccagctg      2640 gcaattccgg ttcgcttgct gtccataaaa ccgcccagtc tagcaactgt tgggaagggc    2700
gatcgtgtaa tacgactcac tatagggcga attggagct                           2739
```

<210> SEQ ID NO 31
<211> LENGTH: 2716
<212> TYPE: DNA
<213> ORGANISM: artificial sequence
<220> FEATURE:
<223> OTHER INFORMATION: This is the codon optimized ovine-GHRH
      expression plasmid.

<400> SEQUENCE: 31

```
ccaccgcggt ggcggccgtc cgccctcggc accatcctca cgacacccaa atatggcgac     60
gggtgaggaa tggtggggag ttattttag agcggtgagg aaggtgggca ggcagcaggt    120
gttggcgctc taaaataac tcccgggagt tattttaga gcggaggaat ggtgacacc      180 caaatatggc gacggttcct caccgtcgc catatttggg tgtccgccct cggccggggc    240
cgcattcctg ggggcgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct gtgggtgttc    420
ttcctggtga ccctgaccct gagcagcgga agccacggca gcctgccag ccagcccctg    480 aggatcccta ggtacgccga cgccatcttc accaacagct acaggaagat cctgggccag    540
ctgagcgcta ggaagctcct gcaggacatc atgaacaggc agcagggcga gagaaccag    600 gagcagggcg cctgataagc ttatcggggt ggcatccctg tgacccctcc ccagtgcctc    660 tcctggcccct ggaagttgcc actccagtgc ccaccagcct tgtcctaata aaattaagtt    720 gcatcattt gtctgactag gtgtccttct ataatattat ggggtggagg gggtggtat     780 ggagcaaggg gcaagttggg aagacaacct gtagggctcg agggggggcc cggtaccagc    840
ttttgttccc tttagtgagg gttaatttcg agcttggtct tccgcttcct cgctcactga    900
ctcgctgcgc tcggtcgttc ggctgcggcg agcggtatca gctcactcaa aggcggtaat    960
acggttatcc acagaatcag gggataacgc aggaaagaac atgtgagcaa aaggccagca   1020
```

-continued

| | |
|---|---|
| aaaggccagg aaccgtaaaa aggccgcgtt gctggcgttt ttccataggc tccgccccc | 1080 |
| tgacgagcat cacaaaaatc gacgctcaag tcagaggtgg cgaaacccga caggactata | 1140 |
| aagataccag gcgttcccc ctggaagctc cctcgtgcgc tctcctgttc cgaccctgcc | 1200 |
| gcttaccgga tacctgtccg ccttctccc ttcgggaagc gtggcgcttt ctcatagctc | 1260 |
| acgctgtagg tatctcagtt cggtgtaggt cgttcgctcc aagctgggct gtgtgcacga | 1320 |
| accccccgtt cagcccgacc gctgcgcctt atccggtaac tatcgtcttg agtccaaccc | 1380 |
| ggtaagacac gacttatcgc cactggcagc agccactggt aacaggatta gcagagcgag | 1440 |
| gtatgtaggc ggtgctacag agttcttgaa gtggtggcct aactacggct acactagaag | 1500 |
| aacagtattt ggtatctgcg ctctgctgaa gccagttacc ttcggaaaaa gagttggtag | 1560 |
| ctcttgatcc ggcaaacaaa ccaccgctgg tagcggtggt ttttttgttt acaagcagca | 1620 |
| gattacgcgc agaaaaaaag gatctcaaga agatcctttg atcttttcta cggggtctga | 1680 |
| cgctcagcta gcgctcagaa gaactcgtca agaaggcgat agaaggcgat gcgctgcgaa | 1740 |
| tcgggagcgg cgataccgta agcacgagg aagcggtcag cccattcgcc gccaagctct | 1800 |
| tcagcaatat cacgggtagc caacgctatg tcctgatagc ggtccgccac acccagccgg | 1860 |
| ccacagtcga tgaatccaga aaagcggcca ttttccacca tgatattcgg caagcaggca | 1920 |
| tcgccatgag tcacgacgag atcctcgccg tcgggcatgc gcgccttgag cctggcgaac | 1980 |
| agttcggctg gcgcgagccc ctgatgctct tcgtccagat catcctgatc gacaagaccg | 2040 |
| gcttccatcc gagtacgtgc tcgctcgatg cgatgtttcg cttggtggtc gaatgggcag | 2100 |
| gtagccggat caagcgtatg cagccgccgc attgcatcag ccatgatgga ctttctcg | 2160 |
| gcaggagcaa ggtgagatga caggagatcc tgccccggca cttcgcccaa tagcagccag | 2220 |
| tcccttcccg cttcagtgac aacgtcgagc acagctgcgc aaggaacgcc cgtcgtggcc | 2280 |
| agccacgata gccgcgctgc ctcgtcctgc agttcattca gggcaccgga caggtcggtc | 2340 |
| ttgacaaaaa gaaccgggcg cccctgcgct gacagccgga acacggcggc atcagagcag | 2400 |
| ccgattgtct gttgtgccca gtcatagccg aatagcctct ccacccaagc ggccggagaa | 2460 |
| cctgcgtgca atccatcttg ttcaatcatg cgaaacgatc ctcatcctgt ctcttgatca | 2520 |
| gatcttgatc ccctgcgcca tcagatcctt ggcggcaaga aagccatcca gtttactttg | 2580 |
| cagggcttcc caaccttacc agagggcgcc ccagctggca attccggttc gcttgctgtc | 2640 |
| cataaaaccg cccagtctag caactgttgg aagggcgat cgtgtaatac gactcactat | 2700 |
| agggcgaatt ggagct | 2716 |

<210> SEQ ID NO 32
<211> LENGTH: 2725
<212> TYPE: DNA
<213> ORGANISM: artificial sequence
<220> FEATURE:
<223> OTHER INFORMATION: This is the codon optimized chicken-GHRH
      expression plasmid.

<400> SEQUENCE: 32

| | |
|---|---|
| ccaccgcggt ggcggccgtc cgccctcggc accatcctca cgacacccaa atatggcgac | 60 |
| gggtgaggaa tggtgggag ttattttag agcggtgagg aaggtgggca ggcagcaggt | 120 |
| gttggcgctc taaaaataac tcccgggagt tatttttaga gcggaggaat ggtggacacc | 180 |
| caaatatggc gacggttcct cacccgtcgc catatttggg tgtccgccct cggccggggc | 240 |
| cgcattcctg ggggccgggc ggtgctcccg cccgcctcga taaaaggctc cggggccggc | 300 |

```
ggcggcccac gagctacccg gaggagcggg aggcgccaag cggatcccaa ggcccaactc    360
cccgaaccac tcagggtcct gtggacagct cacctagctg ccatggccct gtgggtgttc    420
tttgtgctgc tgaccctgac ctccggaagc cactgcagcc tgccacccag cccacccttc    480
cgcgtcaggc gccacgccga cggcatcttc agcaaggcct accgcaagct cctgggccag    540
ctgagcgcac gcaactacct gcacagcctg atggccaagc gcgtgggcag cggactggga    600
gacgaggccg agcccctgag ctgataagct tatcggggtg catccctgt gacccctccc     660 cagtgcctct cctggccctg gaagttgcca ctccagtgcc caccagcctt gtcctaataa    720
aattaagttg catcattttg tctgactagg tgtccttcta taatattatg gggtggaggg    780
gggtggtatg gagcaagggg caagttggga agacaacctg tagggctcga gggggggccc    840
ggtaccagct tttgttccct ttagtgaggg ttaatttcga gcttggtctt ccgcttcctc    900
gctcactgac tcgctgcgct cggtcgttcg gctgcggcga gcggtatcag ctcactcaaa    960
ggcggtaata cggttatcca cagaatcagg ggataacgca ggaaagaaca tgtgagcaaa   1020
aggccagcaa aaggccagga accgtaaaaa ggccgcgttg ctggcgtttt tccataggct   1080
ccgcccccct gacgagcatc acaaaaatcg acgctcaagt cagaggtggc gaaacccgac   1140
aggactataa agataccagg cgtttccccc tggaagctcc ctcgtgcgct ctcctgttcc   1200
gaccctgccg cttaccggat acctgtccgc ctttctccct tcgggaagcg tggcgctttc   1260
tcatagctca cgctgtaggt atctcagttc ggtgtaggtc gttcgctcca agctgggctg   1320
tgtgcacgaa ccccccgttc agcccgaccg ctgcgcctta ccggtaact atcgtcttga    1380 gtccaacccg gtaagacacg acttatcgcc actggcagca gccactggta acaggattag   1440
cagagcgagg tatgtaggcg gtgctacaga gttcttgaag tggtggccta actacggcta   1500
cactagaaga acagtatttg gtatctgcgc tctgctgaag ccagttacct tcggaaaaag   1560
agttggtagc tcttgatccg gcaaacaaac caccgctggt agcggtggtt ttttgttta    1620 caagcagcag attacgcgca gaaaaaaagg atcctttga tcttttctac               1680 ggggtctgac gctcagctag cgctcagaag aactcgtcaa gaaggcgata gaaggcgatg   1740
cgctgcgaat cgggagcggc gataccgtaa agcacgagga agcggtcagc ccattcgccg   1800
ccaagctctt cagcaatatc acgggtagcc aacgctatgt cctgatagcg gtccgccaca   1860
cccagccggc cacagtcgat gaatccagaa agcggccat tttccaccat gatattcggc    1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag gcaccggac    2340 aggtcggtct tgacaaaaag aaccgggcgc ccctgcgctg acagccggaa cacggcggca   2400
tcagagcagc cgattgtctg ttgtgcccag tcatagccga atagcctctc cacccaagcg   2460
gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
```

```
cttgctgtcc ataaaaccgc ccagtctagc aactgttggg aagggcgatc gtgtaatacg    2700
actcactata gggcgaattg gagct                                          2725

<210> SEQ ID NO 33
<211> LENGTH: 5
<212> TYPE: DNA
<213> ORGANISM: artificial sequence
<220> FEATURE:
<223> OTHER INFORMATION: This is the codon optimized Horse-GHRH
      expression plasmid.

<400> SEQUENCE: 33 aaaaa                                                                5

<210> SEQ ID NO 34
<211> LENGTH: 225
<212> TYPE: DNA
<213> ORGANISM: artificial sequence
<220> FEATURE:
<223> OTHER INFORMATION: Sequence for an analog bovine GHRH sequence.

<400> SEQUENCE: 34
gccatggtgc tgtgggtgtt cttcctggtg accctgaccc tgagcagcgg ctcccacggc    60
tccctgccct cccagcctct gcgcatccct cgctacgccg acgccatctt caccaacagc   120
taccgcaagg tgctcggcca gctcagcgcc cgcaagctcc tgcaggacat catgaaccgg   180
cagcagggcg agcgcaacca ggagcaggga gcctgataag cttgc                   225

<210> SEQ ID NO 35
<211> LENGTH: 225
<212> TYPE: DNA
<213> ORGANISM: artificial sequence
<220> FEATURE:
<223> OTHER INFORMATION: Sequence for an analog ovine GHRH sequence.

<400> SEQUENCE: 35
gccatggtgc tgtgggtgtt cttcctggtg accctgaccc tgagcagcgg aagccacggc    60
agcctgccca gccagcccct gaggatccct aggtacgccg acgccatctt caccaacagc   120
tacaggaaga tcctgggcca gctgagcgct aggaagctcc tgcaggacat catgaacagg   180
cagcagggcg agaggaacca ggagcagggc gcctgataag cttgc                   225

<210> SEQ ID NO 36
<211> LENGTH: 246
<212> TYPE: DNA
<213> ORGANISM: artificial sequence
<220> FEATURE:
<223> OTHER INFORMATION: Sequence for an analog chicken GHRH sequence.

<400> SEQUENCE: 36
gccatggtgc tctgggtgct ctttgtgatc ctcatcctca ccagcggcag ccactgcagc    60
ctgcctccca gccctcccct caggatgcag aggcacgtgg acgccatctt caccaccaac   120
tacaggaagc tgctgagcca gctgtacgcc aggaaggtga tccaggacat catgaacaag   180
cagggcgaga ggatccagga gcagagggcc aggctgagct gataagcttg cgatgagttc   240
ttctaa                                                              246

<210> SEQ ID NO 37
<211> LENGTH: 190
<212> TYPE: DNA
<213> ORGANISM: artificial sequence
<220> FEATURE:
```

```
<223> OTHER INFORMATION: Nucleic acid sequence of  human growth hormone
      poly A tail.

<400> SEQUENCE: 37
gggtggcatc cctgtgaccc ctccccagtg cctctcctgg ccctggaagt tgccactcca      60
gtgcccacca gccttgtcct aataaaatta agttgcatca ttttgtctga ctaggtgtcc     120
ttctataata ttatggggtg gaggggggtg gtatggagca agggggcaagt tgggaagaca    180 acctgtaggg                                                           190

<210> SEQ ID NO 38
<211> LENGTH: 55
<212> TYPE: DNA
<213> ORGANISM: artificial sequence
<220> FEATURE:
<223> OTHER INFORMATION: Nucleic acid sequence of human growth hormone
      5' UTR

<400> SEQUENCE: 38
caaggcccaa ctccccgaac cactcagggt cctgtggaca gctcacctag ctgcc          55

<210> SEQ ID NO 39
<211> LENGTH: 782
<212> TYPE: DNA
<213> ORGANISM: artificial sequence
<220> FEATURE:
<223> OTHER INFORMATION: Nucleic acid sequence of a plasmid pUC-18
      origin of replicaiton

<400> SEQUENCE: 39
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180 ttttccata  ggctccgccc ccctgacgag catcacaaaa atcgacgctc aagtcagagg    240
tggcgaaacc cgacaggact ataaagatac caggcgtttc ccctggaag ctccctcgtg     300 cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccc gttcagcccg accgctgcgc cttatccggt     480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720 ggttttttg  tttgcaagca gcagattacg cgcagaaaaa aaggatctca agaagatcct    780
tt                                                                  782

<210> SEQ ID NO 40
<211> LENGTH: 5
<212> TYPE: DNA
<213> ORGANISM: artificial sequence
<220> FEATURE:
<223> OTHER INFORMATION: This is a NEO ribosomal binding site

<400> SEQUENCE: 40 tcctc                                                                5

<210> SEQ ID NO 41
```

```
<211> LENGTH: 31
<212> TYPE: PRT
<213> ORGANISM: Artificial sequence
<220> FEATURE:
<223> OTHER INFORMATION: This is a signal peptide for HV-GHRH.

<400> SEQUENCE: 41

Met Val Leu Trp Val Phe Phe Phe Val Ile Leu Thr Leu Ser Asn Ser
1               5                   10                  15

Ser His Cys Ser Pro Pro Pro Pro Leu Thr Leu Arg Met Arg Arg
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: This is a signal peptide for Pig GHRH.

<400> SEQUENCE: 42

Met Val Leu Trp Val Phe Phe Phe Val Ile Leu Thr Leu Ser Asn Ser
1               5                   10                  15

Ser His Cys Ser Pro Pro Pro Pro Leu Thr Leu Arg Met Arg Arg
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: This is the signal peptide for Bovine GHRH.
<220> FEATURE:
<221> NAME/KEY: MISC_FEATURE
<222> LOCATION: (24)..(24)
<223> OTHER INFORMATION: Xaa can be any other AA
<220> FEATURE:
<221> NAME/KEY: MISC_FEATURE
<222> LOCATION: (24)..(24)
<223> OTHER INFORMATION: Xaa can be proline ("P") or serine ("S")

<400> SEQUENCE: 43

Met Val Leu Trp Val Phe Phe Leu Val Thr Leu Thr Leu Ser Ser Gly
1               5                   10                  15

Ser His Gly Ser Leu Pro Ser Xaa Gln Pro Leu Arg Ile Pro Arg
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: This is a signal peptide for Dog GHRH
<220> FEATURE:
<221> NAME/KEY: MISC_FEATURE
<222> LOCATION: (24)..(24)
<223> OTHER INFORMATION: Xaa can be any AA
<220> FEATURE:
<221> NAME/KEY: MISC_FEATURE
<222> LOCATION: (24)..(24)
<223> OTHER INFORMATION: Xaa can be proline ("P") or serine ("S")

<400> SEQUENCE: 44

Met Val Leu Trp Val Phe Phe Leu Val Ile Leu Thr Leu Ser Ser Gly
1               5                   10                  15

Ser His Ser Ser Pro Pro Ser Xaa Leu Pro Ile Arg Ile Pro Arg
            20                  25                  30
```

```
<210> SEQ ID NO 45
<211> LENGTH: 31
<212> TYPE: PRT
<213> ORGANISM: Artificial Sequence
<220> FEATURE:
<223> OTHER INFORMATION: This is the signal peptide for cat GHRH.
<220> FEATURE:
<221> NAME/KEY: MISC_FEATURE
<222> LOCATION: (24)..(24)
<223> OTHER INFORMATION: Xaa can be any other AA
<220> FEATURE:
<221> NAME/KEY: MISC_FEATURE
<222> LOCATION: (24)..(24)
<223> OTHER INFORMATION: Xaa can be proline ("P") or serine ("S")

<400> SEQUENCE: 45

Met Val Leu Trp Val Phe Phe Leu Val Ile Leu Thr Leu Asp Ser Gly
1               5                   10                  15

Ser His Cys Ser Pro Pro Ser Xaa Leu Pro Leu Arg Met Pro Arg
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: This is the signal peptide for Ovine GHRH.
<220> FEATURE:
<221> NAME/KEY: MISC_FEATURE
<222> LOCATION: (24)..(24)
<223> OTHER INFORMATION: Xaa can be any other AA
<220> FEATURE:
<221> NAME/KEY: MISC_FEATURE
<222> LOCATION: (24)..(24)
<223> OTHER INFORMATION: Xaa can be proline ("P") or serine ("S")

<400> SEQUENCE: 46

Met Val Leu Trp Val Phe Phe Leu Val Thr Leu Thr Leu Ser Ser Gly
1               5                   10                  15

Ser His Gly Ser Leu Pro Ser Xaa Gln Pro Leu Arg Ile Pro Arg
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: This is the signal peptide for Chicken GHRH.

<400> SEQUENCE: 47

Met Ala Leu Trp Val Phe Phe Val Leu Leu Thr Leu Thr Ser Gly Ser
1               5                   10                  15

His Cys Ser Leu Pro Pro Ser Pro Pro Phe Arg Val Arg Arg
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: This is the signal peptide for Horse GHRH.

<400> SEQUENCE: 48

Met Val Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg
            20                  25                  30
```

```
<210> SEQ ID NO 49
<211> LENGTH: 31
<212> TYPE: PRT
<213> ORGANISM: Artificial Sequence
<220> FEATURE:
<223> OTHER INFORMATION: This is the signal peptide for Human GHRH.

<400> SEQUENCE: 49

Met Pro Leu Trp Val Phe Phe Phe Val Ile Leu Thr Leu Ser Asn Ser
1               5                   10                  15

Ser His Cys Ser Pro Pro Pro Leu Thr Leu Arg Met Arg Arg
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: This is the synthetic signal peptide RPRP GHRH.

<400> SEQUENCE: 50

Met Pro Leu Trp Val Phe Phe Phe Val Ile Leu Thr Leu Ser Asn Ser
1               5                   10                  15

Ser His Cys Ser Arg Pro Arg Pro Leu Thr Leu Arg Met Arg Arg
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: This is the synthetic signal peptide RPPP GHRH

<400> SEQUENCE: 51

Met Pro Leu Trp Val Phe Phe Phe Val Ile Leu Thr Leu Ser Asn Ser
1               5                   10                  15

Ser His Cys Ser Arg Pro Pro Pro Leu Thr Leu Arg Met Arg Arg
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: This is a signal peptide consesnsus sequence.
<220> FEATURE:
<221> NAME/KEY: MISC_FEATURE
<222> LOCATION: (8)..(8)
<223> OTHER INFORMATION: Xaa can be leucine ("L"), or phenylalanine
      ("F")
<220> FEATURE:
<221> NAME/KEY: MISC_FEATURE
<222> LOCATION: (15)..(15)
<223> OTHER INFORMATION: Xaa can be serine ("S"), or asparagine ("N")
<220> FEATURE:
<221> NAME/KEY: MISC_FEATURE
<222> LOCATION: (16)..(16)
<223> OTHER INFORMATION: Xaa can be glycine ("G") or serine ("S")
<220> FEATURE:
<221> NAME/KEY: MISC_FEATURE
<222> LOCATION: (21)..(21)
<223> OTHER INFORMATION: Xaa can be arginine ("R"), or Proline ("P").
<220> FEATURE:
<221> NAME/KEY: MISC_FEATURE
<222> LOCATION: (23)..(23)
<223> OTHER INFORMATION: Xaa can be proline ("P") or serine ("S")
<220> FEATURE:
<221> NAME/KEY: MISC_FEATURE
<222> LOCATION: (24)..(24)
```

-continued

```
<223> OTHER INFORMATION: Xaa can be proline ("P") or serine ("S")
<220> FEATURE:
<221> NAME/KEY: MISC_FEATURE
<222> LOCATION: (30)..(30)
<223> OTHER INFORMATION: Xaa can be arginine ("R"), or Proline ("P").

<400> SEQUENCE: 52

Met Val Leu Trp Val Phe Phe Xaa Val Ile Leu Thr Leu Ser Xaa Xaa
1               5                   10                  15

Ser His Cys Ser Xaa Pro Xaa Xaa Leu Pro Leu Arg Met Xaa Arg
            20              25                  30

<210> SEQ ID NO 53
<211> LENGTH: 20
<212> TYPE: DNA
<213> ORGANISM: Artificial sequence
<220> FEATURE:
<223> OTHER INFORMATION: Bam/Hind III 5' Primer sequence.

<400> SEQUENCE: 53
atggtgctct gggtgttctt                                              20

<210> SEQ ID NO 54
<211> LENGTH: 20
<212> TYPE: DNA
<213> ORGANISM: artificial Sequence
<220> FEATURE:
<223> OTHER INFORMATION: Exon 5 3' Primer Sequence

<400> SEQUENCE: 54
gtccttgagg gttcctactt                                              20

<210> SEQ ID NO 55
<211> LENGTH: 22
<212> TYPE: DNA
<213> ORGANISM: artificial Sequence
<220> FEATURE:
<223> OTHER INFORMATION: RPRP Upper strand primer 5'-3'

<400> SEQUENCE: 55
gctccagacc taggcctttg ac                                           22

<210> SEQ ID NO 56
<211> LENGTH: 22
<212> TYPE: DNA
<213> ORGANISM: artificial Sequence
<220> FEATURE:
<223> OTHER INFORMATION: RPRP Lower primer 5' - 3'

<400> SEQUENCE: 56
gtcaaaggcc taggtctgga gc                                           22

<210> SEQ ID NO 57
<211> LENGTH: 23
<212> TYPE: DNA
<213> ORGANISM: artificial Sequence
<220> FEATURE:
<223> OTHER INFORMATION: RPPP Upper primer 5' - 3'

<400> SEQUENCE: 57
tgctccagac ctcccccttt gac                                          23

<210> SEQ ID NO 58
<211> LENGTH: 22
<212> TYPE: DNA
<213> ORGANISM: artificial Sequence
```

<220> FEATURE:
<223> OTHER INFORMATION: RPPP Lower primer 5' - 3'

<400> SEQUENCE: 58
gtcaaagggg gaggtctgga gc                                            22

<210> SEQ ID NO 59
<211> LENGTH: 21
<212> TYPE: DNA
<213> ORGANISM: artificial Sequence
<220> FEATURE:
<223> OTHER INFORMATION: Nco I Primer 5'-3' sense

<400> SEQUENCE: 59
cctagctgcc atggtgctct g                                             21

<210> SEQ ID NO 60
<211> LENGTH: 24
<212> TYPE: DNA
<213> ORGANISM: artificial Sequence
<220> FEATURE:
<223> OTHER INFORMATION: Hind III Primer 5'-3'antisense

<400> SEQUENCE: 60
cccgataagc tttcattatg ctcc                                          24

<210> SEQ ID NO 61
<211> LENGTH: 2505
<212> TYPE: DNA
<213> ORGANISM: artificial sequence
<220> FEATURE:
<223> OTHER INFORMATION: Codon-optimized porcine wild-type GHRH plasmid,
      pAV0242.

<400> SEQUENCE: 61
ccaccgcggt ggcggccgtc cgccctcggc accatcctca cgacacccaa atatggcgac      60
gggtgaggaa tggtggggag ttattttttag agcggtgagg aaggtgggca ggcagcaggt    120
gttggcgctc taaaaataac tcccgggagt tattttttaga gcggaggaat ggtgacacc    180 caaatatggc gacggttcct caccgtcgc catatttggg tgtccgccct cggccggggc     240
cgcattcctg ggggccgggc ggtgctcccg cccgcctcga taaaaggctc ggggccggc     300 ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcacccT cagcaacagc tcccactgct ccccacctcc ccctttgacc    480
ctcaggatgc ggcggtatgc agatgccatc ttcaccaaca gctaccggaa ggtgctgggc    540
cagctgtccg cccgcaagct gctccaggac atcatgagca ggcagcaggg agagaggaac    600
caagagcaag gagcataatg aaagcttatc ggggtggcat ccctgtgacc cctccccagt    660
gcctctcctg gccctggaag ttgccactcc agtgcccacc agccttgtcc taataaaatt    720
aagttgcatc attttgtctg actaggtgtc cttctataat attatggggt ggaggggggt    780
ggtatggagc aaggggcaag ttgggaagac aacctgtagg gctcgagggg gggcccggta    840
ccatgtgagc aaaaggccag caaaaggcca ggaaccgtaa aaaggccgcg ttgctggcgt    900
ttttccatag gctccgcccc cctgacgagc atcacaaaaa tcgacgctca agtcagaggt    960
ggcgaaaccc gacaggacta taaagatacc aggcgtttcc ccctggaagc tccctcgtgc   1020
gctctcctgt tccgaccctg ccgcttaccg gatacctgtc cgcctttctc ccttcggaa   1080 gcgtggcgct ttctcatagc tcacgctgta ggtatctcag ttcggtgtag gtcgttcgct   1140

```
ccaagctggg ctgtgtgcac gaaccccccg ttcagcccga ccgctgcgcc ttatccggta    1200
actatcgtct tgagtccaac ccggtaagac acgacttatc gccactggca gcagccactg    1260
gtaacaggat tagcagagcg aggtatgtag gcggtgctac agagttcttg aagtggtggc    1320
ctaactacgg ctacactaga agaacagtat ttggtatctg cgctctgctg aagccagtta    1380
ccttcggaaa aagagttggt agctcttgat ccggcaaaca accaccgct ggtagcggtg      1440 gtttttttgt ttacaagcag cagattacgc gcagaaaaaa aggatctcaa gaagatcctt    1500
tgatcttttc tacggggtct gacgctcagc tagcgctcag aagaactcgt caagaaggcg    1560
atagaaggcg atgcgctgcg aatcgggagc ggcgataccg taaagcacga ggaagcggtc    1620
agcccattcg ccgccaagct cttcagcaat atcacgggta gccaacgcta tgtcctgata    1680
gcggtccgcc acacccagcc ggccacagtc gatgaatcca gaaaagcggc cattttccac    1740
catgatattc ggcaagcagg catcgccatg agtcacgacg agatcctcgc cgtcgggcat    1800
gcgcgccttg agcctggcga acagttcggc tggcgcgagc cctgatgct cttcgtccag      1860 atcatcctga tcgacaagac cggcttccat ccgagtacgt gctcgctcga tgcgatgttt    1920
cgcttggtgg tcgaatgggc aggtagccgg atcaagcgta tgcagccgcc gcattgcatc    1980
agccatgatg gatactttct cggcaggagc aaggtgagat gacaggagat cctgccccgg    2040
cacttcgccc aatagcagcc agtcccttcc cgcttcagtg acaacgtcga gcacagctgc    2100
gcaaggaacg cccgtcgtgg ccagccacga tagccgcgct gcctcgtcct gcagttcatt    2160
cagggcaccg gacaggtcgg tcttgacaaa aagaaccggg cgcccctgcg ctgacagccg    2220
gaacacggcg gcatcagagc agccgattgt ctgttgtgcc cagtcatagc cgaatagcct    2280
ctccacccaa gcggccggag aacctgcgtg caatccatct tgttcaatca tgcgaaacga    2340
tcctcatcct gtctcttgat cagatcttga tccctgcgc catcagatcc ttggcggcaa      2400
gaaagccatc cagtttactt tgcagggctt cccaacctta ccagagggcg ccccagctgg    2460
caattccggt tcgcttgctg tccataaaac cgcccagtct gagct                    2505
```

<210> SEQ ID NO 62
<211> LENGTH: 2505
<212> TYPE: DNA
<213> ORGANISM: artificial sequence
<220> FEATURE:
<223> OTHER INFORMATION: Codon-optimized Human GHRH plasmid, pAV0243.

<400> SEQUENCE: 62

```
ccaccgcggt ggcggccgtc cgccctcggc accatcctca cgacacccaa atatggcgac      60
gggtgaggaa tggtggggag ttattttttag agcggtgagg aagtgggca ggcagcaggt      120 gttggcgctc taaaaataac tcccgggagt tattttttaga gcggaggaat ggtggacacc    180
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct ccccacctcc ccctttgacc    480
ctcaggatgc ggcggtatgc agatgccatc ttcaccaaca gctaccggaa ggtgctgggc    540
cagctgtccg cccgcaagct gctgcaggac atcatgagca ggcagcaggg agagagcaac    600
caagagcgag gagcataatg aaagcttatc ggggtggcat ccctgtgacc cctccccagt    660
```

| | |
|---|---|
| gcctctcctg gccctggaag ttgccactcc agtgcccacc agccttgtcc taataaaatt | 720 |
| aagttgcatc attttgtctg actaggtgtc cttctataat attatgggt ggagggggt | 780 |
| ggtatggagc aagggcaag ttgggaagac aacctgtagg gctcgagggg gggcccggta | 840 |
| ccatgtgagc aaaaggccag caaaaggcca ggaaccgtaa aaaggccgcg ttgctggcgt | 900 |
| ttttccatag gctccgcccc cctgacgagc atcacaaaaa tcgacgctca agtcagaggt | 960 |
| ggcgaaaccc gacaggacta taaagatacc aggcgtttcc ccctggaagc tccctcgtgc | 1020 |
| gctctcctgt tccgaccctg ccgcttaccg gatacctgtc cgcctttctc ccttcgggaa | 1080 |
| gcgtggcgct ttctcatagc tcacgctgta ggtatctcag ttcggtgtag gtcgttcgct | 1140 |
| ccaagctggg ctgtgtgcac gaaccccccg ttcagcccga ccgctgcgcc ttatccggta | 1200 |
| actatcgtct tgagtccaac ccggtaagac acgacttatc gccactggca gcagccactg | 1260 |
| gtaacaggat tagcagagcg aggtatgtag gcggtgctac agagttcttg aagtggtggc | 1320 |
| ctaactacgg ctacactaga agaacagtat ttggtatctg cgctctgctg aagccagtta | 1380 |
| ccttcggaaa aagagttggt agctcttgat ccggcaaaca aaccaccgct ggtagcggtg | 1440 |
| gtttttttgt ttacaagcag cagattacgc gcagaaaaaa aggatctcaa gaagatcctt | 1500 |
| tgatcttttc tacggggtct gacgctcagc tagcgctcag aagaactcgt caagaaggcg | 1560 |
| atagaaggcg atgcgctgcg aatcgggagc ggcgataccg taaagcacga ggaagcggtc | 1620 |
| agcccattcg ccgccaagct cttcagcaat atcacgggta gccaacgcta tgtcctgata | 1680 |
| gcggtccgcc acacccagcc ggccacagtc gatgaatcca gaaaagcggc catttttccac | 1740 |
| catgatattc ggcaagcagg catcgccatg agtcacgacg agatcctcgc cgtcgggcat | 1800 |
| gcgcgccttg agcctggcga acagttcggc tggcgcgagc ccctgatgct cttcgtccag | 1860 |
| atcatcctga tcgacaagac cggcttccat ccgagtacgt gctcgctcga tgcgatgttt | 1920 |
| cgcttggtgg tcgaatgggc aggtagccgg atcaagcgta tgcagccgcc gcattgcatc | 1980 |
| agccatgatg gatactttct cggcaggagc aaggtgagat gacaggagat cctgccccgg | 2040 |
| cacttcgccc aatagcagcc agtcccttcc cgcttcagtg acaacgtcga gcacagctgc | 2100 |
| gcaaggaacg cccgtcgtgg ccagccacga tagccgcgct gcctcgtcct gcagttcatt | 2160 |
| cagggcaccg gacaggtcgg tcttgacaaa aagaaccggg cgcccctgcg ctgacagccg | 2220 |
| gaacacggcg gcatcagagc agccgattgt ctgttgtgcc cagtcatagc cgaatagcct | 2280 |
| ctccacccaa gcggccggag aacctgcgtg caatccatct tgttcaatca tgcgaaacga | 2340 |
| tcctcatcct gtctcttgat cagatcttga tcccctgcgc catcagatcc ttggcggcaa | 2400 |
| gaaagccatc cagtttactt tgcagggctt cccaacctta ccagagggcg ccccagctgg | 2460 |
| caattccggt tcgcttgctg tccataaaac cgcccagtct gagct | 2505 |

<210> SEQ ID NO 63
<211> LENGTH: 2505
<212> TYPE: DNA
<213> ORGANISM: artificial sequence
<220> FEATURE:
<223> OTHER INFORMATION: This is the codon-optimized RPRP-GHRH plasmid, pAV0244.

<400> SEQUENCE: 63

| | |
|---|---|
| ccaccgcggt ggcggccgtc cgccctcggc accatcctca cgacacccaa atatggcgac | 60 |
| gggtgaggaa tggtgggag ttattttag agcggtgagg aagtgggca ggcagcaggt | 120 |
| gttggcgctc taaaaataac tcccgggagt tattttaga gcggaggaat ggtggacacc | 180 |

```
caaatatggc gacggttcct cacccgtcgc catatttggg tgtccgccct cggccggggc    240
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct ccagacctag gcctttgacc    480
ctcaggatgc ggcggtatgc agatgccatc ttcaccaaca gctaccggaa ggtgctgggc    540
cagctgtccg cccgcaagct gctgcaggac atcatgagca ggcagcaggg agagagcaac    600
caagagcgag gagcataatg aaagcttatc ggggtggcat ccctgtgacc cctccccagt    660
gcctctcctg gccctggaag ttgccactcc agtgcccacc agccttgtcc taataaaatt    720
aagttgcatc attttgtctg actaggtgtc cttctataat attatgggt ggaggggggt     780 ggtatggagc aaggggcaag ttgggaagac aacctgtagg gctcgagggg gggcccggta    840
ccatgtgagc aaaaggccag caaaaggcca ggaaccgtaa aaaggccgcg ttgctggcgt    900
ttttccatag gctccgcccc cctgacgagc atcacaaaaa tcgacgctca agtcagaggt    960
ggcgaaaccc gacaggacta taaagatacc aggcgtttcc ccctggaagc tccctcgtgc   1020
gctctcctgt tccgaccctg ccgcttaccg gatacctgtc cgcctttctc ccttcgggaa   1080
gcgtggcgct ttctcatagc tcacgctgta ggtatctcag ttcggtgtag tcgttcgct    1140 ccaagctggg ctgtgtgcac gaaccccccg ttcagcccga ccgctgcgcc ttatccggta   1200
actatcgtct tgagtccaac ccggtaagac acgacttatc gccactggca gcagccactg   1260
gtaacaggat tagcagagcg aggtatgtag gcggtgctac agagttcttg aagtggtggc   1320
ctaactacgg ctacactaga agaacagtat ttggtatctg cgctctgctg aagccagtta   1380
ccttcggaaa aagagttggt agctcttgat ccggcaaaca accaccgct ggtagcggtg     1440 gtttttttgt ttacaagcag cagattacgc gcagaaaaaa aggatctcaa gaagatcctt   1500
tgatcttttc tacgggtct gacgctcagc tagcgctcag aagaactcgt caagaaggcg     1560
atagaaggcg atgcgctgcg aatcgggagc ggcgatccg taaagcacga ggaagcggtc     1620
agcccattcg ccgccaagct cttcagcaat atcacgggta gccaacgcta tgtcctgata   1680
gcggtccgcc acacccagcc ggccacagtc gatgaatcca gaaaagcggc catttccac     1740 catgatattc ggcaagcagg catcgccatg agtcacgacg agatcctcgc cgtcgggcat   1800
gcgcgccttg agcctggcga acagttcggc tggcgcgagc ccctgatgct cttcgtccag   1860
atcatcctga tcgacaagac cggcttccat ccgagtacgt gctcgctcga tgcgatgttt   1920
cgcttggtgg tcgaatgggc aggtagccgg atcaagcgta tgcagccgcc gcattgcatc   1980
agccatgatg gatactttct cggcaggagc aaggtgagat gacaggagat cctgccccgg   2040
cacttcgccc aatagcagcc agtcccttcc cgcttcagtg acaacgtcga gcacagctgc   2100
gcaaggaacg cccgtcgtgg ccagccacga tagccgcgct gcctcgtcct gcagttcatt   2160
cagggcaccg gacaggtcgg tcttgacaaa aagaaccggg cgcccctgcg ctgacagccg   2220
gaacacggcg gcatcagagc agccgattgt ctgttgtgcc cagtcatagc cgaatagcct   2280
ctccacccaa gcggccggag aacctgcgtg caatccatct tgttcaatca tgcgaaacga   2340
tcctcatcct gtctcttgat cagatcttga tcccctgcgc catcagatcc ttggcggcaa   2400
gaaagccatc cagtttactt tgcagggctt cccaacctta ccagagggcg ccccagctgg   2460
caattccggt tcgcttgctg tccataaaac cgcccagtct gagct                   2505
```

<210> SEQ ID NO 64
<211> LENGTH: 2505
<212> TYPE: DNA
<213> ORGANISM: artificial sequence
<220> FEATURE:
<223> OTHER INFORMATION: This is the codon-optimized RPPP-GHRH plasmid, pAV0245.

<400> SEQUENCE: 64

```
ccaccgcggt ggcggccgtc cgccctcggc accatcctca cgacacccaa atatggcgac      60
gggtgaggaa tggtggggag ttattttag agcggtgagg aaggtgggca ggcagcaggt     120
gttggcgctc taaaaataac tcccgggagt tattttaga gcggaggaat ggtggacacc     180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggtgct ctgggtgttc     420
ttctttgtga tcctcaccct cagcaacagc tcccactgct ccagacctcc ccctttgacc     480
ctcaggatgc ggcggtatgc agatgccatc ttcaccaaca gctaccggaa ggtgctgggc     540
cagctgtccg cccgcaagct gctgcaggac atcatgagca ggcagcaggg agagagcaac     600
caagagcgag gagcataatg aaagcttatc ggggtggcat ccctgtgacc ctccccagt      660
gcctctcctg gccctggaag ttgccactcc agtgcccacc agccttgtcc taataaaatt     720
aagttgcatc attttgtctg actaggtgtc cttctataat attatggggt ggaggggggt     780
ggtatggagc aaggggcaag ttgggaagac aacctgtagg gctcgagggg gggcccggta     840
ccatgtgagc aaaaggccag caaaaggcca ggaaccgtaa aaaggccgcg ttgctggcgt     900
ttttccatag gctccgcccc cctgacgagc atcacaaaaa tcgacgctca agtcagaggt     960
ggcgaaaccc gacaggacta taagatacc aggcgtttcc ccctggaagc tccctcgtgc    1020
gctctcctgt tccgaccctg ccgcttaccg gatacctgtc cgcctttctc ccttcgggaa    1080
gcgtggcgct ttctcatagc tcacgctgta ggtatctcag ttcggtgtag tcgttcgct     1140
ccaagctggg ctgtgtgcac gaaccccccg ttcagcccga ccgctgcgcc ttatccggta    1200
actatcgtct tgagtccaac ccggtaagac acgacttatc gccactggca gcagccactg    1260
gtaacaggat tagcagagcg aggtatgtag gcggtgctac agagttcttg aagtggtggc    1320
ctaactacgg ctacactaga agaacagtat ttggtatctg cgctctgctg aagccagtta    1380
ccttcggaaa aagagttggt agctcttgat ccggcaaaca aaccaccgct ggtagcggtg    1440
gtttttttgt ttacaagcag cagattacgc gcagaaaaaa aggatctcaa gaagatcctt    1500
tgatctttc tacggggtct gacgctcagc tagcgctcag aagaactcgt caagaaggcg    1560
atagaaggcg atgcgctgcg aatcgggagc ggcgataccg taaagcacga ggaagcggtc    1620
agcccattcg ccgccaagct cttcagcaat atcacgggta gccaacgcta tgtcctgata    1680
gcggtccgcc acacccagcc ggccacagtc gatgaatcca gaaaagcggc cattttccac    1740
catgatattc ggcaagcagg catcgccatg agtcacgacg gatcctcgc cgtcgggcat     1800
gcgcgccttg agcctggcga acagttcggc tggcgcgagc cctgatgct cttcgtccag     1860
atcatcctga tcgacaagac cggcttccat ccgagtacgt gctcgctcga tcgatgttt    1920
cgcttggtgg tcgaatgggc aggtagccgg atcaagcgta tgcagccgcc gcattgcatc    1980
agccatgatg gatactttct cggcaggagc aaggtgagat gacaggagat cctgccccgg    2040
cacttcgccc aatagcagcc agtcccttcc cgcttcagtg acaacgtcga gcacagctgc    2100
```

-continued

```
gcaaggaacg cccgtcgtgg ccagccacga tagccgcgct gcctcgtcct gcagttcatt   2160
cagggcaccg gacaggtcgg tcttgacaaa aagaaccggg cgcccctgcg ctgacagccg   2220
gaacacggcg gcatcagagc agccgattgt ctgttgtgcc cagtcatagc cgaatagcct   2280
ctccacccaa gcggccggag aacctgcgtg caatccatct tgttcaatca tgcgaaacga   2340
tcctcatcct gtctcttgat cagatcttga tccoctgcgc catcagatcc ttggcggcaa   2400
gaaagccatc cagtttactt tgcagggctt cccaacctta ccagagggcg ccccagctgg   2460
caattccggt tcgcttgctg tccataaaac cgcccagtct gagct                   2505
```